United States Patent
Shakespeare et al.

(10) Patent No.: US 6,482,852 B2
(45) Date of Patent: Nov. 19, 2002

(54) BICYCLIC SIGNAL TRANSDUCTION INHIBITORS, COMPOSITIONS CONTAINING THEM & USES THEREOF

(75) Inventors: William C. Shakespeare, Framingham, MA (US); Michael G. Yang, Chestnut Hill, MA (US); Rajeswari Sundaramoorthi, Watertown, MA (US); Regine Bohacek, Boston, MA (US); Charles Joseph Eyermann, Sudbury, MA (US); Tomi K. Sawyer, Southborough, MA (US)

(73) Assignee: Ariad Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/854,027

(22) Filed: May 11, 2001

(65) Prior Publication Data

US 2002/0137941 A1 Sep. 26, 2002

Related U.S. Application Data

(62) Division of application No. 09/438,601, filed on Nov. 12, 1999, now abandoned.
(60) Provisional application No. 60/108,106, filed on Nov. 12, 1998.

(51) Int. Cl.⁷ .................. A61K 31/21; A61K 31/185; A61K 31/19; C07C 229/00; C07F 9/22
(52) U.S. Cl. .................. 514/506; 514/553; 514/563; 514/571; 558/172; 562/14; 562/471
(58) Field of Search .................. 562/14, 471; 558/172; 514/563, 571, 553, 506

(56) References Cited

U.S. PATENT DOCUMENTS

6,384,072 B1 * 5/2002 Hattori et al. .............. 514/450

FOREIGN PATENT DOCUMENTS

| WO | WO 96/30332 | 10/1996 |
| WO | WO 97/12903 | 4/1997 |
| WO | WO 97/31016 | 8/1997 |
| WO | WO 99/24442 | 5/1999 |
| WO | WO 99/47529 | 9/1999 |

OTHER PUBLICATIONS

Wang et al., "Design of a high affinity peptidomimetic opiod agonist from peptide pharmacophore models."—(1998) Bioorganic & Medicinal Chemistry Letters, 8 (19): 2685–2688.

Tamami et al., "Pyrazine–based polymeric complex of oxodiperoxochromium (VI) compound as a new stable, mild, efficient and versatile oxidant in organic synthesis."—(1997) Tetrahedron, NL Elsevier Science, 53 (23): 7889–7896.

Reiner Luckenback, "Beilsteins Handbuch der organischen Chemie."—(1987) Springer–Verlag, 4th Edition, 5th Suppl., vol. XVIII, Part 9, p. 650, paragraph 1.

Reiner Luckenback, "Beilsteins Handbuch der organischen Chemie."—(1985) Springer–Verlag, 4th Edition, 4th Suppl., vol. XIII, Part 4, p. 2819, paragraph 5.

Bernhard Prager et al., "Beilsteins Handbuch der organischen Chemie."—(1929) Springer–Verlag, 4th Edition, vol. XII, p. 1207, paragraph 3.

* cited by examiner

Primary Examiner—Deborah C. Lambkin
(74) Attorney, Agent, or Firm—David L. Berstein

(57) ABSTRACT

This invention concerns compounds for inhibiting intracellular signal transduction, especially intracellular signal transduction mediated by one or more molecular interactions involving a phosphotyrosine-containing protein. This invention also relates to pharmaceutical compositions containing the compounds and prophylactic and therapeutic methods involving pharmaceutical and veterinary administration of the compounds. The compounds are of the formula

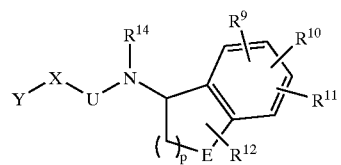

as defined herein.

81 Claims, No Drawings

BICYCLIC SIGNAL TRANSDUCTION INHIBITORS, COMPOSITIONS CONTAINING THEM & USES THEREOF

RELATED APPLICATIONS

This application is a divisional of U.S. Ser. No. 09/438,601 (filed Nov. 12, 1999), abn., which is a continuation in part of U.S. Ser. No. 60/108,106 (filed Nov. 12, 1998), the full contents of both of which are hereby incorporated herein by reference.

FIELD OF THE INVENTION

This invention concerns a new class of compounds which have a broad range of useful biological and pharmacological activities. In particular, these compounds are useful for inhibiting intracellular signal transduction, especially intracellular signal transduction mediated by one or more molecular interactions involving a phosphotyrosine-containing protein. This invention also relates to pharmaceutical compositions containing the compounds and prophylactic and therapeutic methods involving pharmaceutical and veterinary administration of the compounds.

BACKGROUND OF THE INVENTION

Cellular signal transduction, i.e., the series of events leading from extracellular events to intracellular sequelae, is an aspect of cellular function in both normal and disease states. Numerous proteins that function as signal transducing molecules have been identified, including receptor and non-receptor tyrosine kinases, phosphatases and other molecules with enzymatic or regulatory activities. These molecules generally demonstrate the capacity to associate specifically with other proteins to form a signaling complex that can alter cell activity.

Signaling proteins often contain domain(s) of conserved sequence which constitute catalytic domains such as kinase or phosphatase domains, or serve as non-catalytic modules that direct protein:protein or other inter- or intramolecular interactions during signal transduction. Such domains include among others, Src homology 2 ("SH2") and phosphotyrosine interaction ("PI") domains. SH2 and PI domains recognize, i.e., bind to, proteins containing characteristic peptide sequences which include one or more phosphorylated tyrosine ("pTyr") residues. Significant information related to such domains, proteins containing them, the production of proteins containing such domains (including protein fragments and fusion proteins), the characteristic peptide sequences which they recognize and the biological and/or clinical role played by the interactions of such proteins has been described in the scientific literature. See e.g. U.S. Pat. No. 5,667,980, PCT/US97/02635 ("Cell-Based Assay") and WO 97/39326 ("In Vitro Fluorescence Polarization Assay") and references cited therein for additional background information on SH2 and PI domains, inhibition of intermolecular interactions mediated by such domains, assays and related topics.

The protein domains of the tyrosine kinase, Src, gave rise to the "Src homology" ("SH") nomenclature and illustrate this class of proteins. At least nine members of the Src family of tyrosine kinases have been identified to date in vertebrates including Src (alternatively known as c-src and pp60c-src), Fyn, Yes, Lyn, Hck, Fgr, Blk and Yrk. Sequence analysis of the Src tyrosine kinases reveals that each family member contains an N-terminal membrane anchor, a poorly conserved "unique" region of 40–70 amino acids, a Src homology 3 (SH3) domain of about sixty amino acids capable of protein-protein interactions with proline-rich sequences and a Src homology 2 (SH2) domain comprising about 100 amino acid residues which mediates binding of the Src family member of phosphotyrosine-(pTyr) containing peptides and proteins (reviewed in Superti-Furga, FEBS Lett. 369:62–66 (1995). Several cognate phosphoproteins known to bind the Src SH2 domain include middle T antigen, PDGF receptor, EGF receptor, and focal adhesion kinase (FAK). See Courtneidge et al, J. Virol. 65:3301–3308 (1991); Moi et al. EMBO J. 12:2257–2264 (1993); Luttrell et al. Proc. Natl. Acad. Sci. USA 91:83–87 (1994); and Xing et al, Mol. Biol. Cell 5:413–421 (1994). For additional information on other SH2 domains (including, e.g., ZAP-70, Syk, Shc, Tsk, Btk, VAV, Grb2, Crk, STATs) and PI domain-containing proteins, see WO 97/39326 and references cited therein.

The molecular structure of several SH2 domains has been solved and, in particular, the molecular structure of certain SH2 domains in complex with a phosphotyrosine-containing peptide or peptide analog has been elucidated. See Waksman et al, Cell 72:779–790 (1993); Xu et al. Biochemistry 34:2107–2121 (1995); Hatada et al, Nature 377(6544), 32–38 (1995). Whereas the general consensus sequence of Src family SH2-binding peptides, for example, comprises a pTyr-X-X-(Leu/Ile) motif, SH2 domain binding specificity is thought to be influenced significantly by the specific amino acids located carboxy-terminal to the pTyr residue. For example, the pp60c-src, Fyn, Lck and Fgr SH2 domains prefer the sequence pTyr-GluGlu-Ile. See Songyang et al, Cell 72:767–778 (1993). Crystallographic data concerning pp60c-src SH2 in complex with synthetic peptides has revealed, in particular, two important binding determinants for binding to phosphotyrosine-containing proteins or peptides: the phosphotyrosine binding site which is electropositive in nature such that phosphotyrosine binding is stabilized and the lipophilic binding site which stabilizes binding of pTyr+3 residues within the phosphotyrosine-containing peptides via hydrophobic contacts. Reviewed by Brown and Cooper, Biochim. Biophys. Acta 1287 (2–3):121–149 (1996).

Structural studies of phosphotyrosine-containing peptides complexed with isolated SH2 domains has provided information regarding the molecular interactions of peptide ligands with the SH2 domain peptidyl binding site. Recent attempts have been made to extrapolate these data to design novel peptide ligands and peptidomimetic agonists of SH2-mediated signaling. For example, Plummer et al reported that incorporation of C-terminal D-amino acid residues to tripeptide SH2 domain ligands increases affinity relative to their L-amino acid-containing counterparts. See Plummer et al, Drug Design Discovery 13:75–81 (1996). Burke et al reported that hexapeptides containing difluoro-(phosphonomethyl)phenylalanine bound SH2 domains with high relative affinity compared to analogous pTyr peptides and were resistant to naturally-occurring cellular phosphatases. Studies of the pTyr residue of peptide agonists of the Src SH2 domain have shown that that phosphate ester is important for molecular recognition, and that significant loss in binding occurs when it is replaced with sulfate, carboxylate, nitro, hydroxy or amino groups. See Gilmer et al, J Biol Chem 269:31711–31719 (1994).

Many signaling pathways which play critical roles in disease processes are mediated by the binding of a phosphotyrosine-containing protein or protein domain with an SH2 or other protein receptor for a tyrosine-phosphorylated domain. Pharmaceutical agents which interfere with signaling mediated by such molecules, e.g., which interfere with the formation or stability of such signaling complexes, may be used for precise intervention in these complex biological processes in order to treat or prevent the diseases or pathological effects mediated by such signaling. Such interference may be achieved through a variety of mechanisms, including competitive inhibition of a phosphotyrosine-containing ligand with its receptor (e.g., with an SH2-containing protein), inhibition of phosphorylation of the tyrosine residue of such a ligand, inhibition of activation of a kinase which catalyzes the phosphorylation of a ligand in a signaling pathway, etc.

Compounds that can enter cells and block a signal transduction pathway of interest, such as an SH2-mediated pathway, would be of great interest as reagents for biological research and for pharmaceutical and veterinary uses.

SUMMARY OF THE INVENTION

This invention concerns compounds of Formula I, or pharmaceutically acceptable derivatives thereof:

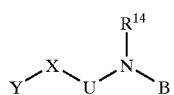

I in which

Y is (a)

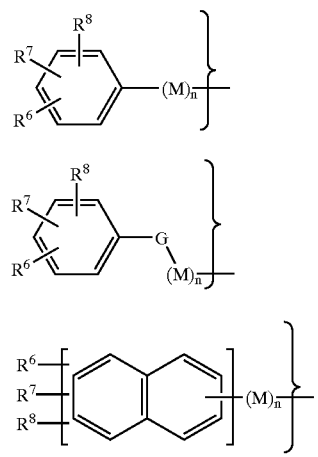

(b)

(c)

G is —O—, —S— or —NR—;

$R^6$ comprises —OR, —APO$_3$RR', —OPO$_3$RR', —ASO$_3$R, —OSO$_3$R, —ACO$_2$R, —A-tetrazole, —A—N—(PO$_3$RR')(PO$_3$RR')', —ASO$_2$NRR', —ACOCF$_3$, —(C=O)J, —C(R)(J)(K) or —C(Z)(J)(K);

where each occurrence of A is independently a covalent bond, —G—M— or —(M)$_m$—;

each occurrence of M is an independently selected, substituted or unsubstituted, methylene moiety, and any M-M' moiety may be electronically saturated or unsaturated and/or may be part of a 3–8-membered ring. Illustrative "M" moieties include —CH$_2$—, —CHF—, —CF$_2$—, —CHOH—, —CH(Me)—, etc.

Each n is independently 0, 1, 2, 3, 4 or 5 (in many embodiments n is 0, 1 or 2);

each m is independently 0, 1 or 2;

J and K are independently selected from the group consisting of —APO$_3$RR', —OPO$_3$RR', —ASO$_3$R, —OSO$_3$R, —ACO$_2$R, —A-tetrazole, —ASO$_2$NRR', —(M)$_n$NRR' and —(M)$_n$OR;

Z is a halogen (i.e., F, Cl, Br or I);

$R^7$ and $R^8$ are independently R, —CN, —NO$_2$, Z, J, —A(M)$_n$aliphatic, —G(M)$_n$aliphatic, —(M)$_n$COCF$_3$, —(M)$_n$OH, —(M)$_n$COOR, —A—(M)$_n$NRR', —G—(M)$_q$NRR', —(M)$_n$CHO, —A(M)$_n$N(R)(CO)R', —A(M)$_n$N(R)(CO)GR', —G(M)$_q$N(R)(CO)R', —G—(M)$_q$N(R)(CO)G'R', —A—(M)$_n$—CO—NRR', or —G—(M)$_n$—CO—NRR', where the aliphatic groups may be substituted or unsubstituted; or $R^7$ is a covalent bond to an $R^4$ substituent of X forming an aliphatic, aryl or heterocyclic ring of 4 to 8 atoms (including, for example a 5-membered nitrogen-containing ring of an indole moiety). Each occurrence of R (unnumbered) represents hydrogen or an aliphatic, heteroaliphatic, aryl, heteroaryl, (aryl)aliphatic-, or (heteroaryl)aliphatic-moiety, each of which (other than hydrogen) may be substituted or unsubstituted, e.g., with any of the various substituents listed, illustrated or otherwise disclosed herein. While each occurrence of "R" within a given compound is thus independently selected, where multiple R groups are depicted in the same figure or moiety, the various R groups are generally marked R, R', R" and so on, as a reminder that they may be the same or different. (The same is true in the case of numbered "R" groups and other variables such as "m", "n", "M", etc. where apostrophes are used for the same purpose. Note also that the n M groups in a "M$_n$" moiety may be the same or different from one another.)

q is an integer from 1 to 8, and in many embodiments is 1, 2 or 3;

X is: —(CR$^3$R$^4$)$_m$— or —NR$^4$—;

$R^3$ is hydrogen, R(CO)NR'—, RR'N(CO)NR"—, R'SO$_2$NR—, R'CSNR—, RR'NCSNR"—, RR'NSO$_2$NR"—, R'OCONR—, RR'N—, or

$R^4$ is hydrogen, aliphatic (which may be branched, unbranched or cyclic), cycloaliphatic-(M)$_n$—, aryl-(M)$_n$—, heterocyclic-(M)$_n$—, RSO$_2$(M$_n$)—, (CO$_2$R)(M)$_n$— or (RR'N—CO)(M)$_n$, where the aliphatic, cycloaliphatic, aryl and heterocyclic groups are substituted or unsubstituted;

B is

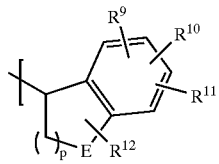

where

E is M, G or one of the following:

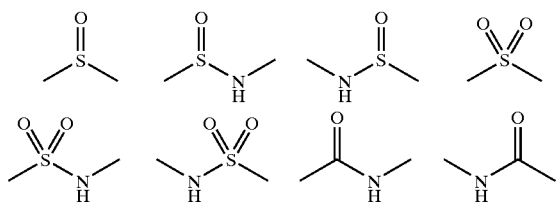

p is 1, 2, 3 or 4;

$R^9$, $R^{10}$, $R^{11}$ and $R^{12}$ are independently —$(M)_n Z$, —$(M)_n R$, —$(M)_n GR$, —$(M)_n WR$ or —$(M)_n WGR$, including, among others, moieties such as R, —OR, —SR, —CHO, —COR, —COOH (or amide, ester, carbamate, urea, oxime or carbonate thereof, —$NH_2$ (or substituted amine, amide, urea, carbamate or guanidino derivative therof), halo, trihaloalkyl, cyano, —$SO_2$—$CF_3$, —$OSO_2F$, —$OS(O)_2R$, —$SO_2$—NHR, —$NHSO_2R$, sulfate, sulfonate, aryl and heteroaryl moieties. Alternatively, $R^{10}$ and $R^{11}$ are covalently linked together to form an aliphatic, hetercyclic or aryl fused ring, typically of 5–7 members. For example, in some embodiments, $R^{10}$ and $R^{11}$ comprise —G—$(M)_n$—G'—, as illustrated by the following structure for B where, for the sake of example, each M is —$CH_2$— and n is 3:

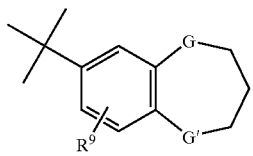

where in some cases G is —O— and G' is —S—, for example.

$R^{14}$ is R (H is generally preferred); and,

U and W are independently —CO—, —CS—, —M—, —SO—, or —$SO_2$—:

a pharmaceutically acceptable derivative thereof.

Compounds of Formula I thus include compounds having the following structures:

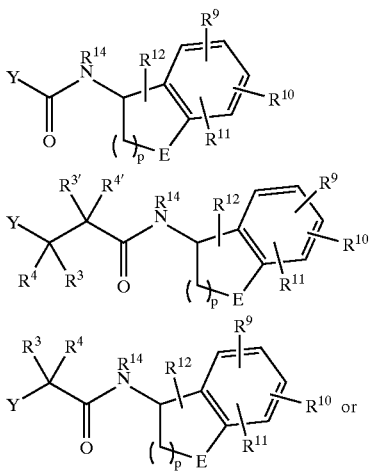

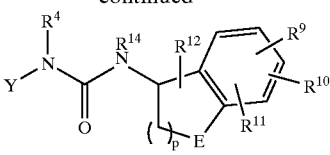

and comprise a number of subgenera of particular interest. Representative subgenera are illustrated in the examples which follow.

One subgenus includes compounds in which at least one $R^4$ moiety is H and at least one $R^3$ moiety is either H or $NH_2$. Compounds of the latter sort include those in which X is

Also of interest are the subgenera of compounds in which the nitrogen atom of the moiety X is further elaborated, as depicted below:

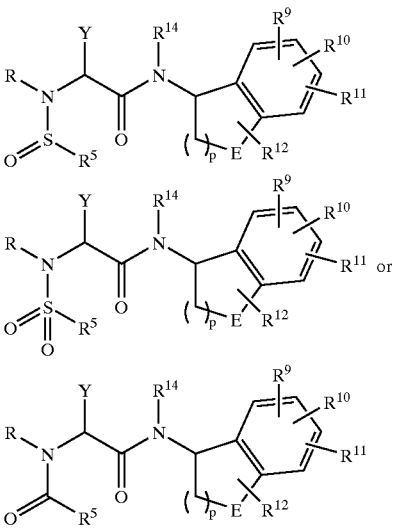

where $R^5$ comprises a substituted or unsubstituted, lower (i.e., containing 1–8 carbon atoms) aliphatic or alkoxyl group, or is a substituted or unsubstituted —$(M)_n$-aryl or —$(M)_n$-heterocyclic (including e.g., substituted and unsubstituted phenyl or benzyl group, or a homolog and heterocyclic analog thereof, including e.g., 2-naphthyl, 3-indolyl, and 1-imidazolyl).

Such compounds are further illustrated by the subset thereof in which $R^5$ comprises —$(M)_n CH_3$, —$(M)_n$aryl, —$(M)_n$heterocyclic, —$(M)_n CN$, —$(M)_n COOR$, where n is 0, 1, 2, 3, 4, or 5. For instance, in some such compounds $R^5$ is a substituted or unsubstituted methyl, ethyl, n-propyl, i-propyl, n-butyl, sec-butyl, t-butyl, n-pentyl, sec-pentyl, i-pentyl, cyclo pentyl, etc. or benzyl moiety. In other such compounds $R^5$ comprises —$(CH_2)_n CH_3$, —$(CH_2)(CH_2)_n$aryl, —$(CH_2)(CH_2)_n$heterocyclic, —$(CH_2)(CH_2)_n CN$ or —$(CH_2)(CH_2)_n COOR$, where n again is 0, 1, 2, 3, 4, or 5. Examples of such compounds include those in which $R^5$ comprises —$CH_2 CN$, —$(CH_2)CO_2R$, —$(CH_2)_2 CO_2R$, —$(CH_2)_3 CO_2R$, —$(CH_2)_4 CO_2R$, where R is H, lower alkyl or benzyl.

In some embodiments of compounds of the structure

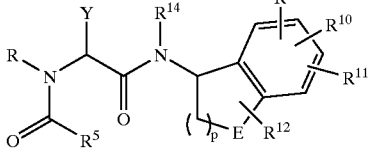

$R^5$ comprises —O—$(M)_n$$CH_3$, —O$(M)_n$aryl, —O$(M)_n$heterocyclic, —O$(M)_n$CN, or —O$(M)_n$COOR, where n is 0, 1, 2, 3, 4, or 5. In specific cases, $R^5$ comprises —O$(CH_2)_n$$CH_3$, —O$(CH_2)(CH_2)_n$aryl, —O$(CH_2)(CH_2)_n$heterocyclic, —O$(CH_2)(CH_2)_n$CN, or —O$(CH_2)(CH_2)_n$COOR. In numerous cases, $R^5$ comprises —O-(substituted or unsubstituted lower alkyl or benzyl.

Another subgenus of interest includes amides of the formula:

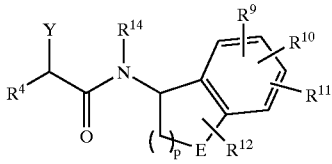

where $R^4$ is hydrogen, substituted or unsubstituted aliphatic (which may be branched, unbranched or cyclic), substituted or unsubstituted aryl-$(M)_n$—, substituted or unsubstituted heterocyclic-$(M)_n$—, or $(CO_2R)(M)_n$—. Such compounds are illustrated by those in which $R^4$ is —$(M)_n$(CO)OR, —$(M)_n$$SO_2$R, —$(M)_n$(CO)NRR', or —$(M)_n$(tetrazole), including, for example, compounds in which $R^4$ is —$CH_2$COOR, —$CH_2$$SO_2$R, —$CH_2$(CO)NRR', or -tetrazole. Simple members of this subgenus are those in which the R group(s) of $R^4$ is (are independently) H, lower alkyl (e.g., methyl, ethyl, n-propyl, isopropyl, n-butyl, isobutyl, tbutyl, etc.) or benzyl.

Another subgenus includes ureas of the formula:

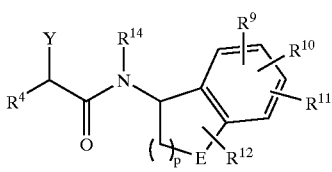

where $R^1$, $R^2$, $R^4$, $R^{14}$, Y and m are defined as above. Thus, $R^4$ may be simply H or may be a more complex $R^4$ moiety such as are noted above.

Another subgenus includes amides of the formula:

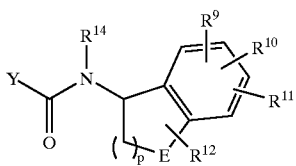

In many examples of all of the foregoing compounds, one or more R moieties (R', R" etc) are H. Also, in many compounds of interest, $R^{14}$ is H.

Compounds of Formula I, including, among others, compounds of the various subgenera described above, include those in which Y comprises

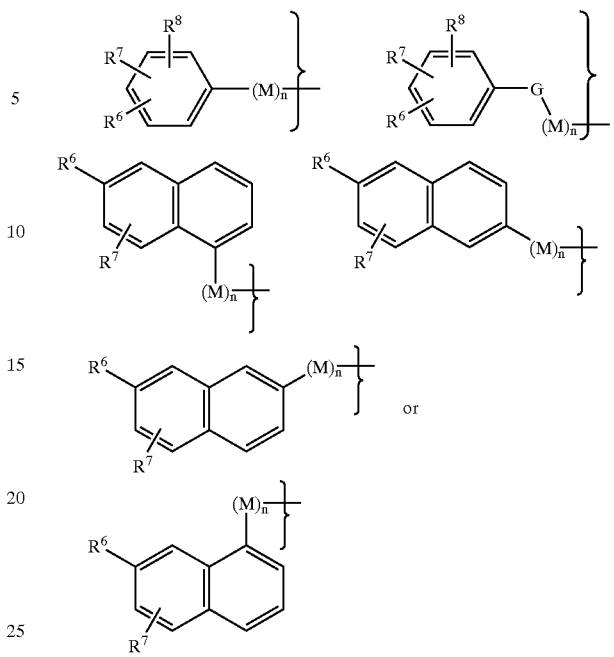

Such compounds in which $R^6$ comprises —OR, —APO$_3$RR', —OPO$_3$RR', —ASO$_3$R, —OSO$_3$R, —ACO$_2$R, —A-tetrazole, —A—N—(PO$_3$RR')(PO$_3$RR')', —ASO$_2$NRR', —ACOCF$_3$, —C(R)(J)(K) or —C(Z)(J)(K) are of particular interest. Embodiments in which $R^7$ and $R^8$ are independently H, —CN, —NO$_2$, halogen, J, —A—$(M)_n$aliphatic, —G—$(M)_n$aliphatic, —$(M)_n$COCF$_3$, —$(M)_n$OR, —$(M)_n$COOR, —A—$(M)_n$NRR', —G—$(M)_q$NRR', —$(M)_n$CHO, —A—$(M)_n$N(R)(CO)R', —G—$(M)_q$N(R)(CO)R', —A—$(M)_n$—CO—NRR', or —G—$(M)_n$—CO—NRR', where the aliphatic groups may be substituted or unsubstituted; or $R^7$ is a covalent bond to an $R^4$ substituent of X to form a ring of 4 to 8 atoms are also of particular interest (including among others, those compounds in which the R groups of $R^6$ and/or of $R^7$ and $R^8$ are H). This set of compounds is illustrated by those in which $R^6$ comprises —OR, —APO$_3$RR', —OPO$_3$RR', —ACO$_2$R, —ACOCF$_3$ or —C(R)(J)(K); A comprises —$M_m$— (e.g., —CH$_2$—, —CF$_2$—, —CHF—, —CHOH—, —CH$_2$CF$_2$—, etc), —GM— (e.g. —OCH$_2$—) or a covalent bond; each R and R' is H, or substituted or unsubstituted lower alkyl or substituted or unsubstituted benzyl; and, $R^7$ and $R^8$ are independently H, J, —A—$(M)_n$substituted or unsubstituted aliphatic, —$(M)_n$COCF$_3$, —$(M)_n$OH, —$(M)_n$COOR, —A—$(M)_n$NRR', —$(M)_n$CHO, —A—$(M)_n$N(R)(CO)R' or —A—$(M)_n$—CO—NRR'. For example, in some such cases, $R^6$ comprises —OH, —PO$_3$RR', OPO$_3$RR', —CH$_2$PO$_3$RR', —CF$_2$PO$_3$RR, —OCH$_2$CO$_2$R, —NHCH$_2$CO$_2$R, —CH$_2$CO$_2$R, —CF$_2$CO$_2$R, —N(PO$_3$RR')(PO$_3$RR')', —CH$_2$SO$_3$R, —CF$_2$SO$_3$R, —CH$_2$COCF$_3$, —CF$_2$COCF$_3$, —CH(PO$_3$RR')$_2$, —CH(OH)(PO$_3$RR'), —CH(NH$_2$)(PO$_3$RR'), —CH(CO$_2$R)$_2$, —CF(CO$_2$R)$_2$, —CH(PO$_3$RR')(CO$_2$R"), —CH(PO$_3$RR')(SO$_3$R"), —CH(PO$_3$RR')(SO$_2$NH$_2$), —CH(SO$_2$NH$_2$)$_2$, or —CH(SO$_3$RR')$_2$. In some such compounds, one or more of R, R' and R" in the —PO$_3$RR', —OPO$_3$RR', —CH$_2$PO$_3$RR', —CF$_2$PO$_3$RR', —OCH$_2$CO$_2$R, —NHCH$_2$CO$_2$R, —CH$_2$CO$_2$R, —CF$_2$CO$_2$R, —CF$_2$CO$_2$R, —N(PO$_3$RR')(PO$_3$RR') , —CH$_2$SO$_3$R, —CF$_2$SO$_3$R, —CH$_2$COCF$_3$, —CF$_2$COCF$_3$, —CH(PO$_3$RR')$_2$, —CH(OH)(PO$_3$RR'), —CH(NH$_2$)(PO$_3$RR'), —CH(CO$_2$R)$_2$, —CF(CO$_2$R)$_2$, —CH(PO$_3$RR')

($CO_2R''$), —$CH(PO_3RR')(SO_3R'')$, —$CH(PO_3RR')$ ($SO_2NH_2$), —$CH(SO_2NH_2)_2$, or —$CH(SO_3RR')_2$ moiety is H. In others, one or more of those R groups is —$(M)_m$—$CH_2Z$, —$(M)_m$—$CHZ_2$, —$(M)_m$—$CZ_3$, —$R^{15}$, —M—O—CO—$OR^{15}$ or —M—O—$R^{15}$, where Z is halogen and $R^{15}$ is substituted or unsubstituted lower aliphatic, aryl or heterocyclic. For example, in various embodiments, $R^{15}$ is methyl, ethyl, n-propyl, i-propyl, n-butyl, isobutyl, t-butyl, n-amyl, sec-amyl, benzyl or substituted benzyl, and M is $CH_2$, CHR (e.g. $CHCH_3$ etc.) and the like. Further illustrations include —$CH_2$—O—CO—OEt, —CH(Me)—O—CO—OEt, —$CH_2$—O—CO—t-butyl, etc.

In one subgenus of the foregoing compounds, $R^7$ and $R^8$ are both H. In another subgenus $R^7$ is —$N(M_nCOOR)$ $(M_nCOOR)'$, e.g., —$N(CH_2CO_2R)_2$. In another subgenus, $R^7$ is J, —A—$(M)_n$(substituted or unsubstituted aliphatic, aryl or heterocyclic), —$(M)_nCOCF_3$, —$(M)_nOH$, —$(M)_nCOOR$, —A—$(M)_nNRR'$, —$(M)_nCHO$, —A—$(M)_nN(R)(CO)R'$, —A—$(M)_n$—NRR' or —A—$(M)_n$—CO—NRR'; and $R^8$ is H. The latter subgenus is illustrated by compounds in which $R^7$ is lower alkyl, lower alkenyl, —OH, —$NH_2$, —$NO_2$, —CN, —NHR, —NHCOR, —CHO, —$CH_2CHO$, —$PO_3RR'$, —$OPO_3RR'$, —$CH_2PO_3RR'$, —$CF_2PO_3RR'$, —$OCH_2CO_2R$, —$NHCH_2CO_2R$, —$CH_2CO_2R$, —$CF_2CO_2R$, —$SO_3R$, —$CH_2SO_3R$, —$CF_2SO_3R$, —$COCF_3$, —$COCH_2F$, —$COCF_2H$, —$CF_2COCF_3$ or —$SO_2NH_2$. In some such compounds, one or both of R and R' in —$PO_3RR'$, —$OPO_3RR'$, —$CH_2PO_3RR'$, —$CF_2PO_3RR'$, —$OCH_2CO_2R$, —$NHCH_2CO_2R$, —$CH_2CO_2R$, —$CF_2CO_2R$, —$SO_3R$, —$N(PO_3RR')(PO_3RR')'$,—$CH_2SO_3R$, or —$CF_2SO_3R$ is H. In others, one or more of those R groups is —$(M)_m$—$CH_2Z$, —$(M)_m$—$CHZ_2$, —$(M)_m$—$CZ_3$, —$R^{15}$, —M—O—CO—$OR^{15}$ or —M—O—CO—$R^{15}$, where Z is halogen and $R^{15}$ is substituted or unsubstituted lower aliphatic, aryl or heterocyclic. For example, in individual cases, $R^{15}$ is methyl, ethyl, n-propyl, i-propyl, n-butyl, isobutyl, t-butyl, n-amyl, sec-amyl, benzyl or substituted benzyl, and M is $CH_2$, CHR (e.g. $CHCH_3$ etc.) and the like.

In an illustrative subgenus, $R^6$ comprises —$APO_3RR'$ (e.g., —$OPO_3H_2$) and $R^7$ is —A—$(M)_n$substituted or unsubstituted aliphatic.

In another subgenus, $R^6$ and $R^7$ are independently selected from J and K.

In another subgenus, $R^6$ is —C(R)(J)(K). Illustrative compounds of this subgenus include those in which $R^6$ is —CH(J)(K) and those in which $R^6$ is —$C(R)(PO_3R'R')(K)$. The latter compounds are illustrated by embodiments in which none, one, two or three of the R groups of the —$C(R)(PO_3R'R')(K)$ moiety are H.

As in previously mentioned cases, compounds of this invention which contain a moiety J, e.g., compounds of Formula I in which $R^6$ is —C(R)(J)(K), include among others embodiments in which one or both of R and R' (e.g., of a —$PO_3RR'$ moiety) are $R^{15}$, —$(M)_m$—$CH_2Z$, —$(M)_m$—$CHZ_2$, —$(M)_m$—$CZ_3$, —M—O—CO—$OR^{15}$ or —M—O—CO—$R^{15}$, where Z is halogen and $R^{15}$ is substituted or unsubstituted lower aliphatic, aryl or heterocyclic (e.g., methyl, ethyl, n-propyl, i-propyl, n-butyl, isobutyl, t-butyl, n-amyl, sec-amyl, benzyl or substituted benzyl), and M is $CH_2$, CHR (e.g. $CHCH_3$ etc.) and the like.

The compounds of Formula I, including the various subgenera and illustrative examples described above, all contain a bicyclic moiety, B, as that term is defined herein and as is illustrated by the following formula:

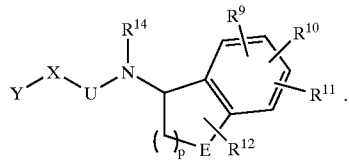

Compounds of this invention include those in which each of $R^9$, $R^{10}$, $R^{11}$ and $R^{12}$ is independently —$(M)_nZ$, —$(M)_nR$, —$G(M)_nR$, —$(M)_nWR$ or —$(M)_nW$—GR. In certain embodiments, one or more of the R, R' and R'' groups of $R^9$, $R^{10}$, $R^{11}$, and $R^{12}$ comprise a halo, hydroxy, aliphatic, amino, amido or sulfonamido moiety. In some embodiments, one or more of $R^9$, $R^{10}$, $R^{11}$, and $R^{12}$ is a substituted aliphatic moiety containing at least one substituent selected from substituted or unsubstituted cycloaliphatic, substituted or unsubstituted aryl, substituted or unsubstituted heteroaryl, —COR, —$CO_2R$, —CO—NRR', and —OR. In some embodiments of particular interest, one or more of $R^9$, $R^{10}$, $R^{11}$, and $R^{12}$ comprises —$(M)_n$(cycloaliphatic), —$(M)_n$(substituted or unsubstituted aryl), —$(M)_n$(substituted or unsubstituted heteroaryl), —$(M)_nCHO$, —$(M)_nCONH_2$, —$(M)_nCSNH_2$, —$(M)_nSONH_2$, —$(M)_nSO_2NRR'$, —$(M)_nOR$, —$(M)_n$(lower aliphatic), —$(M)_n$—C(OR)R'R'', or —$(M)_n$—C=CRR'. For example, in some cases, one or more of $R^9$, $R^{10}$, $R^{11}$, and $R^{12}$ comprise methyl, —$(CH_2)_qR^{13}$ where q is 1–8 and $R^{13}$ comprises methyl; i-propyl; i-butyl; t-butyl; cycloaliphatic; phenyl; substituted phenyl; naphthyl; substituted naphthyl; a 5, 6 or 7-membered heterocyclic ring or a bicyclic heterocylic moiety. In some cases, $R^{12}$ comprises a formyl group on a ring nitrogen. Possible substituents on the R, R' and R'' groups include, among others, halo, hydroxy, alkyl, amino, amido and sulfonamido moieties. Other potential substituents are as disclosed elsewhere herein, including in the numerous specific examples.

Other compounds of Formula I which are of particular interest include those in which one or more of $R^9$, $R^{10}$, $R^{11}$, and $R^{12}$ comprises —$G(M)_n$(aliphatic), —$G(M)_n$ (cycloaliphatic), —$G(M)_n$(substituted or unsubstituted aryl), —$G(M)_n$(substituted or unsubstituted heteroaryl), —$G(M)_nCHO$, —$G(M)_nCONH_2$, —$G(M)_nCSNH_2$, —$G(M)_nSONH_2$, —$G(M)_nSO_2NRR'$, —$G(M)_nOR$, —$G(M)_n$(lower aliphatic), —$G(M)_nC(OR)R'R''$, or —$G(M)_n$—C=CRR', for instance as illustrated by cases in which —$G(M)_n$ comprises —$OCH_2$—, —$SCH_2$— or —$NRCH_2$—.

Compounds of particular interest further include those in which one or more of $R^9$, $R^{10}$, $R^{11}$, and $R^{12}$ comprises —$(M)_nW$—NH—R, e.g., —$(M)_n(CO)$—NH—R, as illustrated by —$(CH_2)_mCONH$—R and —C(O)NR, for example). In some compounds one or more of $R^9$, $R^{10}$, $R^{11}$, and $R^{12}$ comprises —$O(M)_m$(aliphatic).

In some cases $R^{11}$ and $R^{12}$ are both H, as illustrated by the following structure:

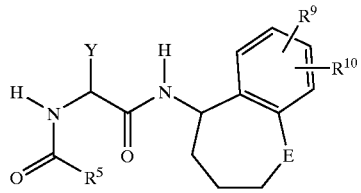

In illustrative embodiments, $R^5$ comprises a substituted or unsubstituted lower aliphatic moiety, $R^9$ comprises —(M)$_n$W—NH—R" and R$^{10}$ comprises —O(M)$_m$ (aliphatic). For example, in some such compounds, R$^9$ comprises —CONH—R" and R$^{10}$ comprises —OM-cycloaliphatic or —OM-branched chain aliphatic. In other cases, R$^9$ comprises —CH$_2$CONH—R and R$^{10}$ comprises —OM-cycloaliphatic or —OM-branched chain aliphatic.

From the perspective of Y moieties, compounds of interest include those compounds of Formula I, including those of the various subgenera and examples herein, in which Y comprises

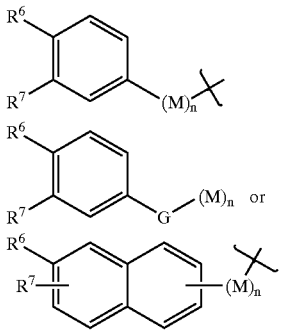

particularly where R$^6$ comprises —OR', —APO$_3$R'R", —ASO$_3$R', —ACO$_2$R', —ASO$_2$NR'R", —ACOCF$_3$, or —C(R')(J)(K); and, R$^7$ is H, —CN, —NO$_2$, halogen, J, —A—(M)$_n$substituted or unsubstituted aliphatic, —(M)$_n$COCF$_3$, —(M)$_n$OH, —(M)$_n$COOR, —A—(M)$_n$NRR', —(M)$_n$CHO, —A—(M)$_n$N(R)(CO)R' or —A—(M)$_n$—CO—NRR'. For example, in some cases R$^6$ comprises —PO$_3$RR', —OPO$_3$RR', —OSO$_2$NRR', —(CH$_2$)PO$_3$RR', —(CF$_2$)PO$_3$RR' or —CRJK; and R$^7$ comprises R (including among others, H, alkyl, alkenyl, etc.) —CN, amido, acylamino, J (e.g. —CO$_2$R), or —CHO. For example, in some cases, R$^6$ comprises —OPO$_3$RR' or —(CF$_2$)PO$_3$RR' and R$^7$ is H. In some embodiments one or more R groups (including R', R", etc) of R$^6$ comprises —(M)$_m$—CH$_2$Z, —(M)$_m$—CHZ$_2$, —(M)$_m$—CZ$_3$, —R$^{15}$, —M—O—CO—OR$^{15}$ or —M—O—CO—R$^{15}$, where Z is H or halogen and R$^{15}$ is substituted or unsubstituted lower aliphatic, aryl or heterocyclic. For example, in individual cases, R$^{15}$ is methyl, ethyl, n-propyl, i-propyl, n-butyl, isobutyl, t-butyl, n-amyl, sec-amyl, benzyl or substituted benzyl, and M is CH$_2$, CHR (e.g. CHCH$_3$ etc.) and the like.

Compounds of the structure

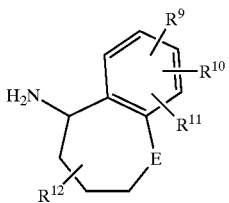

(as well as homologs in which p is 1 or 2) are of interest as intermediates in the preparation of compounds of this invention. Of particular interest are such compounds in which R$^9$ and R$^{10}$ are independently halo, R, —OR, —SR, —NRR', —COR, or —(M)$_n$W—NHR, and R$^{11}$ and R$^{12}$ are as previously defined, including cases in which R$^{11}$ and R$^{12}$ are H.

Compounds of this invention which are of special interest include those which bind to a given SH2 domain (or protein containing such SH2 domain) with a IC$_{50}$ value of less than 50 μM, preferably less than 20 μM, as determined by any scientifically valid method, in vitro or in vivo. SH2 domains of current interest include those of a Src, Fyn, Lck, Yes, Blk, Lyn, Fgr, Hck, Yrk, ZAP-70, Syk, STAT or Abl protein.

Also of interest are pharmaceutical compositions comprising a compound of this invention, or a pharmaceutically acceptable derivative thereof, and one or more pharmaceutically acceptable excipients.

Compounds of this invention (or a composition containing such a compound) can be administered to cells or to animals, preferably a mammal in need thereof, as a method for inhibiting SH2-mediated signal transduction therein. In particular cases, it will be advantageous to carry out that method using a pharmaceutical composition containing a compound which specifically binds to an SH2 domain of Src, ZAP-70, Syk, or STAT 6. In other cases it will be advantageous to carry out that method where the SH2-mediated signal transduction is mediated by a PDGF receptor protein, EGF receptor protein, HER2/Neu receptor protein, fibroblast growth factor receptor protein, focal adhesion kinase protein, p130 protein, or p68 protein.

Cases in which a mammal may be in need of inhibition of SH2-mediated signaling include cases in which the mammal has a proliferative disease, cancer, restenosis, osteoporosis, inflammation, allergies, or cardiovascular disease. In such cases, administering a therapeutically effective amount of the composition to the mammal, preferably to a human patient, will constitute treating or preventing the proliferative disease, cancer, restenosis, osteoporosis, inflammation, allergic reaction, or cardiovascular disease in the recipient or a method for causing immunosuppression in the recipient.

Generally preferred compounds of this invention include any of the foregoing compounds which yield an observable IC$_{50}$ value, when tested against an SH2 domain of interest and a pTyr-containing peptide ligand (or mimic thereof for that SH2 domain, of 50 μM or better, preferably 5 μM or better, more preferably 1 μM or better, and even more preferably, 500 nM or better, as determined by any scientifically valid measure, especially when the SH2 domain is from a Src, Fyn, Lck, Yes, Blk, Lyn, Fgr, Hck, Yrk, ZAP, Syk, STAT or Abl protein.

A pharmaceutical composition may be prepared containing a compound of this invention (including a pharmaceutically acceptable derivative thereof) together with one or more pharmaceutically acceptable excipients.

A compound of this invention, preferably in the form of a pharmaceutical composition, may be administered to a mammal in need thereof, preferably a human patient, as a method for inhibiting SH2-mediated signal transduction in the recipient mammal. In some cases, the compound may be selected based on its ability to specifically bind to an SH2 domain, e.g. of Src, ZAP-70, Syk, or STAT 6, etc., or on its ability to inhibit a signal transduction pathway mediated by an SH2 domain-containing protein. Such use of an appropriately selected compound of this invention thus provides a method for inhibiting SH2-mediated signal transduction which is mediated by a PDGF receptor protein, EGF receptor protein, HER2/Neu receptor protein, fibroblast growth factor receptor protein, focal adhesion kinase protein, p130 protein, or p68 protein. Use of a compound of this invention may be particularly advantageous in cases in which the mammal has a proliferative disease, cancer, restenosis, osteoporosis, inflammation, allergies, or cardiovascular disease. In such cases, administering to the patient a therapeutically effective amount of a compound of this invention, preferably in the form of a pharmaceutical composition, provides a method for treating or preventing a proliferative disease, cancer, restenosis, osteoporosis, inflammation, allergies, or cardiovascular disease in the patient.

DETAILED DESCRIPTION OF THE INVENTION

Compounds and Definitions

As mentioned above, this invention provides a novel class of compounds useful as inhibitors of signal transduction pathways mediated by the interaction of protein receptors for phosphotyrosine-containing proteins, such as proteins containing one or more SH2 domains, with their phosphotyrosine-containing ligands. Compounds of this invention comprise those of Formula I, set forth above, and are illustrated in part by the various classes, subgenera and subsets of compounds noted above, and by the various subgenera and species disclosed elsewhere herein. The compound may be in the form of an individual enantiomer, diastereomer or geometric isomer, or may be in the form of a mixture of stereoisomers.

Also included are pharmaceutically acceptable derivatives of the foregoing compounds, where the phrase "pharmaceutically acceptable derivative" denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof, preferably one which is a signal transduction inhibitor. Pharmaceutically acceptable derivatives thus include among others pro-drugs. A pro-drug is a derivative of a compound, usually with significantly reduced pharmacological activity, which contains an additional moiety which is susceptible to removal in vivo yielding the parent molecule as the pharmacologically active species. An example of a pro-drug is an ester which is cleaved in vivo to yield a compound of interest. Pro-drugs of a variety of compounds, and materials and methods for derivatizing the parent compounds to create the pro-drugs, are known and may be adapted to the present invention.

The term "aliphatic" as used herein includes both saturated and unsaturated, straight chain (i.e., unbranched), branched, cyclic, or polycyclic aliphatic hydrocarbons, which are optionally substituted with one or more functional groups. Unless otherwise specified, alkyl, other aliphatic, alkoxy and acyl groups preferably contain 1–8, and in many cases 1–6, contiguous aliphatic carbon atoms. Illustrative aliphatic groups thus include, for example, methyl, ethyl, n-propyl, isopropyl, cyclopropyl, —CH$_2$-cyclopropyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl moieties and the like, which again, may bear one or more substituents.

Some examples of substituents of aliphatic (and other) moieties of compounds of this invention include: R, —OH, —OR, —SH, —SR, —CHO, =O, —COR, —COOH (or amide, ester, carbamate, urea, oxime or carbonate thereof, —NH$_2$ (or substituted amine, amide, urea, carbamate or guanidino derivative therof, halo, trihaloalkyl, cyano, —SO$_2$—CF$_3$, —OSO$_2$F, —OS(O)$_2$R, —SO$_2$—NHR, —NHSO$_2$R, sulfate, sulfonate, aryl and heteroaryl moieties. Aliphatic, heteraliphatic, aryl and heterocyclic substituents may themselves be substituted or unsubstituted (e.g. mono-, di- and tri-alkoxyphenyl; methylenedioxyphenyl or ethylenedioxyphenyl; halophenyl; or -phenyl-C(Me)$_2$—CH$_2$—O—CO—[C3–C6] alkyl or alkylamino). Additional examples of generally applicable substituents are illustrated by the specific embodiments shown in the Examples which follow.

The term "aliphatic" is thus intended to include alkyl, alkenyl, alkynyl, cycloalkyl, cycloalkenyl, and cycloalkynyl moieties.

As used herein, the term "alkyl" includes both straight, branched and cyclic alkyl groups. An analogous convention applies to other generic terms such as "alkenyl", "alkynyl" and the like. Furthermore, as used herein, the language "alkyl", "alkenyl", "alkynyl" and the like encompasses both substituted and unsubstituted groups.

The term "alkyl" refers to groups usually having one to eight, preferably one to six carbon atoms. For example, "alkyl" may refer to methyl, ethyl, n-propyl, isopropyl, cyclopropyl, butyl, isobutyl, sec-butyl, tert-butyl, cyclobutyl, pentyl, isopentyl tert-pentyl, cyclopentyl, hexyl, isohexyl, cyclohexyl, and the like. Suitable substituted alkyls include, but are not limited to, fluoromethyl, difluoromethyl, trifluoromethyl, 2-fluoroethyl, 3-fluoropropyl, hydroxymethyl, 2-hydroxyethyl, 3-hydroxypropyl, benzyl, substituted benzyl and the like.

The term "alkenyl" refers to groups usually having two to eight, preferably two to six carbon atoms. For example, "alkenyl" may refer to prop-2-enyl, but-2-enyl, but-3-enyl, 2-methylprop-2-enyl, hex-2-enyl, hex-5-enyl, 2,3-dimethylbut-2-enyl, and the like. The language "alkynyl," which also refers to groups having two to eight, preferably two to six carbons, includes, but is not limited to, prop-2-ynyl, but-2-ynyl, but-3-ynyl, pent-2-ynyl, 3-methylpent-4-ynyl, hex-2-ynyl, hex-5-ynyl, and the like.

The term "cycloalkyl" as used herein refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of other aliphatic or heteroaliphatic or heterocyclic moieties, may optionally be substituted.

The term "heteroaliphatic" as used herein refers to aliphatic moieties which contain one or more oxygen, sulfur, nitrogen, phosphorous or silicon atoms, e.g., in place of carbon atoms. Heteroaliphatic moieties may be branched, unbranched or cyclic and include heterocycles such as morpholino, pyrrolidinyl, etc.

The term "heterocycle" as used herein refers to cyclic heteroaliphatic and heteroaryl groups and preferably three to ten ring atoms total, includes, but is not limited to heteroaliphatic moieties such as oxetane, tetrahydrofuranyl, tetrahydropyranyl, aziridine, azetidine, pyrrolidine, piperidine, morpholine, piperazine and the like, and heteroaryl moieties as described below.

The terms "aryl" and "heteroaryl" as used herein refer to stable mono- or polycyclic, heterocyclic, polycyclic, and polyheterocyclic unsaturated moieties having 3–14 carbon atom which may be substituted or unsubstituted. Substituents include any of the previously mentioned substituents. Non-limiting examples of useful aryl ring groups include phenyl, halophenyl, alkoxyphenyl, dialkoxyphenyl, trialkoxyphenyl, alkylenedioxyphenyl, naphthyl, phenanthryl, anthryl, phenanthro and the like. Examples of typical heteroaryl rings include 5-membered monocyclic ring groups such as thienyl, pyrrolyl, imidazolyl, pyrazolyl, furyl, isothiazolyl, furazanyl, oxazolyl, isoxazolyl, thiazolyl, oxadiazolyl and the like; 6-membered monocyclic groups such as pyridyl, pyrazinyl, pyrimidinyl, pyridazinyl, triazinyl and the like; and polycyclic heterocyclic ring groups such as benzo[b]thienyl, naphtho[2,3-b]thienyl, thianthrenyl, isobenzofuranyl, chromenyl, xanthenyl, phenoxathienyl, indolizinyl, isoindolyl, indolyl, indazolyl, purinyl, isoquinolyl, quinolyl, phthalazinyl, naphthyridinyl, quinoxalinyl, quinazolinyl, benzothiazole, benzimidazole, tetrahydroquinoline cinnolinyl, pteridinyl, carbazolyl, beta-carbolinyl, phenanthridinyl, acridinyl, perimidinyl, phenanthrolinyl, phenazinyl, isothiazolyl, phenothiazinyl, phenoxazinyl, and the like(see e.g. Katritzky, Handbook of Heterocyclic Chemistry). The aryl or heteroaryl moieties may be substituted with one to five members selected from the group consisting of hydroxy, C1–C8 alkoxy, C1–C8 branched or straight-chain alkyl, acyloxy, carbamoyl, amino, N-acylamino, nitro, halo, trihalomethyl, cyano, and carboxyl. Aryl moieties thus include, e.g. phenyl; substituted phenyl bearing one or more substituents selected from groups including: halo such as chloro or fluoro, hydroxy, C1–C6 alkyl, acyl, acyloxy, C1–C6 alkoxy (such as methoxy or ethoxy, including among others dialkoxyphenyl moieties such as 2,3-, 2,4-, 2,5-, 3,4- or 3,5-dimethoxy or diethoxy phenyl or such as methylenedioxyphenyl, or 3-methoxy-5-ethoxyphenyl; or trisubstituted phenyl, such as trialkoxy (e.g., 3,4,5-trimethoxy or ethoxyphenyl), 3,5-dimethoxy-4-chloro-phenyl, etc.), amino, —$SO_2NH_2$, —$SO_2NH$ (aliphatic), —$SO_2N$(aliphatic)$_2$, —O-aliphatic-COOH, and —O-aliphatic-$NH_2$ (which may contain one or two N-aliphatic or N-acyl substituents).

A "halo" substituent may be fluoro, chloro, bromo or iodo.

With respect to nomenclature, note that asymetric moieties such as "—G—M—" are written in the direction or order in which they are intended to be read into a given structure. Thus, "—G—M—" is distinct from "—M—G—". For example, in "Ar—A—COOR", where A is —G—M—, the structure Ar—G—M—COOR, not Ar—M—G—COOR, is intended.

Synthesis

Those of ordinary skill in this art will appreciate that compounds of this invention may be produced using any of a variety of synthetic strategies. We typically use a convergent synthetic scheme in which an intermediate comprising the desired "YXU" moiety, protected as appropriate, is condensed with a second intermediate comprising the desired amino moiety $HR^{14}N(CR^1R^2)_mB$, again, protected as appropriate, to yield (following any necessary deprotection steps) the desired compound of Formula I. A variety of methods and materials for effecting the relevant chemical transformations, product recovery, purification and formulation are known in the art which may be adapted to use in the practice of this invention. The detailed examples which follow illustrate such syntheses and should provide helpful guidance to the practitioner.

Assays for Comparative Functional Evaluation of Compounds

Compounds of this invention may be evaluated in a variety of assays to determine their relative ability to bind to a receptor for a pTyr-containing ligand, such as a protein containing one or more SH2 or PI domains, or to otherwise inhibit an intermolecular interaction mediated by such a domain. See e.g. U.S. Pat. No. 5,667,980 (Pawson; competitive binding assays), PCT/US97/02635 (Rickles et al; cell-based assays) and PCT/US97/06746 (Lynch et al, FP assays). Compounds may also be evaluated for their selectivity of binding to one such receptor (or family of receptors) relative to another such receptor (or family of receptors). The compounds of this invention can be further evaluated by conventional methods for possible therapeutic applications, including evaluations of toxicological and pharmacological activity. For example, the compounds may further be evaluated for activity in inhibiting cellular or other biological events mediated by a pathway involving the molecular interaction of interest using a suitable cell-based assay or an animal model. Cell-based assays and animal models suitable for evaluating inhibitory activity of a test compound with respect to a wide variety of cellular and other biological events are known in the art. New assays and models are regularly developed and reported in the scientific literature.

By way of non-limiting example, compounds which bind to an SH2 domain involved in the transduction of a signal leading to asthma or allergic episodes may be evaluated in a mast cell or basophil degranulation assay. The inhibitory activity of a test compound identified as an SH2 inhibitor by the method of this invention with respect to cellular release of specific mediators such as histamine, leukotrienes, hormonal mediators and/or cytokines, as well as its biological activity with respect to the levels of phosphatidylinositol hydrolysis or tyrosine phosphorylation can be characterized with conventional in vitro assays as an indication of biological activity. [See, e.g., Edward L. Barsumian et al, *Eur. J. Immunol.*, 11:317–323 (1981); M. J. Forrest, *Biochem. Pharmacol.*, 42:1221–1228 (1991) (measuring N-acetyl-betaglucosamin-adase from activated neutrophils); and Stephan et al., *J. Biol. Chem.*, 267:5434–5441 (1992)].

For example, histamine release can be measured by a radioimmunoassay using a kit available from AMAC Inc. (Westbrook, Me.). One can thus evaluate the biological activity of compounds of this invention and compare them to one another and to known active compounds or clinically relevant compounds which can be used as positive controls.

Generally speaking, in such assays $IC_{50}$ scores of 20 μM or less are considered of special interest, scores below 1 μM are considered of particular interest and scores below about 500 nM are of high interest. Inhibitors of this invention may also be tested in an ex vivo assay, e.g., for their ability to block antigen-stimulated contraction of sensitized guinea pig tracheal strip tissue. Activity in this assay has been shown to be useful in predicting the efficacy of potential anti-asthma drugs.

Numerous animal models of asthma have been developed and can be used [for reviews, see Larson, "Experimental Models of Reversible Airway Obstruction", in THE LUNG, Scientific Foundations, Crystal, West et al. (eds.), Raven Press, New York, pp. 953–965 (1991); Warner et al., *Am. Rev. Respir. Dis.*, 141:253–257 (1990)]. Species used in animal models of asthma include mice, rats, guinea pigs, rabbits, dogs, sheep and primates. Other in vivo models available are described in Cross et al., *Lab Invest.*, 63:162–170 (1990); and Koh, et al., *Science*, 256:1210–1213 (1992).

By way of further example, compounds which bind to an SH2 or other domain of interest involved in the transduction of a signal involved in the initiation, maintenance or spread of cancerous growth may be evaluated in relevant conventional in vitro and in vivo assays. See e.g., Ishii et al., *J. Antibiot.*, XLII: 1877–1878 (1989); and U.S. Pat. No. 5,206,249 (issued Apr. 27, 1993).

Compounds which bind to a ZAP SH2 domain or which otherwise inhibit ZAP-70-mediated signaling may be evaluated for immunosuppressive activity, e.g., in any of the well-known in vitro or in vivo immunosuppression assays.

Compounds which bind to a Src SH2 domain or which otherwise inhibit Src-mediated signaling may be evaluated for activity in a variety of assays considered predictive of activity in treating or preventing osteoporosis. Such assays include the various pit assays and calvaria assays, among others. Illustrative assays are described below.

Murine Calvaria Assay

In osteoporosis, excessive bone resorption results in decreased bone density. In vivo and in vitro models of bone resorption are used to study the processes leading to osteoporosis. In vitro, fetal rat long bone and murine calvaria cultures are routinely used. Both models display similar responses to parathyroid hormone (PTH), a physiological modulator of bone resorption (Stern, P. H. and N. S. Krieger. Comparison of fetal rat limb bones and neonatal mouse calvaria: effects of parathyroid hormone and 1,25-dihydroxyvitamin $D_3$. Calcif. Tissue Int. 35: 172–176,1983). The calvaria model of bone resorption can be successfully used to screen osteotropic compounds as has been previously shown (Green, J. R., K. Muller and K. Jaeggi. Preclinical pharmacology of CGP 42'446, a new, potent, heterocyclic bisphosphonate compound. J. Bone Miner. Res. 9: 745–751, 1994.).

In one modification of the conventional calvaria model, calvaria are not labeled with $^{45}Ca^{++}$. Instead, calvarial calcium release into the media is assessed using a microtiter calorimetric calcium assay. This modification can yield more consistent responses than the radioactive methodology and provides results which are comparable to literature values for $^{45}Ca^{++}$ assays.

One calvaria culture model tests the ability of anti-resorptive compounds to prevent resorption (prophylactic model). A second model tests the ability of these compounds to terminate ongoing resorption (therapeutic model). Cytotoxicity may be assessed in both models using a lactate dehydrogenase (LDH) assay. These in vitro models of bone resorption may be used for routine screening and evaluation of compounds for their ability to alter osteoclast-mediated bone resorption.

Media Preparation

Calcium free Dulbecco's Modified Eagle's Medium (DMEM) may be obtained in a 5×solution (Specialty Media, D-012). A 1×solution is prepared using ultrafiltered water. A suitable media contains 15% heat inactivated horse serum (Sigma, H 1270). Calcium concentration is adjusted to 1.65 to 1.83 mM using 0.2 M $CaCl_2$. Penicillin (100 U/ml) and streptomycin (0.1 mg/ml) are added to the final media preparation. Indomethacin is prepared to 0.5 mg/ml ($1.397 \times 10^{-7}$ M) in ethanol, and is added to an aliquot of DMEM to produce a final concentration of 0.5 $\mu$M. Bovine parathyroid hormone (1–34) may be obtained from Bachem (PCAL 100). PTH is solubilized in 0.1% BSA and is then diluted in DMEM to produce a final concentration of $10^{-6}$ M PTH. Ten-fold serial dilutions are performed down to $10^{-11}$ M.

Calvaria Dissection

Pregnant CD-1 mice may be obtained from Charles River and are subjected to parturition. Neonatal mice (4–6 days) are cleansed with betadine and then euthanized by decapitation. Adherent skin is cleared away from the skull, exposing the calvaria. The calvaria are dissected away from the skull using a 12B scalpel. Calvaria are immediately placed into a glass petri dish containing room temperature Tyrode's Salt Solution (Sigma, T-2397). The calvaria are trimmed free of cartilage and bisected with a scalpel along the sagital suture. After dissection of all calvaria, calvaria are transferred into 24 well plates containing 0.5 $\mu$M indomethacin (Sigma, I-7378).

Culture Conditions

Calvaria are incubated in 1.5 ml DMEM in 24 well tissue culture plates at 37° C., 5% $CO_2$/air. Plates are rocked in the incubator using a Bellco rocker platform. Calvaria are pre-incubated in 0.5 $\mu$M indomethacin for 24 hours. For each experiment, 6 to 8 random calvaria halves are used for each group. Both halves from a single mouse are never in the same group. Experiments are repeated at least three times.

Prophylactic Calvaria Experiment

After the 24 h pre-incubation period, calvaria are thoroughly washed in indomethacin-free DMEM. Calvaria are then transferred to new wells containing various PTH concentrations, and are cultured for an additional 72 hours. Media samples (30 $\mu$l) are obtained every 24 hours and assayed for calcium and LDH activity.

Therapeutic Calvaria Experiment

At the end of the 24 h pre-incubation period, the calvaria are washed free of indomethacin using DMEM. Calvaria are then transferred to new wells containing DMEM or various concentrations of PTH. After 24 hours calvaria are transferred into new wells with fresh media (PTH or DMEM) and cultured an additional 48 hours before addition of control vehicle. This may be accomplished by adding 3 $\mu$l of DMSO to new wells, and transferring each calvaria along with its media into wells. Culture continues for a further 24 hours. Media samples are obtained after 72 hours and 96 hours in culture with PTH and assayed for calcium. Additional samples are obtained after 48, 72, and 96 hours in culture with PTH and assayed for LDH.

Calcium Assay

A commercially available diagnostic calcium assay (Sigma, No. 588-3), modified for use in a microtiter format, may be used to determine circulating serum calcium concentrations. This colorimetric assay is dependent on the specific, high affinity complexation of calcium with arsenazo III dye under acidic conditions, which occurs with 1:1 stoichiometry and absorbs at 600 nm (Bauer, P. J. Affinity and stoichiometry of calcium binding by Arsenazo III. Anal Biochem, 110:61, 1981; Michaylova, V and P Ilkova. Photometric determination of micro amounts of calcium with Arsenazo III. Anal Chim Acta, 53: 194, 1971). Magnesium has very low affinity for arsenazo III.

Briefly, 15 $\mu$l of media or rat sera (see below) is diluted 18-fold with ultrafiltered water (nearly calcium-free). Fifty $\mu$l of this solution are pipetted into microtiter wells (Nunc, Maxisorp, flat-bottom, 0.4 ml/well). Standards of 0, 0.5, 1, 2.5, 3.75, 5, 6.25, and 7.5 mg/dl (mg %) calcium, diluted 8-fold with ultrafiltered water from control standards (Sigma, 360-11), are used to construct standard curves. Once all standards and samples are pipetted onto the plate, 150 $\mu$l of diagnostic reagent is added to initiate complexation. Optical density measurements are obtained on a microtiter plate reader (Molecular Devices, ThermoMax) at 600 nm.

Lactate Dehydrogenase Assay

Phosphate buffer is prepared in distilled water (0.26 M $K_2HPO_4.3H_2O$, 0.26 M $KH_2PO_4$; pH 7.4). A mix consisting of: 22 ml of phosphate buffer, 6 ml distilled water and 2.0 ml of 0.01 M pyruvate is prepared. NADH is prepared to 0.4 mg/ml in phosphate buffer.

Ten $\mu$l of media samples obtained from incubated calvaria are added to 96 well plates. Wells containing 10 $\mu$l of DMEM serve as blanks. To each well, 90 $\mu$l distilled water and 150 $\mu$l phosphate mix is added. 50 $\mu$l NADH is added using an eight channel pipette immediately before the plate is read on a microtiter plate reader at 340 nm. A kinetic assay is performed for 10 minutes, with a read interval of 20 seconds.

Thyroid/Parathyroidectomized Rat Model of Bone Resorption

Parathyroid hormone (PTH) replacement in thyroparathyroidectomized (TPTX) rats is routinely used as an in vivo model of controlled bone resorption. Rats are the species of choice since the mechanisms of bone modeling in the rat resemble those in humans. In addition, hormones and pharmacologic agents have similar effects on both rat and human bone (Frost, H. M. and W. S. S. Jee. On the rat model of human osteopenias and osteoporoses. Bone and Mineral, 18: 227–236, 1992). Removal of the thyroid and parathyroid glands results in a rapid loss of parathyroid hormone (PTH)

from the circulation. Since PTH induces osteoclast-mediated bone resorption, this process is inhibited in TPTX animals. In addition, PTH mediates calcium reabsorption from the kidneys and absorption from the small intestines. The lack of these activities work in concert to decrease serum calcium levels. In the absence of PTH, rats remain in a hypocalcemic state. Restriction of dietary calcium limits intestinal calcium absorption and renal calcium filtration such that serum calcium levels are primarily influenced by bone resorption. Controlled PTH replacement therapy results in a controlled return of serum calcium to baseline levels. When replacement occurs, concomitantly with a low calcium diet, serum calcium increase is due to PTH-induced osteoclast-mediated bone resorption. In this model, drugs which inhibit bone resorption prevent the PTH-mediated return of serum calcium to baseline levels.

Female Wistar rats (226–250 gm, Charles River) are fasted overnight and anesthetized with 0.15 ml of 1.2% tribromoethanol (TBE). The ventral neck area is shaved and swabbed with betadine and isopropanol. A midline incision is made in the neck through the skin and superficial muscle layer, as well as in the sternohyoid muscle. Blunt dissection is performed to expose the thyroid gland. The thyroid gland is carefully isolated from the trachea, thyrohyoid muscle, as well as adjacent nerves and blood vessels, using blunt dissection. The thyroid gland is excised one lobe at a time. Cautery is performed for hemostasis. Care is taken to avoid damaging the recurrent laryngeal nerve since damage to it is shown to affect serum calcium concentrations (Hirsch, P. F., G. F. Gauthier and P. L. Munson. Thyroid hypocalcemic principle and recurrent laryngeal nerve injury as factors affecting the response to parathyroidectomy in rats. Endocrinology, 73: 244–252, 1963. et al., 1963). The incisions are closed using 3-0 vicryl. The wound is coated with triple antibiotic ointment (Fougera; 400 units/g bacitracin zinc, 5 mg/g neomycin sulfate, 5000 units/g polymyxin B sulfate). Following TPTX, rats are pair fed a low calcium diet (Harlan Teklad TD 95065; <0.003% $Ca^{++}$, <0.04% $PO_4$) such that each rat receives the same quantity of food. Rats are fed at least 5 grams, but not more than 10 grams, of food. Rats consuming less than 3.0 grams of food receive the nutritional supplement Nutri-Cal p.o. (Evsco; <0.0033% calcium).

PTH Dose Response/Pump Implantation

Three days post TPTX, rats which are found to be hypocalcemic, based on day 2 serum calcium levels, are implanted with PTH-containing Alzet mini-osmotic pumps (ALZA, model 2001D) which pumps at a rate of 1 µl/h. The rats are anesthetized with ketamine (50 mg/kg, i.p.) and acepromazine (1.67 mg/kg, i.p.). The scapula region is shaved and prepared for surgery with betadine and isopropanol. A lateral incision of approximately 2 cm in length is made between the scapulae. Using hemostats, a subcutaneous pocket is created into which the Alzet pump is inserted. The wound is closed either with nylon suture or with staples. Triple antibiotic ointment is applied as described previously.

Bovine parathyroid hormone 1–34 (PTH) (Bachem California, PCAL 100) is prepared in vehicle ($10^{-3}$ N HCl, 0.15 M NaCl, 20 mg/ml cysteine.HCl) at the following concentrations: 0.156, 0.47, 1.56, 4.7, 15.6, and 156 µM. Alzet mini-osmotic pumps are filled with the PTH solution and maintained in 37° C. saline for 4 hours prior to implantation.

Serum Samples

Rats are anesthetized by $CO_2$ from dry ice and daily blood samples are obtained via cardiac puncture using a 27 gauge needle. Baseline samples are taken just prior to TPTX. Daily samples are obtained in the morning. Samples are allowed to clot on their side for several hours and subsequently spun at 1000×g for 15 minutes to obtain serum. Serum is aliquoted and stored in the refrigerator until assayed for serum calcium. Serum calcium is measured (see above) daily for at least 7 days following TPTX.

Uses of Compounds of this Invention

Compounds of this invention which bind to an SH2 domain of interest may be used as biological reagents in assays as described herein for functional classification of a pTyr-binding domain (e.g. SH2 or PI domain) of a particular protein, particularly a newly discovered protein. Families or classes of such proteins which bind to pTyr-containing ligands may now be defined functionally, with respect to ligand specificity. Moreover, compounds of this invention can be used to inhibit the occurrence of biological events resulting from molecular interactions mediated by the protein of interest. Inhibiting such interactions can be useful in research aimed at better understanding the biology of events mediated by the binding of pTyr-containing ligands to their receptors.

Such compounds would be useful, for example, in the diagnosis, prevention or treatment of conditions or diseases resulting from a cellular processes mediated by the binding of a pTyr-containing ligand with a receptor therefor. For example, a patient can be treated to prevent the occurrence or progression of osteoporosis or to reverse its course by administering to the patient in need thereof an SH2inhibitor which selectively binds Src SH2 or otherwise interferes with Src-mediated signaling.

There are many other conditions for which such signal transduction inhibitors may be useful therapeutically, including, e.g., breast cancer where the SH2 domain-containing proteins Src, PLCgamma and Grb7 have been implicated. Other relevant conditions include prostate cancer, in which case targeting Grb2, PLCgamma, and PI3K, all of which contain SH2 domains, may be useful in treatment or prevention of the disease. Inhibition of the interaction of Grb2 or Abl SH2 domains with BCR-abl may be useful to treat chronic myelogenous leukemia (CML) or acute myelogenous leukemia (AML).

Still other relevant applications include the prevention of interferon-, growth factor-, or cytokine-mediated diseases (e.g. inflammatory diseases) by targeting the interaction of STAT proteins with their pTyr-containing ligands or otherwise inhibiting their signal transduction pathways. Agents that block the SH2 domains of ZAP-70 or otherwise inhibit ZAP-70-mediated signaling would be candidates for the treatment of immune-related disorders such as rejection of transplanted bone marrow, skin or other organs; rheumatoid arthritis; inflammatory bowel disease; and systemic lupus erythmatosis, and a variety of autoimmune diseases.

By virtue of the capacity to inhibit protein-protein interactions or a relevant kinase or phosphatase activity required for cellular events of pharmacologic importance, compounds of this invention which inhibit cellular signal transduction may be used in pharmaceutical compositions and methods for treatment or prevention in a subject in need thereof. Such inhibitors can be used to treat or reduce the risk of the diseases or their pathological effects mediated by such interactions.

For example, drugs that completely block one of the two ZAP SH2 domains should effectively prevent ZAP from associating with the activated TCR and thus block T cell activation. A ZAP antagonist or inhibitor would specifically inhibit T cells and avoid the toxicity of the currently used immunosuppressive drugs, FK506 and cyclosporin, which target the more ubiquitously expressed protein, calcineurin. Since calcineurin is required for cellular activities in several tissues in addition to T cells, cyclosporin and FK506 cause side effects in the kidney and central nervous system which limit their application largely to patients with organ transplant rejection.

Therapeutic/Prophylactic Administration & Pharmaceutical Compositions

Compounds of this invention can exist in free form or, where appropriate, in salt form. Pharmaceutically acceptable salts of many types of compounds and their preparation are well-known to those of skill in the art. The pharmaceutically acceptable salts of compounds of this invention include the conventional non-toxic salts or the quaternary ammonium salts of such compounds which are formed, for example, from inorganic or organic acids of bases.

The compounds of the invention may form hydrates or solvates. It is known to those of skill in the art that charged compounds form hydrated species when lyophilized with water, or form solvated species when concentrated in a solution with an appropriate organic solvent.

This invention also relates to pharmaceutical compositions comprising a therapeutically (or prophylactically) effective amount of the compound, and a pharmaceutically acceptable carrier or excipient. Carriers include e.g. saline, buffered saline, dextrose, water, glycerol, ethanol, and combinations thereof, and are discussed in greater detail below. The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Formulation may involve mixing, granulating and compressing or dissolving the ingredients as appropriate to the desired preparation.

The pharmaceutical carrier employed may be, for example, either a solid or liquid.

Illustrative solid carrier include lactose, terra alba, sucrose, talc, gelatin, agar, pectin, acacia, magnesium stearate, stearic acid and the like. A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions, and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Illustrative liquid carriers include syrup, peanut oil, olive oil, water, etc. Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl create and isopropyl myristate. Sterile liquid carders are useful in sterile liquid form compositions for parenteral administration. The liquid carrier for pressurized compositions can be halogenated hydrocarbon or other pharmaceutically acceptable propellant. Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

The carrier or excipient may include time delay material well known to the art, such as glyceryl monostearate or glyceryl distearate along or with a wax, ethylcellulose, hydroxypropylmethylcellulose, methylmethacrylate and the like. When formulated for oral administration, 0.01% Tween 80 in PHOSAL PG-50 (phospholipid concentrate with 1,2-propylene glycol, A. Nattermann & Cie. GmbH) has been recognized as providing an acceptable oral formulation for other compounds, and may be adapted to formulations for various compounds of this invention.

A wide variety of pharmaceutical forms can be employed. If a solid carrier is used, the preparation can be tableted, placed in a hard gelatin capsule in powder or pellet form or in the form of a troche or lozenge. The amount of solid carrier will vary widely but preferably will be from about 25 mg to about 1 g. If a liquid carrier is used, the preparation will be in the form of a syrup, emulsion, soft gelatin capsule, sterile injectable solution or suspension in an ampule or vial or nonaqueous liquid suspension.

To obtain a stable water soluble dosage form, a pharmaceutically acceptable salt of the compound may be dissolved in an aqueous solution of an organic or inorganic acid, such as a 0.3M solution of succinic acid or citric acid. Alternatively, acidic derivatives can be dissolved in suitable basic solutions. If a soluble salt form is not available, the compound is dissolved in a suitable cosolvent or combinations thereof. Examples of such suitable cosolvents include, but are not limited to, alcohol, propylene glycol, polyethylene glycol 300, polysorbate 80, glycerin, polyoxyethylated fatty acids, fatty alcohols or glycerin hydroxy fatty acids esters and the like in concentrations ranging from 0–60% of the total volume.

Various delivery systems are known and can be used to administer the compound, or the various formulations thereof, including tablets, capsules, injectable solutions, encapsulation in liposomes, microparticles, microcapsules, etc. Methods of introduction include but are not limited to dermal, intradermal, intramuscular, intraperitoneal, intravenous, subcutaneous, intranasal, pulmonary, epidural, ocular and (as is usually preferred) oral routes. The compound may be administered by any convenient or otherwise appropriate route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

For treatment or prophylaxis of nasal, bronchial or pulmonary conditions, preferred routes of administration are oral, nasal or via a bronchial aerosol or nebulizer.

In certain embodiments, it may be desirable to administer the compound locally to an area in need of treatment; this may be achieved by, for example, and not by way of limitation, local infusion during surgery, topical application, by injection, by means of a catheter, by means of a suppository, or by means of a skin patch or implant, said implant being of a porous, non-porous, or gelatinous material, including membranes, such as sialastic membranes, or fibers.

In a specific embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic to ease pain at the side of the injection. Generally, the ingredients are supplied either separately or mixed together in unit dosage form, for example, as a lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Administration to an individual of an effective amount of the compound can also be accomplished topically by administering the compound(s) directly to the affected area of the skin of the individual. For this purpose, the compound is administered or applied in a composition including a pharmacologically acceptable topical carrier, such as a gel, an ointment, a lotion, or a cream, which includes, without limitation, such carriers as water, glycerol, alcohol, propylene glycol, fatty alcohols, triglycerides, fatty acid esters, or mineral oils.

Other topical carriers include liquid petroleum, isopropyl palmitate, polyethylene glycol, ethanol (95%), polyoxyethylene monolaurate (5%) in water, or sodium lauryl sulfate (5%) in water. Other materials such as anti-oxidants, humectants, viscosity stabilizers, and similar agents may be added as necessary. Percutaneous penetration enhancers such as Azone may also be included.

In addition, in certain instances, it is expected that the compound may be disposed within devices placed upon, in, or under the skin. Such devices include patches, implants, and injections which release the compound into the skin, by either passive or active release mechanisms.

Materials and methods for producing the various formulations are well known in the art and may be adapted for practicing the subject invention. See e.g. U.S. Pat. Nos. 5,182,293 and 4,837,311 (tablets, capsules and other oral formulations as well as intravenous formulations) and European Patent Application Publication Nos. 0 649 659 (published Apr. 26, 1995; illustrative formulation for IV administration) and 0 648 494 (published Apr. 19, 1995; illustrative formulation for oral administration).

The effective dose of the compound will typically be in the range of about 0.01 to about 50 mg/kgs, preferably about 0.1 to about 10 mg/kg of mammalian body weight, administered in single or multiple doses. Generally, the compound may be administered to patients in need of such treatment in a daily dose range of about 1 to about 2000 mg per patient.

The amount of compound which will be effective in the treatment or prevention of a particular disorder or condition will depend in part on the nature and severity of the disorder or condition, which can be determined by standard clinical techniques. In addition, in vitro or in vivo assays may optionally be employed to help identify optimal dosage ranges. Effective doses may be extrapolated from dose-response curves derived from in vitro or animal model test systems. The precise dosage level should be determined by the attending physician or other health care provider and will depend upon well known factors, including route of administration, and the age, body weight, sex and general health of the individual; the nature, severity and clinical stage of the disease; the use (or not) of concomitant therapies.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceutical products, which notice reflects approval by the agency of manufacture, use or sale for human administration.

The representative examples which follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

In addition, the full contents of U.S. patent applications U.S. Ser. Nos. 08/968,490 and 09/190,424(Weigele et al, "Novel Signal Transduction Inhibitors, Compositions Containing Them & Uses Thereof" (filed Nov. 11, 1998 and Nov. 11, 1999, respectively) and WO 99/24442, as well as U.S. Ser. Nos. 60/078,412 and 60/108,084 (Buchanan et al, "Novel Signal Transduction Inhibitors, Compositions Containing Them & Uses Thereof", filed Mar. 18, 1998 and Nov. 12, 1998, respectively) and WO 99/47529 are incorporated by reference herein. Those documents provide additional synthetic and other guidance which may be of interest to the practitioner of the subject invention.

The following examples contain important additional information, exemplification and guidance which can be adapted to the practice of this invention in its various embodiments and the equivalents thereof.

EXAMPLES

Example 1

{4-[(S)-2-Acetylamino-2-(3-carbamoyl-2-gyclohexylmethoxy-6,7,8,9-tetrahydro-5H-benzocyclohepten-(S)-5-ylcarbamoyl)-ethyl]-phenoxy}-acetic acid

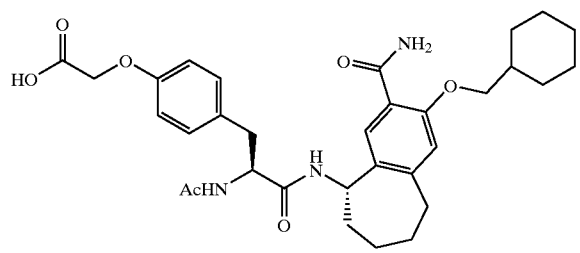

(a) 2-Cyclohexylmethoxy-6,7,8,9-tetrahydro-5H-benzocycloheptene

To a mixture of 6,7,8,9-tetrahydro-5H-benzocyclohepten-2-ol (Helvetica Chimica Acta 1947, 1883.) (9.9 g, 61.0 mmol) and $Cs_2CO_3$ (26.3 g, 73.2 mmol) in DMF (100 ML) was added (bromomethyl)cyclohexane (10.2 mL, 73.2 mmol). The mixture was heated to 60° C. for 18 h, dumped into water and extracted with ethyl acetate. The combined extracts were washed with water, dried over magnesium sulfate and concentrated to a solid. The solid was recrystallized from ethanol (13.0 g, 83%). m.p. 62–63° C.

(b) 2-Cyclohexylmethoxy-6,7,8,9-tetrahydro-benzocyclohepten-5-one

A mixture of 2-cyclohexylmethoxy-6,7,8,9-tetrahydro-5H-benzocycloheptene (0.50 g, 1.94 mmol), potassium persulfate (1.57 g, 5.82 mmol), copper(II) sulfate pentahydrate (0.48 g, 1.94 mmol) and $CH_3CN/H_2O$ (1:1, 13 mL) were heated at reflux for 45 min. After cooling the mixture was diluted with water and extracted with EtOAc. The combined extracts were washed with water, dried over magnesium sulfate, concentrated, and chomatographed over silica gel (20% EtOAc/hexane) to a white solid (0.46 g, 87%). MS $[M+H]^+$ 273, m.p. 86–88° C.

(c) 2-Cyclohexylmethoxy-6,7,8,9-tetrahydro-5H-benzocyclohepten-5-ol

To a suspension of 2-cyclohexylmethoxy-6,7,8,9-tetrahydro-benzocyclohepten-5-one (14.5 g, 53.23 mmol) in EtOH (150 mL) was added $NaBH_4$ (1.96 g, 53.23 mmol) portionwise over 10 min. The mixture was heated to 40° C. for 1 h, cooled to 0° C., then made acidic with the addition of 1 N HCl. The white precipated solids were filtered, washed with water, and dried in vacuuo (14.25 g, 97%). m.p. 102–103° C.

(d) 5-Azido-2-cyclohexylmethoxy-6,7,8,9-tetrahydro-5H-benzocycloheptene

To 2-cyclohexylmethoxy-6,7,8,9-tetrahydro-5H-benzocyclohepten-5-ol (14.2 g, 52.0 mmol) in toluene (100 mL) at 0° C. was added DBU (9.4 mL, 62.9 mmol) followed by diphenylphosphoryl azide (13.6 mL, 62.9 mmol). The mixture was allowed to stir for 18 h at rt, diluted with EtOAc, then washed successively with 1 N HCl, and water. The organic layer was dried over $MgSO_4$, filtered, concentrated, and chomatographed over silica gel (5% EtOAc/hexane) to yield a 7:3 mixture of 5-azido-2-cyclohexylmethoxy-6,7,8,9-tetrahydro-5H-benzocycloheptene/3-cyclohexylmethoxy-6,7-dihydro-5H-benzocycloheptene (12.6 g). This mixture was used without further purification in the next reaction.

(e) (2-Cyclohexylmethoxy-6,7,8,9-tetrahydro-5H-benzoclohepten-5-yl)-carbamic acid tert-butyl ester To the mixture from the preceeding reaction dissolved in EtOAc (150 mL) was added 10% Pd/C (500 mg) followed by $Boc_2O$ (5.61 g, 25 mmol). The mixture was hydrogenated at STP for 17 h, filtered though glass, concentrated, and chomatographed over silica gel to a white solid (7.93 g, 41% from (c)). MS $[M-H]^-$ 372, m.p. 125–126° C.

(f) (3-Bromo-2-cyclohexylmethoxy-6,7,8,9-tetrahydro-5H-benzocyclohepten-5-yl)-carbamic acid tert-butyl ester To (2-cyclohexylmethoxy-6,7,8,9-tetrahydro-5H-benzocyclohepten-5-yl)-carbamic acid tert-butyl ester (7.93 g, 21.2 mmol) in $CH_3CN$ (300 mL) was added NBS (3.96 g, 22.3 mmol). The mixture was stirred for 1.5 h, then blown dry under a stream of $N_2$. The residue was resuspended in $CCl_4$, filtered, and concentrated to a solid. The solid was recrystallized from $CH_3CN$ to yield a white solid (8.5 g, 88%). MS $[M-H]^-$ 452, m.p. 142–144° C.

(g) 9-tert-Butoxycarbonylamino-3-cyclohexylmethoxy-6,7,8,9-tetrahydro-5H-benzocycloheptene-2-carboxylic acid To (3-bromo-2-cyclohexylmethoxy-6,7,8,9-tetrahydro-5H-benzocyclohepten-5-yl)-carbamic acid tert-butyl ester (8.0 g, 17.7 mmol) in THF (100 mL) at −78° C. was added nBuLi (21.2 mL, 53.1 mmol, 2.5 M hexane) dropwise. The mixture was stirred for 10 min then a stream of $CO_2$ (g) was bubbled though the mixture for 2 min. The mixture was diluted with ether and water, warmed to rt and the layers seperated. The aqueous layer was extracted with $Et_2O$ and the combined extracts were washed with water, dried over magnesium sulfate, and concentrated to a solid. The solid was recrystallized from $Et_2O$ to yield a white solid (5.0 g, 68%). MS $[M-H]^-$ 416, m.p. 159–160° C.

(h) (3-Carbamoyl-2-cyclohexylmethoxy-6,7,8,9-tetrahydro-5H-benzocyclohepten-5-yl)-carbamic acid tert-butyl ester To 9-tert-butoxycarbonylamino-3-cyclohexylmethoxy-6,7,8,9-tetrahydro-5H-benzocycloheptene-2-carboxylic acid (1.5 g, 3.60 mmol) in $CH_2Cl_2$/DMF (4:1, 25 mL) was added HOBT (0.53 g, 4.0 mmol) and EDC (0.76 g, 4.0 mmol) and the mixture allowed to stir for 30 min. To this was added $NH_4OH$ (27% aqueous, 0.30 mL, 4.0 mmol) and stirring was continued for 3 h. The mixture was diluted with 1 M HCl and extracted with EtOAc. The combined extracts were washed with water, sat'd $NaHCO_3$, dried over magnesium sulfate,and concentrated to a solid. The solid was recrystallized from $Et_2O$ to yield a white solid (5.0 g, 68%). MS $[M-H]^-$ 415, m.p. 193–194° C.

(i) 9-Amino-3-cyclohexylmethoxy-6,7,8,9-tetrahydro-5H-benzocycloheptene-2-carboxylic acid amide To (3-carbamoyl-2-cyclohexylmethoxy-6,7,8,9-tetrahydro-5H-benzocyclohepten-5-yl)-carbamic acid tert-butyl ester (0.60 g, 144 mmol) in $CH_2Cl_2$ (8 mL) was added TFA (2 mL). The mixture was stirred for 1 h, evaporated under a stream of $N_2$, diluted with $CH_2Cl_2$ and washed with 1 N NaOH. The organic layer was dried over magnesium sulfate and concentrated to a tan solid (0.45 g, 99%). MS $[M+H]^+$ 316, m.p. 170–172° C.

(j) (R,S)-9-[(S)-2-Acetylamino-3-(4-hydroxy-phenyl)-propionylamino]-3-cyclohexylmethoxy-6,7,8,9-tetrahydro-5H-benzocycloheptene-2-carboxylic acid amide To N-acetyl-L-tyrosine (0.12 g, 0.55 mmol) in 5 mL of DME at 0° C. was added HOBT (0.083 g, 0.55 mmol), EDC (0.10 g, 0.55 mmol) and 9-amino-3-cyclohexylmethoxy-6,7,8,9-tetrahydro-5H-benzocycloheptene-2carboxylic acid amide (0.16 g, 0.50 mmol). The resulting solution was allowed to stir for 3 h. The clear, yellow solution was diluted with 75 mL of ethyl acetate and was washed with water, 1 N HCl, saturated $NaHCO_3$, saturated $NH_4Cl$ and brine. Drying over $MgSO_4$ and concentration yielded a white foamy solid (0.24 g, 92%). MS $[M+H]^+$ 521.

(k) {4-[(S)-2-Acetylamino-2-(3-carbamoyl-2-cyclohexylmethoxy-6,7,8,9-tetrahydro-5H-benzocyclohepten-(R,S)-5-ylcarbamoyl)-ethyl]-phenoxy}-acetic acid tert-butyl ester To (R,S)-9-[(S)-2-acetylamino-3-(4-hydroxy-phenyl)-propionylamino]-3-cyclohexylmethoxy-6,7,8,9-tetrahydro-5H-benzocycloheptene-2-carboxylic acid amide (0.10 g, 0.19 mmol) in DMF (2 mL) was added potassium carbonate (8.0 mg, 0.58 mmol) and tert-butyl bromoacetate (85 µL, 0.58 mmol). The suspension was stirred at room temperature under an atmosphere of $N_2$ for 48 hours, after which the solution was diluted with 25 mL ethyl acetate and washed with water, 1N HCl, and brine. Drying over $MgSO_4$ and concentration yielded the crude ester which was used without purification immediately in the next reaction.

(1) {4-[(S)-2-Acetylamino-2-(3-carbamoyl-2-cyclohexylmethoxy-6,7,8,9-tetrahydro-5H-benzocyclohepten-(R or S)-5-ylcarbamoyl)-ethyl]-phenoxy}-acetic acid To {4-[(S)-2-acetylamino-2-(3-carbamoyl-2-cyclohexylmethoxy-6,7,8,9-tetrahydro-5H-benzocyclohepten-(R,S)-5-ylcarbamoyl)-ethyl]-phenoxy}-acetic acid tert-butyl ester (crude from the preceeding reaction) in methylene chloride (2 mL) was added TFA (0.25 mL). The mixture was stirred for 20 min., evaporated to dryness, and dissolved in DMSO (2 mL). Purification by RP HPLC (CH$_3$CN/H$_2$O) and lyophylization yielded two isomers: Isomer 1 (S,S): white solid (9.6 mg, 8.5%). MS [M−H]$^+$ 580. Isomer 2 (S,R): white solid (34 mg, 7.7%). MS [M−H]$^+$ 580.

Example 2

Phosphoric acid mono-{4-[(S)-2-acetylamino-2-(3-carbamoyl-2-cyclohexylmethoxy-6,7,8,9-tetrahydro-5H-benzocyclohepten-(R,S)-5-ylcarbamoyl)-ethyl]-phenyl}ester

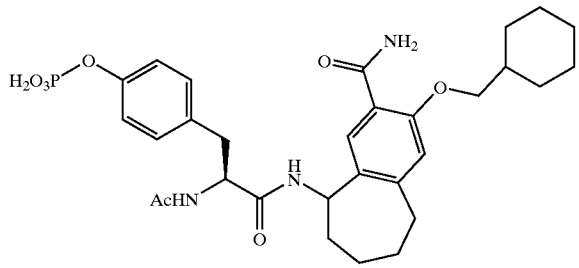

(a) Phosphoric acid 4-[(S)-2-acetylamino-2-(3-carbamoyl-2-cyclohexylmethoxy-6,7,8,9-tetrahydro-5H-benzocyclohepten-(R,S)-5-ylcarbamoyl)-ethyl-phenyl ester dibenzyl ester To (S)-9-[(S)-2-acetylamino-3-(4-hydroxy-phenyl)-propionylamino]-3-cyclohexylmethoxy-6,7,8,9-tetrahydro-5H-benzocyclohepten-2-carboxylic acid amide (0.13 g, 0.24 mmol) in CH$_3$CN at −20° C. were added in succession DIEA (0.10 mL, 0.57 mmol), CCl$_4$ (0.15 mL, 1.55 mmol), DMAP (3.7 mg, 0.030 mmol), and dibenzylphosphite (0.10 mL, 0.45 mmol). The mixture was stirred for 3 h, diluted with water, and extracted with EtOAc. The combined extracts were washed with water, 1 N HCl, sat'd NaHCO$_3$, dried over NaSO$_4$, concentrated, and chomatographed over silica gel (5% MeOH/CH$_2$Cl$_2$) to give a semi-solid (0.12 g, 65%). MS [M+H]$^+$ 782.

(b) Phosphoric acid mono-{4-[(S)-2-acetylamino-2-(3-carbamoyl-2-cyclohexylmethoxy-6,7,8,9-tetrahydro-5H-benzocyclohepten-(R,S)-5-ylcarbamoyl)-ethyl]-phenyl}ester To phosphoric acid 4-[(S)-2-acetylamino-2-(3-carbamoyl-2-cyclohexylmethoxy-6,7,8,9-tetrahydro-5H-benzocyclohepten-(R,S)-5-ylcarbamoyl)-ethyl]-phenyl ester dibenzyl ester (0.12 g, 0.16 mmol) in EtOH (5 mL) was added 20% Pd/C (100 mg). The mixture was hydrogenated at STP for 2 h. The mixture was filtered though glass, concentrated and purified by RP HPLC (CH$_3$CN/H$_2$O). Lyophylization yielded a white solid (70 mg, 97%). MS [M−H]$^+$ 602.

Example 3

({4-[(S)-2-Acetylamino-2-(3-carbamoyl-2-cyclohexylmethoxy-6,7,8,9-tetrahydro-5H-benzocyclohepten-(R or S)-5-ylcarbamoyl)-ethyl] phenyl}-difluoro-methyl)-phosphonic acid

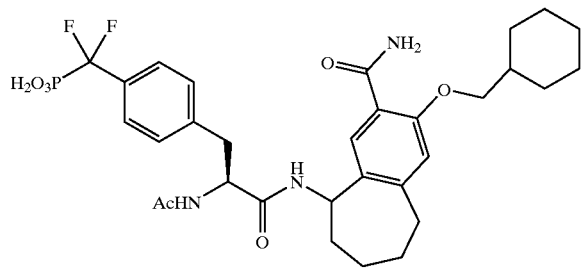

(a) ({4-[(S)-2-Acetylamino-2-(3-carbamoyl-2-cyclohexylmethoxy-6,7,8,9-tetrahydro-5H-benzocyclohepten-(R or S)-5-ylcarbamoyl)-ethyl]-phenyl}-difluoro-methyl)-phosphonic acid diethyl ester To (S)-2-acetylamino-3-{4-[(diethoxy-phosphoryl)-difluoro-methyl]-phenyl}-propionic acid (Tetrahedron Lett. 1993, 34, 4125) (0.14 g, 0.38 mmol) in CH$_2$Cl$_2$/DMF (4:1, 4 mL) at 0° C. was added HOBT (0.063 g, 0.46 mmol) and EDC (0.085 g, 0.44 mmol). To this was added 9-amino-3-Cyclohexylmethoxy-6,7,8,9-tetrahydro-5H-benzocycloheptene-2-carboxylic acid amide (0.11 g, 0.38 mmol) and stirring was continued for 1 h. The mixture was then diluted with EtOAc (70 mL), washed with 1 N HCl, sat'd NaHCO$_3$, sat'd NH$_4$Cl, and brine. The organic layer was dried over MgSO$_4$, filtered, and concentrated to a foamy solid (0.19 g, 84%). Purification by RP HPLC (CH$_3$CN/H$_2$O) and lyophylization yielded two isomers: Isomer 1: white solid (52 mg, 20%). MS [M−H]$^+$ 668. Isomer 2: white solid (90 mg, 36%). MS [M−H]$^+$ 668.

(b) ({4-[(S)-2-Acetylamino-2-(3-carbamoyl-2-cyclohexylmethoxy-6,7,8,9-tetrahydro-5H-benzocyclohepten-(S)-5-ylcarbamoyl)-ethyl]-phenyl}-difluoro-methyl)-phosphonic acid To Isomer 1 (preceeding reaction) (53 mg, 0.079 mmol) in CH$_3$CN (3 mL) cooled to −20° C. was added TMSI (0.15 mL, 1.0 mmol). The mixture was stirred for 20 min, quenched with sat'd NaHCO$_3$ (5 mL), and purified by RP HPLC (CH$_3$CN/H$_2$O) to a white solid (39.4 mg, 78%). MS [M−H]$^+$ 636.

(c) ({4-[(S)-2-Acetylamino-2-(3-carbamoyl-2-cyclohexylmethoxy-6,7,8,9-tetrahydro-5H-benzocyclohepten-(R)-5-ylcarbamoyl)-ethyl]-phenyl}-difluoro-methyl)-phosphonic acid Was made as for Isomer 1 (example 3, (b)). (62.3 mg, 70%). MS [M−H]$^+$ 636.

Example 4

({4-[(S)-2-Acetylamino-2-(3-carbamoyl-2-cyclohexylmethoxy-6,7,8,9-tetrahydro-5H-benzocyclohepten-(S and R)-5-ylcarbamoyl)-ethyl]-phenyl}-phosphono-methyl)-phosphonic acid

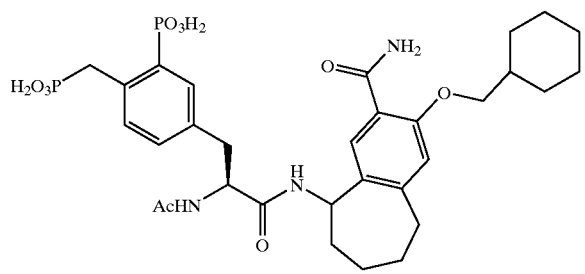

(a) p(CH$_2$PO$_3$Et$_2$)-L-Phe-OH

Fmoc-p(CH$_2$PO$_3$Et$_2$)-L-Phe-OH (5.0 g, 9.3 mmol) was dissolved in 170 mL of THF and 50 mL of diethyl amine and the mixture was vigorously stirred at rt for 3 h. Solvents were removed under reduced pressure and the solid was resuspended in anhydrous ether, filtered, and dried on high vacuum to afford 2.8 g (94%) of p(CH$_2$PO$_3$Et$_2$)-L-Phe-OH as white solid which was used without purification in the next step.

(b) N-Boe-p(CH$_2$PO$_3$Et$_2$)-L-Phe-OH

To a solution of p(CH$_2$PO$_3$Et$_2$)-L-Phe-OH (5.0 g, 16.7 mmol) in a 1:1 mixture of DME/water (140 ml) at 0° C. was added NaHCO$_3$ (3.1 g, 36.8 mmol) followed by Boc2O (4.0 g, 18.4 mmol). The mixture was stirred at 0° C. for 30 min then warmed to rt and stirred for 1 h. About 50 ml of DME was removed by evaporation then the remaining aqueous solution was extracted with EtOAc (2×50 mL). The aqueous layer was brought to pH 4 with 1 N HCl and extracted with EtOAc (3×100 mL). The combined extracts (second) were washed with water, dried over MgSO$_4$, filtered and concentrated to a colorless oil (6.2 g, 90%). MS [M−H]$^-$ 414.

(c) N-Boc-p(CH$_2$PO$_3$Et$_2$)-L-Phe-OMe

To a solution of N-Boc-p(CH$_2$PO$_3$Et$_2$)-L-Phe-OH (5.1 g, 12.2 mmol) in DMF (60 mL) was added Cs$_2$CO$_3$ (4.8 g, 14.7 mmol) followed by MeI (0.76 ml, 12.2 mmol). The mixture was stirred for 1 h, diluted with water (600 ml) and extracted with EtOAc (3×100 mL). The combined extracts were washed with water, 10% NaHSO$_3$, dried over MgSO$_4$, filtered and concentrated to a solid which was recrystallized from EtOAc/hexane to give a white solid (4.6 g, 88%). MS [M−H]$^-$ 428. m.p. 104–105° C.

(d) N-Boc-p[CH(PO$_3$Et$_2$)$_2$]-L-Phe-OMe

To a suspension of N-Boc-p(CH$_2$PO$_3$Et$_2$)-L-Phe-OMe (7.0 g, 16.3 mmol) in 185 mL of anhydrous DME, purged with N$_2$ and cooled to −42° C. (CH$_3$CN/dry ice), was added dropwise lithium bis(trimethylsilyl)amide (1 M THF, 48.9 mL, 48.9 mmol). The reaction mixture was stirred at −42° C. for 15 min. Diethylchlorophosphate (4.7 mL, 32.6 mmol) was added and the orange solution was stirred at −42° C. for an additional 20 min before being quenched with 1 N HCl (20 ml). The mixture was further diluted with water and extracted with EtOAc (3×100 mL). The combined extracts were washed with water, dried over MgSO$_4$, filtered, concentrated, and chomatographed over silica gel (3% MeOH/CH$_2$Cl$_2$) to give a colorless oil (6.0 g, 65%). MS [M−H]$^-$ 564.

(e) N-Boc-p[CH(PO$_3$Et$_2$)$_2$]-L-Phe-OH

To a solution of N-Boc-p[CH(PO$_3$Et$_2$)$_2$]-L-Phe-OMe (0.49 g, 0.966 mmol) in 5 mL of THF cooled to 0° C. was added dropwise a solution of lithium hydroxide monohydrate (49.0 mg, 1.17 mmol) in 1.0 mL of water. The reaction mixture was stirred at 0° C. for 1 h. THF was removed under reduced pressure to a yellow oil which was diluted with 10 mL of 1 N HCl. The aqueous phase was extracted with CH$_2$Cl$_2$ (8×15 mL), and the extracts were combined, dried over Na$_2$SO$_4$, and concentrated to afford 0.45 g (95%) of N-Boc-p[CH(PO$_3$Et$_2$)$_2$]-L-Phe-OH as a crystalline white solid. MS [M−H]$^-$ 550. m.p. 84–87° C.

(f) [{4-[(S)-2-tert-Butoxycarbonylamino-2-(3-carbamoyl-2-cyclohexylmethoxy-6,7,8,9-tetrahydro-5H-benzcyclohepten-(R,S)-5-ylcarbamoyl)-ethyl]-phenyl}-(diethoxy-phosphoryl)-methyl]-phosphonic acid diethyl ester To N-Boc-p[CH(PO$_3$Et$_2$)$_2$]-L-Phe-OH (0.22 g, 0.41 mmol) in CH$_2$Cl$_2$/DMF (4:1, 4 mL) at 0° C. was added HOBT (0.066 g, 02.9 mmol) and EDC (0.092 g, 0.48 mmol). To this was added 9-amino-3-cyclohexylmethoxy-6,7,8,9-tetrahydro-5H-benzocycloheptene-2-carboxylic acid amide (0.12 g, 0.38 mmol) and stirring was continued for 1 h. The mixture was then diluted with EtOAc (70 mL), washed with 1 N HCl, sat'd NaHCO$_3$, sat'd NH$_4$Cl, and brine. The organic layer was dried over MgSO$_4$, filtered, and concentrated to a foamy solid (0.29 g, 90%). This material was used without further purification in the next step.

(g) [{4-[(S)-2-Amino-2-(3-carbamoyl-2-cyclohexylmethoxy-6,7,8,9-tetrahydro-5H-benzocyclohepten-(R,S)-5-ylcarbamoyl)-ethyl]-phenyl}-(diethoxy-phosphoryl)-methyl]-phosphonic acid diethyl ester To the crude material from the preceeding reaction (0.29 g, 0.34 mmol) in CH$_2$Cl$_2$ (10 mL) was added HBFA (2 mL). The mixture was stirred for 30 min, evaporated to dryness and purified by RP HPLC (CH$_3$CN/H$_2$O): Isomer 1: white solid (143 mg, 50%). MS [M−H]$^+$ 750. Isomer 2: white solid (88 mg, 31%). MS [M−H]$^+$ 750.

(h) [{4-[(S)-2-Acetylamino-2-(3-carbamoyl-2-cyclohexylmethoxy-6,7,8,9-tetrahydro-5H-benzocyclohepten-(S)-5-ylcarbamoyl)-ethyl]-phenyl}-(diethoxy-phosphoryl)-methyl]-phosphonic acid diethyl ester To Isomer 1 (from the preceeding reaction) (0.14 g, 0.19 mmol) in CH$_2$Cl$_2$ (2 mL) at 0° C. was added TEA (0.30 mL, 2.15 mmol) followed by Ac$_2$O (0.075 mL, 0.80 mmol). The mixture was stirred for 30 min, diluted with CH$_2$Cl$_2$, and washed with 1 N HCl, sat'd NaHCO$_3$, and sat'd NH$_4$Cl. The organic layer was dried over MgSO$_4$, filtered and concentrated to a glassy solid (79.2 mg, 53%). This material (which was homogeneous by HPLC) was used without purification in the next reaction.

(i) ({4-[(S)-2-Acetylamino-2-(3-carbamoyl-2-cyclohexylmethoxy-6,7,8,9-tetrahydro-5H-benzocyclohepten-(S)-5-ylcarbamoyl)-ethyl]-phenyl}-phosphono-methyl)-phosphonic acid To [{4-[(S)-2-acetylamino-2-(3-carbamoyl-2-cyclohexylmethoxy-6,7,8,9-tetrahydro-5H-benzocyclohepten-(S)-5-ylcarbamoyl)-ethyl]-phenyl}-(diethoxy-phosphoryl)-methyl]-phosphonic acid diethyl ester (0.079 g, 0.10 mmol) in CH$_3$CN at 0° C. was added TMSI. The mixture was stirred for 30 min, quenched with sat'd NaHCO$_3$ (5 mL) and purified by RP HPLC (CH$_3$CN/H$_2$O) to a white solid (61.2 mg, 90%). MS [M−H]$^+$ 680.

(j) ({4-[(S)-2-Acetylamino-2-(3-carbamoyl-2-cyclohexylmethoxy-6,7,8,9-tetrahydro-5H-benzocyclohepten-(R)-5-ylcarbamoyl)-ethyl]-phenyl}-phosphono-methyl)-phosphonic acid Was made as for Isomer 1 (example 4, (steps h and i)). (62.3 mg, 70%). MS [M−H]$^+$ 680.

Example 5

4-[(S)-2-Acetylamino-2-(3-carbamoyl-2-cyclohexylmethoxy-6,7,8,9-tetrahydro-5H-benzocyclohepten-(S)-5-ylcarbamoyl)-ethyl]-2-formyl-benzoic acid

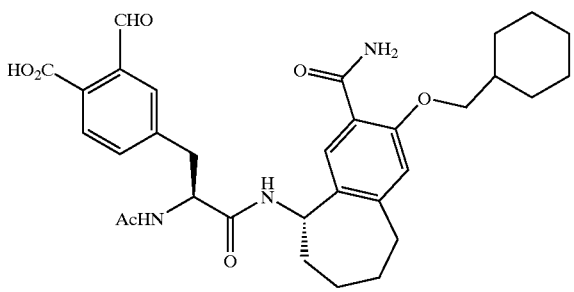

(a) 3-(1,3-Dithiolan-2-yl)-N-acetyl-L-tyrosine methyl ester

To L-3-formyl-N-acetyltyrosine methyl ester (U.S. Pat. No. 4,022,910) (0.13 g, 0.48 mmol) in methylene chloride (5 mL) at 0° C. was added boron trifluoride diethyl etherate (0.12 mL, 0.96 mmol) followed by ethanedithiol (0.044 mL, 0.53 mmol). The mixture was allowed to warm to rt and stirred for 1 h. The solution was dumped into water and the layers separated. The aqueous layer was extracted with methylene chloride and the combined extracts were washed with water, dried over magnesium sulfate and concentrated to a solid. The solid was recrystallized from ethyl acetate/hexane (0.14 g, 82%). m.p. 97–99° C.

(b) 3-(1,3-Dithiolan-2-yl)-4-(trifluoromethansulfonyloxy)-N-acetyl-L-phenylalanine methyl ester To 3-(1,3-dithiolan-2-yl)-N-acetyltyrosine methyl ester (0.50 g, 1.46 mmol) and triethylamine (0.22 mL, 1.61 mmol) in methylene chloride (10 mL) at 0° C. was added N-phenyltrifluoromethanesulfonimide (0.58 g, 1.61 mmol). The mixture was allowed to stir for five days then washed sequentially with 1 N NaOH, 1 N HCl, and brine. The organic layer was dried over magnesium sulfate and concentrated to a solid. The solid was recrystallized from ethyl acetate/hexane (0.61 g, 87%). m.p. 116–118° C.

(c) 3-(1,3-Dithiolan-2-yl)-4-(carboxymethyl)-N-acetyl-L-phenylalanine methyl ester To 3-(1,3-dithiolan-2-y)-4(trifluoromethansulfonyloxy)-N-acetyl-L-phenylalanine methyl ester (0.51 g, 1.08 mmol) in DMSO/MeOH (3:2, 5 mL) was added triethylamine (0.33 mL, 2.36 mmol) followed by palladium acetate (0.0073 g, 0.033 mmol) and 1,3-bis(diphenylphosphino)propane (0.013 g, 0.034 mmol). Carbon monoxide was bubbled though for 3 min and the mixture was heated to 80° C. for 24 hours. After cooling, the solution was diluted with water and extracted with ethyl acetate. The combined extracts were washed with water, dried over magnesium sulfate and concentrated to a solid. The solid was recrystallized from ethyl acetate/hexane (0.30 g, 72%). m.p. 113–119° C.

(d) 3-(1,3-Dithiolan-2-yl)-4-(carboxymethyl)-N-acetyl-L-phenylalanine

To 3-(1,3-dithiolan-2-yl)-4(carboxymethyl)-N-acetyl-L-phenylalanine methyl ester (0.22 g, 0.57 mmol) in THF (10 mL) at 0° C. was added lithium hydroxide monohydrate (0.025 g, 0.60 mmol, 1 mL water). The mixture was stirred for 45 min, diluted with water, made acidic with 1 N HCl, and extracted with ethyl acetate. The combined extracts were washed with water, dried over magnesium sulfate and concentrated to a glassy solid which was homogeneous by RP HPLC (0.18 g, 86%). MS [M–H]⁻ 368.

(e) 4[(S)-2-Acetylamino-2-(3-carbamoyl-2-cyclohexylmethoxy-6,7,8,9-tetrahydro-5H-benzocyclohepten-(R,S)-5-ylcarbamoyl)-ethyl]-2-[1,3]dithiolan-2-yl-benzoic acid methyl ester To 3-(1,3-dithiolan-2-yl)-4carboxymethyl)-N-acetyl-L-phenylalanine (0.13 g, 0.35 mmol) in CH₂Cl₂/DMF (5:1, 5 mL) at 0° C. was added HOBT (0.051 g, 0.35 mmol) and EDC (0.072 g, 0.35 mmol). The mixture was stirred for 10 min then (R,S)-9-amino-3-cyclohexylmethoxy-6,7,8,9-tetrahydro-5H-benzocycloheptene-2-carboxylic acid amide (0.10 g, 0.32 mmol) was added and stirring was continued for 1 h. The solution was dumped into water and the layers separated. The aqueous layer was extracted with methylene chloride and the combined extracts were washed with water, 1N HCl, dried over magnesium sulfate, and concentrated to a glassy solid (0.20 g, 99%) which was homogeneous by RP HPLC. MS [M–H]⁻ 636.

(f) 4-[(S)-2-Acetylamino-2-(3-carbamoyl-2-cyclohexylmethoxy-6,7,8,9-tetrahydro-5H-benzocyclohepten-(R,S)-5-ylcarbamoyl-ethyl]-2-formyl-benzoic acid methyl ester To 4-[(S)-2-acetylamino-2-(3-carbamoyl-2-cyclohexylmethoxy-6,7,8,9-tetrahydro-5H-benzocyclohepten-(R,S)-5-ylcarbamoyl)-ethyl]-2-[1,3]dithiolan-2-yl-benzoic acid methyl ester (0.20 g, 0.31 mmol) in CHCl₃/MeOH (1:1, 6 mL) was added mercury (II) perchlorate hydrate (0.38 g, 0.94 mmol). The mixture was stirred for 5 min then filtered though Celite (CHCl₃ wash). The organic layer was washed with 1 N HCl, saturated NaHCO₃, dried over magnesium sulfate, filtered, and concentrated to a glassy solid (0.18 g) which was used immediately in the next reaction.

(g) 4-[(S)-2-Acetylamino-2-(3-carbamoyl-2-cyclohexylmethoxy-6,7,8,9-tetrahydro-5H-benzocyclohepten-(S)-5-ylcarbamoyl)-ethyl]-2-formyl-benzoic acid To 4-[(S)-2-acetylamino-2-(3carbamoyl-2-cyclohexylmethoxy-6,7,8,9-tetrahydro-5H-benzocyclohepten-(R,S)-5-ylcarbamoyl)-ethyl]-2-formyl-benzoic acid methyl ester (0.18 g, 0.32 mmol) in THF (5 mL) was added lithium hydroxide monohydrate (0.018 g, 0.42 mmol, 1 mL water). The mixture was stirred for 1 h, acidified with TFA, and evaporated. The residue was diluted with DMSO (2 mL) and purified by RP HPLC (CH₃CN/H₂O). Lyophilization left a white solid (0.040 mg, 21%). MS [M–H]⁻ 576.

Example 6

{4-[(S)-2-Acetylamino-2-(3-carbamoyl-2-cyclohexylmethoxy-6,7,8,9-tetrahydro-5H-benzocyclohepten-(S)-5-ylcarbamoyl)-ethyl]-2-phosphono-phenyl}-phosphonic acid

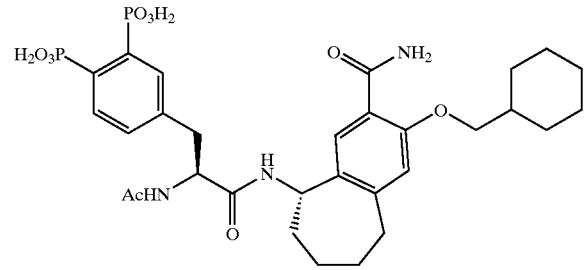

(a) 2-tert-Butoxycarbonylamino-3-(3,4-dihydroxy-phenyl)-propionic acid methyl ester To (3,4-dihydroxyphenyl)-L-alanine methyl ester hydrochloride (5.4 g, 25.4 mmol) and Di-tert-butyl dicarbonate (5.5 g, 25.4 mmol) in a mixture of THF (20 mL) and water (20 mL) at rt was added sodium bicarbonate (3.2 g, 38.1 mmol). The mixture was allowed to stirred for 16 h then washed with water, and extracted with EtOAc. The organic layer was dried over magnesium sulfate, and concentrated to a solid. The solid was recrystallized frome ethyl acetate/hexane (7 g, 88%). MS [M+H]⁺ 312. m.p. 132–135° C.

(b) 3-(3,4-Bis-trifluoromethanesulfonyloxy-phenyl)-2-tert-butoxycarbonylamino-propionic acid methyl ester To 2-tert-Butoxycarbonylamino-3-(3,4-dihydroxy-phenyl)-propionic acid methyl ester (12 g, 38.6 mmol) and triethyl amine (13 mL, 88.7 mmol) in methylene chloride (100 mL) at 0° C. was added N-phenyl-bis(trifluoromethanesulfonimide) (31.6 g, 88.7 mmol). The mixture was allowed to stirred for two days then washed sequentially with 1 N NaOH, 1 N HCl, and brine. The organic layer was dried over magnesium sulfate, concentrated to a solid. The solid was recrystallized from dichloremethane/hexane. MS [M+Na]+ 598. m.p. 80–82° C.

(c) 3-[3,4-Bis-(dietho-phosphoryl)-phenyl]-2-tert-butoxycarbonylamino-propionic acid methyl ester To 3-(3,4-bis-trifluoromethanesulfonyloxy-phenyl)-2-tert-butoxycarbonylamino-propionic acid methyl ester (2 g, 3.47 mmol), diethyl phosphite (1 mL, 7.65 mmol) and 4-methyl morpholine (0.93 mL, 8.3 mmol) in MeCN (10 ml) was added Pd(PPh$_3$)$_4$ (167 mg, 0.15 mmol). The mixture was allowed to stirred for two days at 95° C. then diluted with saturated NH$_4$Cl and extracted with EtOAc. The organic layer was dried over magnesium sulfate, concentrated, and chomatographed over silica gel (5% MeOH/EtOAc) to an oil (0.2 g, 37% yield). MS [M+H]+ 552 & [M+Na] 574.

(d) 3-[3,4-Bis-(diethoxy-phosphoryl)-phenyl]-2-tert-butoxycarbonylamino-propionic acid To a solution of 3-[3,4-Bis-(diethoxy-phosphoryl)-phenyl]-2-tert-butoxycarbonylamino-propionic acid methyl ester (110 mg, 0.2 mmol) in 5 mL of THF cooled to 0° C. was added dropwise a solution of lithium hydroxide monohydrate (8.5 mg, 0.2 mmol) in 1.0 mL of water. The reaction mixture was stirred at 0° C. for 1 h. THF was removed under reduced pressure to a yellow oil which was diluted with 10 mL of 1 N HCl. The aqueous phase was extracted with CH$_2$Cl$_2$ (2×15 mL), and the extracts were combined, dried over Na$_2$SO$_4$, and concentrated to afford an oil 107 mg (100%). MS [M-H]− 537.

(f) [4-[(S)-2-Amino-2-(3-carbamoyl-2-cyclohexylmethoxy-6,7,8,9-tetrahydro-5H-benzocyclohepten-(S)-5-ylcarbamoyl)-ethyl]-2-(diethoxy-phosphoryl)-phenyl]-phosphonic acid diethyl ester To 3-(S)-[3,4-bis-(diethoxy-phosphoryl)-phenyl]-2-(2,2-dimethyl-propionylamino)-propionic acid (107 mg, 0.19 mmol) in a mixture of methylene chloride/DMF (5:1, 10 mL) at 0° C. was added HOBt (27 mg, 0.2 mmol) and EDC (27 mg, 0.2 mmol). The mixture was stirred for 10 min then (R,S)-9-amino-3-cyclohexylmethoxy-6,7,8,9-tetrahydro-5H-benzocycloheptene-2-carboxylic acid amide (63 mg, 0.19 mmol) was added and stirring was continued for 1 h. The solution was dumped into water and the layers separated. The aqueous layer was extracted with methylene chloride and the combined extracts were washed with water, dried over magnesium sulfate and concentrated to a glassy solid. This crude material was dissolved in methylene chloride (10 mL) and 95% aqueous TEFA (2 mL). The solution was stirred for 1 h and then concentrated under a stream of N$_2$. The residue was purified by preparative RP HPLC. Elution with 40:60 MeCN—H$_2$O (each containing 0.1% TFA) provided the 60 mg of the title compound. MS [M+H]+ 736.

(g) [4-[(S)-2-Acetylamino-2-(3-carbamoyl-2-cyclohexylmethoxy-6,7,8,9-tetrahydro-5H-benzocyclohepten-(S)-5-ylcarbamoyl)-ethyl]-2-(diethoxy-phosphoryl)-phenyl]-phosphonic acid diethyl ester To [4-[(S)-2-amino-2-(3carbamoyl-2-cyclohexylmethoxy-6,7,8,9-tetrahydro-5H-benzocyclohepten-(S)-5-ylcarbamoyl)-ethyl]-2-(diethoxy-phosphoryl)-phenyl]-phosphonic acid diethyl ester (60 mg, 0.08 mmol) and triethyl amine (0.1 mL, 0.8 mmol) in methylene chloride (10 mL) at 0° C. was added acetic anhydride (0.03 mL, 0.32 mmol). The mixture was allowed to stirred for 1 h then diluted with water and extracted with EtOAc. The combined extracts were dried over magnesium sulfate and concentrated to a oil which was homogeneous by RP HPLC (65 mg, crude).

(h) {4-[(S)-2-Acetylamino-2-(3-carbamoyl-2-cyclohexylmethoxy-6,7,8,9-tetrahydro-5H-benzocyclohepten-(S)-5-ylcarbamoyl)-ethyl]-2-phosphono-phenyl}-phosphonic acid To a solution of [4-[(S)-2-acetylamino-2-(3-carbamoyl-2-cyclohexylmethoxy-6,7,8,9-tetrahydro-5H-benzocyclohepten-(S)-5-ylcarbamoyl)-ethyl]-2-(diethoxy-phosphoryl)-phenyl]-phosphonic acid diethyl ester (65 mg, 0.12 mmol) in MeCN (5 mL) at −11° C. was added TMSI (0.2 mL, 1.6 mmol). The mixture was stirred for 3 h at −11° C. and then quenched by saturated NaHCO$_3$ (1 mL). The resulting mixture was purified by RP HPLC (CH$_3$CN/H$_2$O). Lyophilization left a white soild. MS [M-H]− 664.

Example 7

{4-[(S)-2-Amino-2-(3-carbamoyl-2-cyclohexylmethoxy-6,7,8,9-tetrahydro-5H-benzocyclohepten-(R or S)-5-ylcarbamoyl)-ethyl]-2-phosphono-phenyl}-phosphonic acid

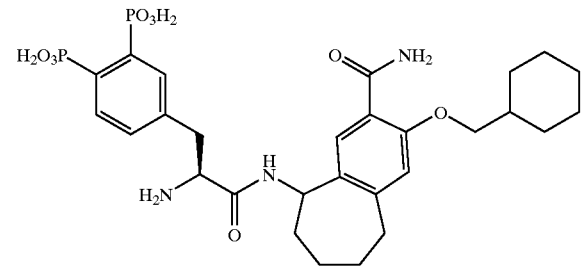

The title compounds were made from intermediates in the synthesis of example 6. MS [M-H]− 622.

Example 8

({4-[(S)-2-Acetylamino-2-(7-carbamoyl-8-cyclohexylmethoxy-2,3,4,5-tetrahydro-benzo[b] oxepin-(S)-5-ylcarbamoyl)-ethyl]-phenyl}-phosphono-methyl)-phosphonic acid

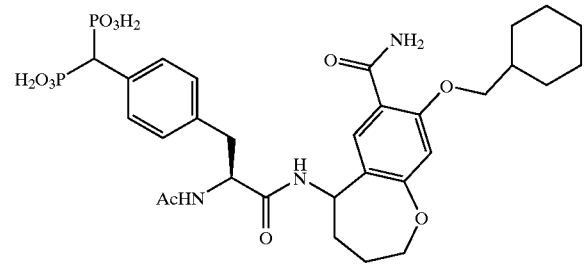

(a) 4-(4-Carbamoyl-3-hydroxy-phenoxy)-butyric acid ethyl ester

To 2,4-dihydroxybenzamide (16.5 g, 108.3 mmol) in DMF (100 mL) was added Cs$_2$CO$_3$ (39.0 g, 119.1 mmol) followed by ethyl 4-bromobutyrate (17.0 mL, 119.1 mmol). The mixture was heated to 70° C. for 2 h, cooled, diluted with water and extracted with EtOAc. The combined extracts were washed with water, dried over magnesium sulfate, concentrated, and chomatographed over silica gel (60% EtOAc/hexane) to a white solid (4.2 g, 15%). MS [M+H]− 267.

(b) 4-(4-Carbamoyl-3-cyclohexylmethoxy-phenoxy)-butyric acid ethyl ester

To 4-(4-carbamoyl-3-hydroxy-phenoxy)-butyric acid ethyl ester (3.0 g, 11.22 mmol) in DMF (25 mL) was added Cs₂CO₃ (5.11 g, 15.71 mmol) followed by (bromomethyl)cyclohexane (1.72 mL, 12.34 mmol). The mixture was heated to 60° C. for 6 h, then dumped onto ice/H₂O. The formed solids were collected by filtration (H₂O wash)and dried in vacuuo (3.74 g, 92%). MS [M+H]⁺ 364. m.p. 98–99° C.

(c) 444-Carbamoyl-3-cyclohexylmethoxy-phenoxy)-butyric acid

To 4-(4-carbamoyl-3-cyclohexylmethoxy-phenoxy)-butyric acid ethyl ester (3.74 g, 10.29 mmol) in THF (20 mL) was added LiOH·H₂O (0.61 g, 14.4 mmol) and H₂O (6 mL). The mixture was stirred for 30 min. concentrated, diluted with water, and acidified with 1 N HCl. White solids were filtered, washed with water, and dried in vacuuo (3.37 g, 95%). MS [M+H]⁺ 336.

(d) 8-Cyclohexylmethoxy-5-oxo-2,3,4,5-tetrahydro-benzo[b]oxepine-7-carboxylic acid amide 4-(4-Carbamoyl-3-cyclohexylmethoxy-phenoxy)-butyric acid (3,4 g, 10.6 mmol) was added to PPA at 80° C. The mixture was stirred for 1 h then dumped onto ice. The formed solids were filtered, washed with water, dried, and further purified on silica gel (5% MeOH/CH₂Cl₂) to give an off-white solid (2.62 g, 82%). MS [M+H]⁺ 364. m.p. 185–186° C.

(e) 8-Cyclohexylmethoxy-(R)-5-hydroxy-2,3,4,5-tetrahydro-benzo[b]oxepine-7-carboxylic acid amide To 8-cyclohexylmethoxy-5-oxo-2,3,4,5-tetrahydro-benzo[b]oxepine-7carboxylic acid amide (4.0 g, 13.3 mmol) suspended in CH₂Cl₂ (25 mL) at 42° C. was added (+)-DIP-Chloride (25 mL of CH₂Cl₂). The mixture was stirred at −12° C. for 18 h, concentrated, diluted with Et₂O (200 mL) and treated with diethanolamine (5.1 mL, 53.1 mmol). After stirring for 2.5 h, the formed solids were filtered and washed with Et₂O. The filtrate was concentrated, and the residue purified by silica gel column chomatography (5% MeOH/CH₂Cl₂) to a white solid (3.2 g, 80%). m.p. 164–165° C. Optical purity determined by Mosher Amide formation, 71% e.e.

(f) (S)-5-Azido-8-cyclohexylmethoxy-2,3,4,5-tetrahydro-benzo[b]oxepine-7-carboxylic acid amide This compound was prepared as for Example 1, step d.

(g) (S)-5-Amino-8-cyclohexylmethoxy-2,3,4,5-tetrahydro-benzo[b]oxepine-7-carboxylic acid amide To (S)-5-azido-8-cyclohexylmethoxy-2,3,4,5-tetrahydro-benzo[b]oxepine-7-carboxylic acid amide (2.5 g, 5.8 mmol) in EtOAc (20 mL) was added 10% Pd/C (0.25 g). The mixture was hydrogenated at STP for 17 h, filtered though glass, and concentrated to a white solid (1.8 g, 98%). MS [M−H]⁻ 317, m.p. 145–146° C. Optical purity determined by Mosher Amide formation, 55% e.e.

(h) ({4-[(S)-2-Acetylamino-2-(7-carbamoyl-8-Cyclohexylmethoxy-2,3,4,5-tetrahydro-benzo[b]oxepin-(S)-5-ylcarbamoyl)-ethyl]-phenyl}-phosphono-methyl)-phosphonic acid This compound was prepared as for Example 4. MS [M−H]⁻ 680.

Example 9

({4-[2-(7-Carbamoyl-8-isobutoxy-2,3,4,5-tetrahydro-benzo[b]oxepin-(S)-5-ylcarbamoyl)-(S)-2-(2,2-dimethyl-propionylamino)-ethyl]-phenyl}-phosphono-methyl)-phosphonic acid

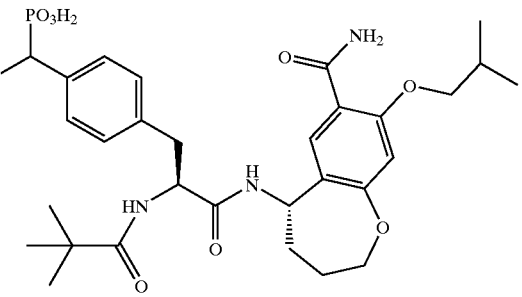

This compound was prepared as for Example 8. MS [M−H]⁺ 684.

Example 10

({4-[2-(7-Carbamoyl-8-isobutoxy-2,3,4,5-tetrahydro-benzo[b]oxepin-(R)-5-ylcarbamoyl)-(S)-2-(2,2-dimethyl-propionylamino)-ethyl]-phenyl}-phosphono-methyl)-phosphonic acid

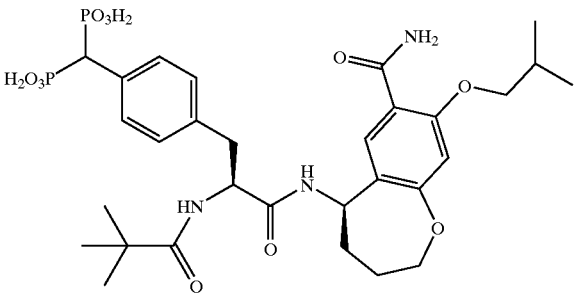

This compound was prepared as for Example 8. MS [M−H]⁺ 684.

Example 11

({4-[(S)-2-Amino-2-(7-carbamoyl-8-cyclohexylmethoxy-2,3,4,5-tetrahydro-benzo[b]oxepin-(R or S)-5-ylcarbamoyl)-ethyl]-phenyl}-phosphono-methyl)-phosphonic acid

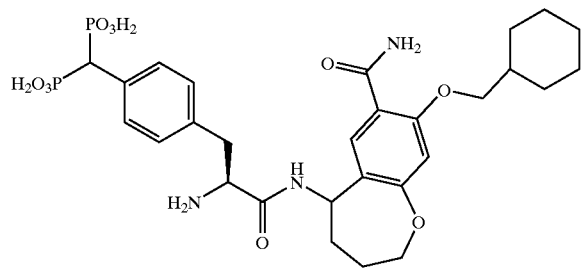

The title compounds were made from intermediates in the synthesis of example 8. MS [M−H]⁻ 638

Example 12

({4-[2-(7-Carbamoyl-8-cyclohexylmethoxy-2,3,4,5-tetrahydro-benzo[b]oxepin-(R or S)-5-ylcarbamoyl)-(S)-2-phenylacetylamino-ethyl]-phenyl}-phosphono-methyl)-phosphonic acid

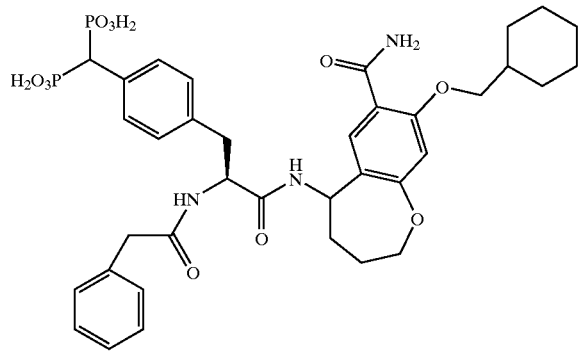

These compound were prepared as for example 8. MS [M−H]+ 756.

Example 13

{4-[(S)-2-Acetylamino-2-(7-carbamoyl-8-cyclohexylmethoxy-2,3,4,5-tetrahydro-benzo[b]oxepin-(R or S)-5-ylcarbamoyl)-ethyl]-phenoxy}-acetic acid

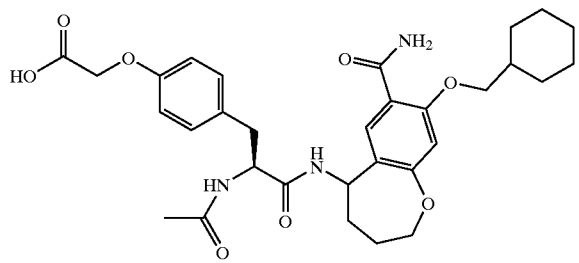

(R,S)-5-Amino-8-cyclohexylmethoxy-2,3,4,5-tetrahydro-benzo[b]oxepine-7-carboxylic acid amide was converted to the title compounds as for example 1.

Example 14

{4-[2-(7-Carbamoyl-8-isobutoxy-2,3,4,5-tetrahydro-benzo[b]oxepin-(S)-5-ylcarbamoyl)-(S)-2-(2,2-dimethyl-propionylamino)-ethyl]-2-phosphono-phenyl}-phosphonic acid

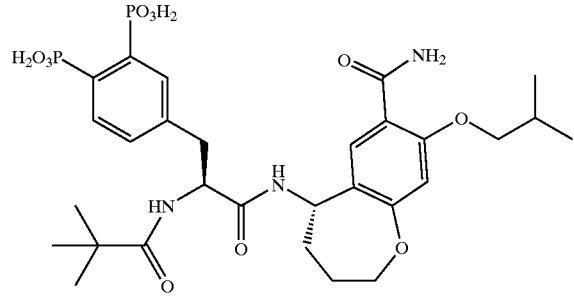

This compound was prepared using intermediates and procedures from Example 6 and Example 8. MS [M−H]+ 670.

Example 15

{4-[(S)-2-Amino-2-(7-carbamoyl-8-cyclohexylmethoxy-2,3,4,5-tetrahydro-benzo[b]oxepin-(S)-5-ylcarbamoyl)-ethyl]-2-phosphono-phenyl}-phosphonic acid

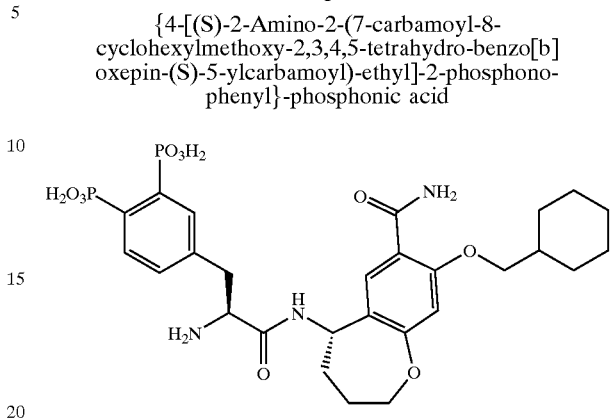

This compound was prepared using intermediates and procedures from Example 6 and Example 8. MS [M−H]− 624.

Example 16

{4-[(S)-2-Acetylamino-2-(7-carbamoyl-8-cyclohexylmethoxy-2,3,4,5-tetrahydro-benzo[b]oxepin-(S)-5-ylcarbamoyl)-ethyl]-2-phosphono-phenyl}-phosphonic acid

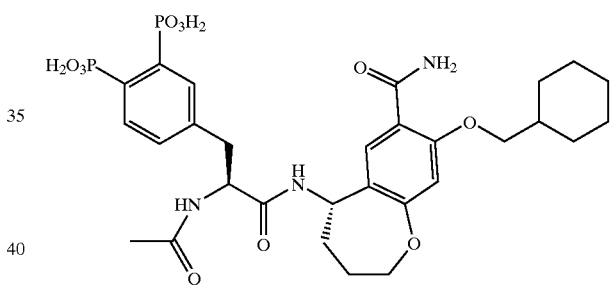

This compound was prepared using intermediates and procedures from Example 6 and Example 8. MS [M−H]− 664.

Example 17

{4-[2-(7-Carbamoyl-8-cyclohexylmethoxy-2,3,4,5-tetrahydro-benzo[b]oxepin-(S)-5-ylcarbamoyl)-2-phenylacetylamino-ethyl]-2-phosphono-phenyl}-phosphonic acid

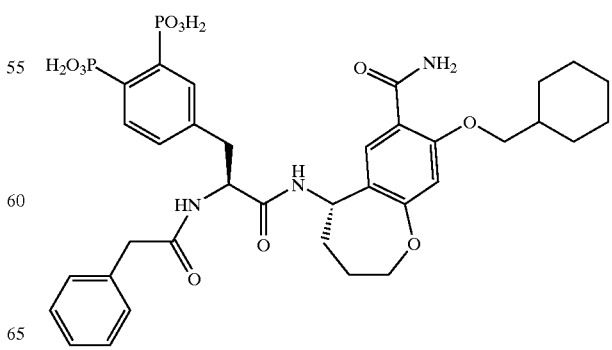

This compound was prepared using intermediates and procedures from Example 6 and Example 8. MS [M–H]⁻ 742.

Example 18

{4-[(S)-2-Acetylamino-2-(7-carbamoyl-8-cyclohexylmethoxy-2,3,4,5-tetrahydro-benzo[b]oxepin-(S)-5-ylcarbamoyl)-ethyl]-phenyl}-phosphonic acid

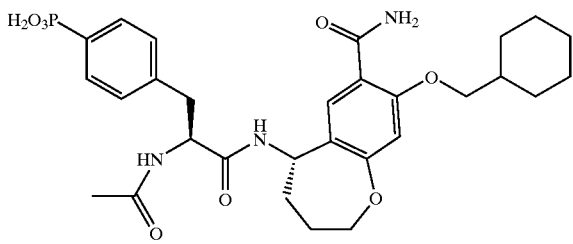

This compound was prepared using an intermediate from Example 8 and from *Bioorg Med. Chem. Lett.* 1997, 7, 1909. MS [M–H]⁻ 586.

Example 19

[(4-{(S)-2-Acetylamino-(S)-2-[1-(4-carbamoyl-7,8-dihydro-6H-5-oxa-9-thia-benzocyclohepten-2-yl)-ethylcarbamoyl]-ethyl}-phenyl)-difluoro-methyl]-phosphonic acid

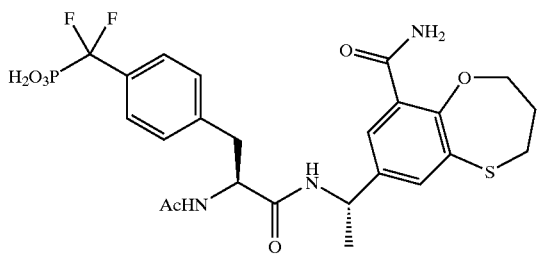

(a) 2-(3-Hydroxy-propylsulfanyl)-phenol

2-Hydroxythiophenol (1.00 g, 8.70 mmol) was added to a mixture of DMF (10 mL) and Cs$_2$CO$_3$ (2.90 g, 8.90 mmol). To this was added 3-bromopropanol (0.80 mL, 9.16 mmol) and the mixture was stirred for 20 min. The mixture was added to into water and extracted with EtOAc. The combined extracts were washed with water, dried over magnesium sulfate and concentrated to a clear oil (2.36 g, 100%). MS [M–H]⁻ 183.

(b) 7,8-Dihydro-6H-5-oxa-9-thia-benzocycloheptene

To 2-(3-hydroxy-propylsulfanyl)-phenol (29.2 g, 158.5 mmol) in THF (450 mL) was added triphenylphosphine (52.0 g, 200.0 mmol). The solution was cooled to –40° C. and diethyl azodicarboxylate (31.5 mL, 164.0 mmol) was added slowly. The solution was warmed to rt and stirred for 2.5 h. The THF was removed by evaporation and the residue was treated with 1 L of Et$_2$O. The formed solids were filtered off, and the filtrate concentrated to an oil which was purified over silica gel (10% Et2O/hexane) to a pink oil (16.2 g, 61%).

(c) 7,8-Dihydro-6H-5-oxa-9-thia-benzocycloheptene-4-carboxylic acid

To 7,8-dihydro-6H-5-oxa-9-thia-benzocycloheptene (16.2 g, 97 mmol) in 250 mL of dry hexane was added tetramethylethylene diamine (16 mL, 106 mmol). The solution was cooled to 0° C. and n-butyllitium (1.6 M solution in hexane, 73 mL, 116.8 mmol) was slowly added with stirring. A tan-colored precipitate slowly started to form and some gas evolution occured. The suspension was stirred at rt for 18 h, after which CO$_2$ gas was bubbled though it for 20 min. An exothermic reaction occured. The mixture was diluted with 300 mL ethyl acetate and 4 N HCl. After all solids dissolved, the organic layer was washed with 1 N HCl. The acid was extracted into the water layer using sat. NaHCO$_3$. The aqueous layer was washed with ethyl acetate and treated with 10 N HCl to pH 1. Extraction with ethyl acetate (2×250 mL), drying over Na$_2$SO$_4$ and concentration yielded the compound as a tan solid (16.5 g, 81%). MS [M–H]⁻ 209.

(d) 7,8-Dihydro-6H-5-oxa-9-thia-benzocycloheptene-4-carboxylic acid amide

To 7,8-dihydro-6H-5-oxa-9-thia-benzocycloheptene-4-carboxylic acid (16.5 g, 78.4 mmol) in 100 mL DMF was added in succession solid HOBT (21.3 g, 157.3 mmol), solid EDC hydrochloride (30.1 g, 157.0 mmol), and 25% aqueous ammonia (18 mL, 128.4 mmol). After stirring for 48 h, the reaction mixture was diluted with 200 mL ethyl acetate and washed with water, 1N HCl, saturated NaHCO$_3$, saturated NH$_4$Cl, and brine. Drying over Na$_2$SO$_4$ and concentration yielded the amide as a tan solid (10.5 g, 64%).

(e) 5-Acetyl-3-(3-chloro-propylsulfanyl)-2-hydroxy-benzamide

Solid aluminum chloride (9.0 g, 67.7 mmol) was suspended in 20 mL of dry dichloromethane at 0° C. The 7,8-dihydro-6H-5-oxa-9-thia-benzocycloheptene-4-carboxylic acid amide (2.7 g, 12.7 mmol) was added as a solution in 20 mL dichloromethane. The deep green solution was stirred at 0° C. for 10 min, then neat acetyl chloride (10 mL, 140.6 mmol) was added dropwise with stirring. The suspension was stirred at 0° C. for 20 min, then at rt for 30 h. The reaction was quenched with 4 N HCl and extracted repeatedly with ethyl acetate. Drying over Na2SO4 and concentration yeilded the crude product. Sgc (ethyl acetate) yielded the product as a tan solid (1.6 g, 44%). MS [M–H]⁻ 286.

(f) 2-Acetyl-7,8-dihydro-6H-5-oxa-9-thia-benzocycloheptene-4-carboxylic acid amide The 5-acetyl-3-(3-chloro-propylsulfanyl)-2-hydroxy-benzamide (2.87 g, 10 mmol) was dissolved in 8 mL dry DMF. Solid Cs$_2$CO$_3$ (4.93 g, 15.1 mmol) was added, followed by catalytic amounts of KI (0.1 g). The suspension was warmed to 70° C. under nitrogen and was stirred for 72 h. After cooling, it was diluted with ethyl acetate and enough 4 N HCl to make the pH about 2. The aqueous layer was extracted with more ethyl acetate. The combined organic layers were washed with water and brine. Drying over Na$_2$SO$_4$ and concentration yielded the product as a solid (1 g, 40%).

(g) 2-(1-Hydro-ethyl)-7,8-dihydro-6H-5-oxa-9-thia-benzocycloheptene-4-carboxylic acid amide To 2-acetyl-7,8-dihydro-6H-5-oxa-9-thia-benzocycloheptene-4-carboxylic acid amide (0.40 g, 1.59 mmol) suspended in EtOH (10 mL) was added NaBH$_4$ (0.060 g, 1.59 mmol). The mixture was stirred for 5 min, made acidic with 1 N HCl, and the EtOH removed in vacuuo. The aqueous was extracted with EtOAc. The combined extracts were washed with water, dried over magnesium sulfate and concentrated to a foam (0.35 g, 87%). MS M+H]⁺ 252.

(h) 2-(1-Azido-ethyl)-7,8-dihydro-6H-5-oxa-9-thia-benzocycloheptene-4-carboxylic acid amide This compound was prepared as for example 1 (d). (0.26 g, 66%).

(i) 2-(1-Amino-ethyl-7,8-dihydro-6H-5-oxa-9-thia-benzocycloheptene-4-carboxylic acid amide To 2-(1-azido-ethyl)-7,8-dihydro-6H-5-oxa-9-thia-benzocycloheptene-4-carboxylic acid amide (0.20 g, 0.73 mmol) in THF (5 mL) was added water (0.10 mL) and triphenylphosphine (0.19 g, 0.73 mmol). The mixture was heated to 50° C. for 20 h, evaporated, and chomatographed over silica gel (10% MeOH/CHCl₃) to give a colorless oil (0.10 g, 55%).

(j) [(4-{(S)-2-Acetylamino-(S)-2-[1-(4-carbamoyl-7,8-dihydro-6H-5-oxa-9-thia-benzocyclohepten-2-yl)-ethylcarbamoyl]-ethyl}-phenyl)-difluoro-methyl]-phosphonic acid This compound was prepared as for example 3 (a–b). MS [M+H]⁺ 572.

Example 20

{4-[(S)-2-Acetylamino-2-(3-carbamoyl-2-cyclohexylmethoxy-6,7,8,9-tetrahydro-5H-benzocyclohepten-(S)-5-ylcarbamoyl)-ethyl]-2-phosphono-phenoxy}-acetic acid and [4-[(S)-Acetylamino-2-(3-carbamoyl-2-cyclohexylmethoxy-6,7,8,9-tetahydro-5H-benzocyclohepten-(S)-5-ylcarbamoyl)-ethyl]-2-(ethoxy-hydroxy-phosphoryl)-phenoxy]-acetic acid

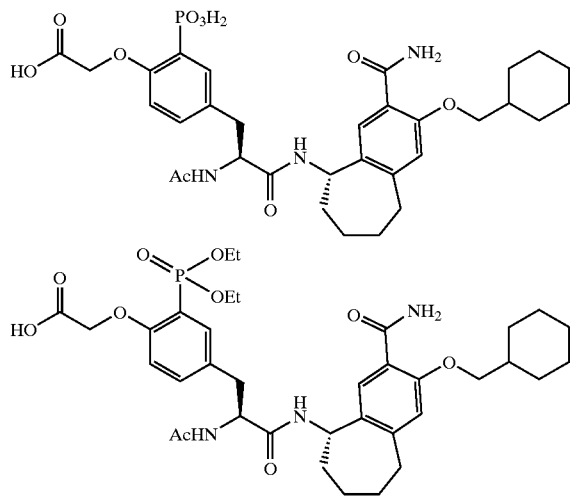

(a) Phosphoric acid diethyl ester 2-iodo-phenyl ester

To a mixture of 2-iodophenol (14.1 g, 64.1 mmol) and potassium carbonate (17.6 g, 128 mmol) in MeCN (100 mL) was added diethylchlorophosphate (11.1 mL, 76.7 mmol). The mixture was allowed to stir at rt for 5 h. The solvent was removed under reduced pressure, the residue diluted with water and extracted with EtOAc. The organic layer was washed with brine, dried over anhydrous Na₂SO₄ and concentrated under reduced pressure. The residue was chromatographed over silica gel (elution with a stepwise gradient 25–40% EtOAc-hexanes) to give 21.7 g (95%) of a pale oil. R_f 0.47 (1:1 EtOAc-hexanes). Electrospray Mass Spectrum (50/50 acetonitrile/water) m/z 357 (M+H).

(b) (2-hydroxy-phenyl)-phosphonic acid diethyl ester

Casteel, D. A.; Peri, S. P. *Synthesis*, 1991, 691.

To a cooled (−78° C.) solution of phosphoric acid diethyl ester 2-iodo-phenyl ester (21.7 g, 61.0 mmol) in dry THF (500 mL) under N₂ was added a 2.5 M solution of BuLi (40 mL, 100 mmol). After 20 min, the reaction was treated with satd aq NH₄Cl (50 mL) and allowed to warm to rt. The mixture was diluted with H₂O (50 mL) and extracted twice with EtOAc. The organic extracts were pooled, washed with brine, dried over anhydrous Na₂SO₄ and concentrated under reduced pressure. The residue was chromatographed over silica gel (20% EtOAc-hexanes) to give 13.1 g (93%) of a pale oil. R_f 0.60 (1:1 EtOAc-hexanes). Electrospray Mass Spectrum (50/50 acetonitrile/water) m/z 231 (M+H).

(c) (2-hydroxy-5-iodo-phenyl)-phosphonic acid diethyl ester

To a cooled (0° C.) mixture of (2-hydroxy-phenyl)-phosphonic acid diethyl ester (13.1 g, 56.9 mmol) and sodium iodide (10.2 g, 68.3 mmol) in DMF (200 mL) was added chloramine-T trihydrate (19.2 g, 68.3 mmol) over 5 min. After 10 min, the reaction was allowed to warm to rt and the mixture was allowed to stir at rt for 2 h. The mixture was diluted with H₂O (50 mL), acidified using 0.5 N HCl and extracted twice with EtOAc. The organic extracts were pooled and washed sequentially with satd. Na₂S₂O₃/brine (1/1) and then brine. The organic layer was dried over anhydrous Na₂SO₄ and concentrated under reduced pressure. The residue was chromatographed over silica gel (elution with a stepwise gradient 5–15% EtOAc-hexanes) to give 14.9 g (73%) of a colorless solid after recrystallization (EtOAc-hexanes). R_f 0.30 (20% EtOAc-hexanes). Electrospray Mass Spectrum (50/50 acetonitrile/water) m/z 357 (M+H).

(d) (2-benzyloxy-5-iodo-phenyl)-phosphonic acid diethyl ester

To a mixture of (2-hydroxy-5-iodo-phenyl)-phosphonic acid diethyl ester (14.7 g, 41.2 mmol) and cesium carbonate, (17.4 g, 53.5 mmol) in DMF (150 mL) was added benzyl bromide (6.40 mL, 54 mmol). The reaction was allowed to stir for 2.5 days at rt at which point the reaction was concentrated under reduced pressure, the residue diluted in 0.5 N HCl (30 mL) and extracted twice with EtOAc. The pooled organic extracts were washed with brine, dried over anhydrous Na₂SO₄ and concentrated under reduced pressure to give 17.4 g (91%) of a colorless solid after recrystallization (EtOAc-hexanes). R_f 0.36 (1:1 EtOAc-hexanes). Electrospray Mass Spectrum (50/50 acetonitrile/water) m/z 447 (M+H).

(e) 3-[4-benzyloxy-3-(diethoxy-phosphoryl)-phenyl]-(S)-2-tert-butoxycarbonylamino-propionic acid methyl ester To a mixture of Zn dust (403 mg, 6.17 mmol) in dry DMA (1 mL) and dry THF (1 mL) was added dibromoethane (55 microliters, 0.64 mmol) and chlorotrimethylsilane (80 microliters, 0.63 mmol). The mixture was sonicated for 15 min under N₂. To this mixture was added a solution of Boc-L-iodoalanine-methyl ester (1.45 g, 4.41 mmol) in dry DMA (1 mL) and dry THF (1 mL). The mixture was sonicated for 30 min and then heated (65° C.) for 45 min under N₂. To the heated mixture was added a solution (2-benzyloxy-5-iodo-phenyl)-phosphonic acid diethyl ester (1.37 g, 2.94 mmol), bis(benzonitrile)dichloropalladium (II) (67 mg, 0.17 mmol) and tri-ortho-tolylphosphine (148 mg, 0.486 mmol) in dry DMA (1 mL) and THF (1 mL) over 5 min. The mixture was allowed to stir for 3 h at 65° C. under N₂ at which point the reaction was allowed to cool to rt, diluted with 0.5 N HCl and extracted twice with Et₂O. The organic extracts were pooled, washed with brine, filtered, dried over anhydrous MgSO₄ and concentrated under reduced pressure. An initial chromatographic purification over silica gel (elution with a stepwise gradient 15–40% acetone-hexanes) was followed by a second chromatographic purification over silica gel (70% EtOAc-hexanes) to give 958 mg (63%) of a pale oil. R_f 0.33 (80% EtOAc-hexanes). Electrospray Mass Spectrum (50/50 acetonitrile/water) m/z 522.5 (M+H).

(f) (S)-2-tert-butoxycarbonylamino-3-[4-benzyloxy-3-(diethoxy-phosphoryl)-phenyl]-propionic acid To a cooled (0° C.) solution (S)-2-tert-butoxycarbonylamino-3-[3-(diethoxy-phosphoryl)-4-hydroxy-phenyl]-propionic acid methyl ester (423 mg, 0.98 mmol) in MeOH (4 mL) was added lithium hydroxide monohydrate (84 mg, 2.0 mmol) in $H_2O$ (4 mL). After 1 h, the reaction was allowed to warm to rt. After 2.5 h, the solution was carefully acidified to pH 2 using 0.5 N HCl and extracted twice with EtOAc. The organic extracts were pooled, washed with brine, dried over anhydrous $Na_2SO_4$ and concentrated to give 379 mg (91%) of a yellow foam. The crude material was carried on without further purification. Electrospray Mass Spectrum (50/50 acetonitrile/water) m/z 416 (M−H).

(g) (S)-9-amino-3-cyclohexylmethoxy-6,7,8,9-tetrahydro-5H-benzocycloheptene-2-carboxylic acid amide To a cooled (0° C.) solution of (S)-9-tert-butoxycarbonylamino-3-cyclohexylmethoxy-6,7,8,9-tetrahydro-5H-benzocycloheptene-2-carboxylic acid amide (198 mg, 0.475 mmol) in DCM (1 mL) was added TFA (1 mL). After 10 min, the reaction was allowed to warm to rt and after 1 h, the reaction was evaporated to dryness. The material was used without further purification for the next step.

(h) {2-Benzyloxy-5-[(S)-2-tert-butoxycarbonylamino-2-(3carbamoyl-2-cyclohexylmethoxy-6,7,8,9-tetrahydro-5H-benzocyclohepten-(S)-5-ylcarbamoyl)-ethyl]-phenyl}-phosphonic acid diethyl ester A solution of (S)-2-tert-butoxycarbonylamino-3-[4-benzyloxy-3-(diethoxy-phosphoryl)-phenyl]-propionic acid (355 mg, 0.700 mmol), 1-hydroxy-7-azabenzotriazole (123 mg, 0.904 mmol) and (S)-9-amino-3-cyclohexylmethoxy-6,7,8,9-tetrahydro-5H-benzocycloheptene-2aboxylic acid amide (ca. 0.475 mmol) in DMF (5 mL) was neutralized by dropwise addition of 4-methylmorpholine. The solution was cooled (−20° C.) and EDC (173 mg, 903 mmol) was added. The reaction was allowed to slowly warm to rt under $N_2$. After 16 h, the reaction was diluted with 0.5 N HCl and extract ed twice with EtOAc. The pooled organic extracts were washed sequentially with brine, satd. $NaHCO_3$ and brine. The organic layer was dried over $Na_2SO_4$ and concentrated. The residue was chromatographed over silica gel (elution with 2% MeOH/$CHCl_3$) to give 342 mg (89%) of a colorless solid. $R_f$ 0.59 (EtOAc). Electrospray Mass Spectrum (50/50 acetonitrile/water) m/z 806 (M+H).

(i) {5-[(S)-2-Acetylamino-2-(3-carbamoyl-2-cyclohexylmethoxy-6,7,8,9-tetrahydro-5H-benzocyclohepten-(S)-5-ylcarbamoyl)-ethyl]-2-benzyloxy-phenyl}-phosphonic acid diethyl ester To a cooled (0° C.) solution of {2-benzyloxy-5-[(S)-2-tert-butoxycabonylamino-2-(3-carbamoyl-2-cyclohexylmethoxy-6,7,8,9-tetrahydro-5H-benzocyclohepten-(S)-5-ylcarbamoyl)ethyl]-phenyl}-phosphonic acid diethyl ester (342 mg, 0.425 mmol) in DCM (1 mL) was added TFA (1 mL). After 10 min, the reaction was allowed to warm to rt and after 1 h, the reaction was evaporated to dryness. The crude material was dissolved in DCM (3 mL) and 4-methylmorpholine (70 μL, 0.638 mmol) and acetic anhydride (60 μL, 0.638 mmol) were added. The reaction was allowed to stir at it for 17 h. The reaction was diluted with 0.5N HCl and extracted twice with EtOAc. The combined extracts were washed with brine, dried over $Na_2SO_4$ and concentrated to a colorless oil. The material was used without further purification for the next step.

(j) [4-[(S)-2-Acetylamino-2-(3-carbamoyl-2-cyclohexylmethoxy-6,7,8,9-tetrahydro-5H-benzocyclohepten-(S)-5-ylcarbamoyl)-ethyl]-2-(diethoxy-phosphoryl)-phenoxy]-acetic acid tert-butyl ester To a solution of {5-[(S)-2-acetylamino-2-(3-carbamoyl-2-cyclohexylmethoxy-6,7,8,9-tetrahydro-5H-benzocycloheptene-(S)-5-ylcarbamoyl)-ethyl]-2-benzyloxy-phenyl}-phosphonic acid diethyl ester (ca. 0.425 mmol) in MeOH (10 mL) was added 10% Pd/C (4 mg). The heterogeneous mixture was degassed under reduced pressure and allowed to stir at rt for 18 h under $H_2$. The catalyst was removed by filtration and the filtrate concentrated. The residue was dissolved in MeCN (5 mL) and cesium carbonate (0.64 mmoles) and tert-butylbromoacetate (0.64 mmoles) was added. The mixture was allowed to stir at rt for 17 h. The reaction was diluted with water and extracted twice with EtOAc. The combined extracts were washed with brine, dried over $Na_2SO_4$ and concentrated. The residue was chromatographed over silica gel (elution with 2% MeOH/$CHCl_3$) to give 278 mg (85%) of a colorless solid. $R_f$ 0.21 (5% MeOH/$CHCl_3$). Electrospray Mass Spectrum (50/50 acetonitrile/water) m/z 770 (M−H).

(k) {4-[(S)-2-Acetylamino-2-(3-carbamoyl-2-cyclohexylmethoxy-6,7,8,9-tetrahydro-5H-benzocyclohepten-(S)-5-ylcarbamoyl)-ethyl]-2-phosphono-phenoxy}-acetic acid and [4-[(S)-Acetylamino-2-(3-carbamoyl-2-cyclohexylmethoxy-6,7,8,9-tetrahydro-5H-benzocyclohepten-(S)-5-ylcarbamoyl)-ethyl]-2-(ethoxy-hydroxy-phosphoryl)-phenoxy]-acetic acid To a cooled (0° C.) solution of [4-[(S)-2-acetylamino-2-(3-carbamoyl-2-cyclohexylmethoxy-6,7,8,9-tetrahydro-5H-benzocyclohepten-(S)-5-ylcarbamoyl)-ethyl]-2-(diethoxy-phosphoryl)-phenoxy]-acetic acid tert-butyl ester (200 mg, 0.259 mmol) in DCM (1 mL) was added TFA (1 mL). After 10 min, the reaction was allowed to warm to rt and after 1 h, the reaction was evaporated to dryness. The residue was dissolved in MeCN (3 mL) and cooled (0° C.). To this solution was added dropwise iodotrimethylsilane (0.80 mL, 5.9 mmol). After 5 h at 0° C., the reaction was quenched with 20% $NaHSO_3$. A solution of 10% NaOH was added until the mixture appeared colorless. The mixture was filtered and purified by RP-HPLC ($CH_3CN/H_2O$) to give {4-[(S)-2-acetylamino-2-(3-carbamoyl-2-cyclohexylmethoxy-6,7,8,9-tetrahydro-5H-benzocyclohepten-(S)-5-ylcarbamoyl)-ethyl]-2-phosphono-phenoxy}-acetic acid (45 mg) MS 658 (M−H) and [4-[(S)-acetylamino-2-(3-carbamoyl-2-cyclohexylmethoxy-6,7,8,9-tetrahydro-5H-benzocyclohepten-(S)-5-ylcarbamoyl)-ethyl]-2-(ethoxy-hydroxy-phosphoryl)-phenoxy]-acetic acid (25 mg) MS 686 (M−H).

Example 21

{4-[(S)-2-Acetylamino-2-(3-carbamoyl-2-cyclohexylmethoxy-6,7,8,9-tetrahydro-5H-benzocyclohepten-(S)-5-ylcarbamoyl)-ethyl]-2-carboxymethoxy-phenoxy}-acetic acid

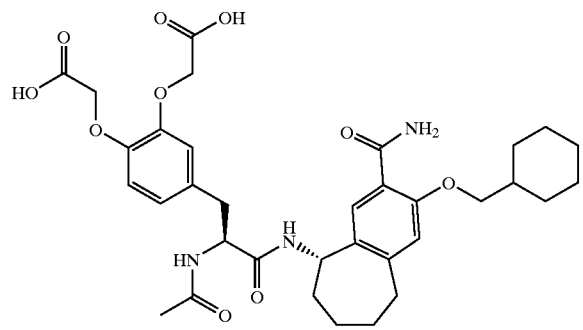

(a) [1-(3-Carbamoyl-2-cyclohexylmethoxy-6,7,8,9-tetrahydro-5H-benzocyclohepten-(S)-5-ylcarbamoyl)-(S)-2-(3,4-dihydroxy-phenyl)-ethyl]-carbamic acid tert-butyl ester (S)-2-tert-Butoxycarbonylamino-3-(3,4-dihydroxy-phenyl)-propionic acid dicyclohexylamine (125 mg, 0.300 mmol) was coupled to (S)-9-amino-3-cyclohexylmethoxy-6,7,8,9-tetrahydro-5H-benzocycloheptene-2-carboxylic acid amide as described for Example X (h). The product was obtained as a colorless foam (60 mg, 33%). $R_f$ 0.32 (5% MeOH/CHCl$_3$). Electrospray Mass Spectrum (50/50 acetonitrile/water) m/z 594 (M–H).

(b) {4-[(S)-2-tert-Butoxycarbonylamino-2-(3-carbamoyl-2-cyclohexylmethoxy-6,7,8,9-tetrahydro-5H-benzocyclohepten-(S)-5-ylcarbamoyl)-ethyl]-2-tert-butoxycarbonylmethoxy-phenoxy}-acetic acid tert-butyl ester To a solution of [1-(3-carbamoyl-2-cyclohexylmethoxy-6,7,8,9-tetrahydro-5H-benzocyclohepten-(S)-5-ylcarbamoyl)-(S)-2-(3,4-dihydroxy-phenyl)-ethyl]-carbamic acid tert-butyl ester (58 mg, 0.097 mmol) in DMF (1.5 mL) was added tert-butylbromoacetate (50 μL, 0.34 mmol) and cesium carbonate (150 mg 0.46 mmol). The mixture was allowed to stir at rt for 22 h. A second addition of tert-butylbromoacetate (25 μL, 0.17 mmol) and cesium carbonate (75 mg 0.23 mmol) was necessary to drive the reaction to completion after an additional 40 h. The mixture was diluted with EtOAc and 0.5 N HCl. The aqueous portion was extracted with fresh EtOAc and the combined organic layers were washed with brine. The solution was dried over Na$_2$SO$_4$, concentrated and chromatographed over silica gel (elution with 3% MeOH/CHCl$_3$) to give the product as a colorless solid after trituration with EtOAc and hexanes (67 mg, 84%). $R_f$ 0.11 (3% MeOH/CHCl$_3$). Electrospray Mass Spectrum (50/50 acetonitrile/water) m/z 824 (M+H).

(c) {4-[(S)-2-Acetylamino-2-(3-carbamoyl-2-cyclohexylmethoxy-6,7,8,9-tetrahydro-5H-benzocyclohepten-(S)-5-ylcarbamoyl)-ethyl]-2-carboxymethoxy-phenoxy}-acetic acid To a cooled (0° C.) solution of {4-[(S)-2-tert-butoxycarbonylamino-2-(3-carbamoyl-2-cyclohexylmethoxy-6,7,8,9-tetrahydro-5H-benzocyclohepten-(S)-5-ylcarbamoyl)-ethyl]-2-tert-butoxycarbonylmethoxy-phenoxy}-acetic acid tert-butyl ester (66 mg, 0.050 mmol) in DCM (1 mL) was added TFA (1 mL). After 0.5 h, the reaction was allowed to warm to rt and after 3 h, the reaction was evaporated to dryness. The crude material was dissolved in DCM (1 mL) and the solution neutralized with 4-methylmorpholine. Acetic anhydride (10 μL, 0.11 mmol) was added and the reaction allowed to stir at rt for 18 h. The reaction was concentrated, diluted with MeCN/H$_2$O and purified by RP-HPLC (MeCN/H$_2$O) to give the product as a colorless solid after lyophilization (22 mg, 44%). Electrospray Mass Spectrum (50/50 acetonitrile/water) m/z 654 (M+H).

Example 22
{4-[(S)-2-Acetylamino-2-(3-carbamoyl-2-cyclohexylmethoxy-6,7,8,9-tetrahydro-5H-benzocyclohepten-(S)-5-ylcarbamoyl)-ethyl]-2-carboxymethyl-phenoxy}-acetic acid

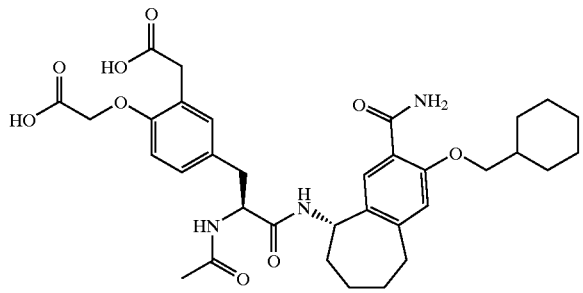

(a) (S)-2-tert-Butoxycarbonylamino-3-(4-hydroxy-3-iodo-phenyl)propionic acid

To a solution of L-4-iodotyrosine (2.00 g, 6.51 mmol) in dioxane (50 mL) and H$_2$O (40 mL) was added 4-methylmorpholine (0.70 mL, 6.4 mmol) and di-tert-butyldicarbonate (2.13 g, 9.77 mmol). After 18 h at rt, di-tert-butyldicarbonate (2.13 g, 9.77 mmol) was added to drive the reaction to completion. The reaction was allowed to stir for another 24 h. The solution was acidified with 0.5 N HCl and extracted twice with EtOAc. The combined extracts were washed with brine, dried over Na$_2$SO$_4$ and concentrated give the product as a foamy solid. The material was used without further purification for the next step.

(b) (S)-2-tert-Butoxycarbonylamino-3-(4-hydroxy-3-iodo-phenyl)-propionic acid benzyl ester To a solution of (S)-2-tert-butoxycarbonylamino-3-(4-hydroxy-3-iodo-phenyl)-propionic acid (3.27 g, 8.03 mmol) in DCM (20 mL) was added DMAP (1.03 g, 8.43 mmol) and benzyl alcohol (2.4 mL, 23 mmol). The solution was cooled (−20° C.) and EDC (1.62 g, 8.45 mmol) was added. The reaction was allowed to slowly warm to rt. After 17 h, the reaction was diluted with 0.5 N HCl and extracted twice with EtOAc. The combined extracts were washed with brine, dried over Na$_2$SO$_4$ and concentrated. The residue was chromatographed over silica gel (elution with 15% EtOAc/hexanes) to give the product as a colorless solid (1.62 g, 50%). $R_f$ 0.41 (40% EtOAc/hexanes). Electrospray Mass Spectrum (50/50 acetonitrile/water) m/z 496 (M–H).

(c) (S)-2-tert-Butoxycarbonylamino-3-(4-ethoxycarbonylmethoxy-3-iodo-phenyl)-propionic acid benzyl ester To a solution of (S)-2-tert butoxycarbonylamino-3-(4-hydroxy-3-iodo-phenyl)-propionic acid benzyl ester (1.88 g, 3.78 mmol) in MeCN (20 mL) was added cesium carbonate (1.85 g, 5.68 mmol) and ethylbromoacetate (0.63 mL, 5.7 mmol). The reaction was allowed to stir at rt for 64 h. The precipitate was removed by filtration and the filtrate concentrated. The residue was chromatographed over silica gel (elution with a gradient 15–33% EtOAc/hexanes) to give the product as a colorless solid (2.00 g, 91%). $R_f$ 0.26 (40% EtOAc/hexanes). Electrospray Mass Spectrum (50/50 acetonitrile/water) m/z 606 (M+Na).

(d) 3-(3-Allyl-4-ethoxycarbonylmethoxy-phenyl)-(S)-2-tert-butoxycarbonylamino-propionic acid benzyl ester To a solution of (S)-2-tert-butoxycarbonylamino-3-(4-ethoxycarbonylmethoxy-3-iodo-phenyl)-propionic acid benzyl ester (1.99 g, 3.41 mmol) in DMF (15 mL) was added lithium chloride (289 mg, 6.82 mmol), allyl tributyltin (1.3 mL, 4.2 mmol) and bis(triphenylphosphine)palladium(II) chloride (143 mg, 0.204 mmol). The mixture was heated (90° C.) and allowed to stir under N$_2$. The reaction was allowed to cool to rt and diluted with Et$_2$O and 0.5 N HCl. The aqueous phase was extracted with fresh Et$_2$O. The combined organic extracts were stirred with saturated potassium fluoride for 17 h. The organic layer was dried over MgSO$_4$, concentrated and chromatographed (elution with 30% Et$_2$O/hexanes). The product was obtained as a colorless solid after recrytallization (EtOAc/hexanes) (1.14 g, 67%). $R_f$ 0.27 (40% Et$_2$O/hexanes). Electrospray Mass Spectrum (50/50 acetonitrile/water) m/z 520 (M+Na).

(e) (S)-2-tert-Butoxycarbonylamino-3-[4-ethoxycarbonylmethoxy-3-(2-oxo-ethyl)-phenyl]-propionic acid benzyl ester To a solution of 3-(3-allyl-4-ethoxycarbonylmethoxy-phenyl)-(S)-2-tert-butoxycarbonylamino-propionic acid benzyl ester (1.00 g, 2.01 mmol) in THF (20 mL) was added pyridine (2 drops) and H$_2$O (20 mL) followed by osmium tetroxide (1.2 mL, 2.5% wt. in tBuOH, 0.096 mmol). The mixture was allowed to stir for 10 min and NaIO$_4$ was added portionwise over 0.5 h. The mixture was allowed to stir for another 0.5 h at rt. The reaction was diluted with H$_2$O and extracted twice with Et$_2$O. The combined organic extracts were washed with brine, dried over MgSO$_4$ and concentrated. The residue was chromatographed over silica gel (elution with 25% EtOAc/hexane) to give the product as an oil (902 mg, 90%). R$_f$ 0.18 (25% EtOAc/hexanes). Electrospray Mass Spectrum (50/50 acetonitrile/water) m/z 522 (M+Na).

(f) (S)-2-tert-Butoxycarbonylamino-3-(4-ethoxycarbonylmethoxy-3-ethoxycarbonylmethyl-phenyl)-propionic acid benzyl ester To a solution of (S)-2-tert-butoxycarbonylamino-3-[4-ethoxycarbonylmethoxy-3-(2-oxo-ethyl)-phenyl]-propionic acid benzyl ester (880 mg, 1.76 mmol) in tBuOH (35 mL) and cyclohexane (9 mL) was added over 15 min a solution of sodium chlorite (1.79 g, 15.8 mmol, 80% tech.) and sodium dihydrogen phosphate dihydrate (1.92 g, 12.3 mmol) in H$_2$O (15 mL). The mixture was allowed to stir at rt for 4 h. The volatiles were removed in vacuo and the remaining mixture was acidified with 0.5 N HCl and extracted twice with EtOAc. The combined extracts were washed with brine, dried over Na$_2$SO$_4$ and concentrated. The residue was dissolved in DMF (5 mL) and cesium carbonate (2.87 g, 8.80 mmol) and iodoethane (0.70 mL, 8.7 mmol) were added. The reaction was allowed to stir at rt for 20 h. The reaction was diluted with EtOAc and 0.5 N HCl. The aqueous layer was extracted with fresh EtOAc and the combined organic extracts were washed with brine and dried over Na$_2$SO$_4$. The solution was concentrated and chromatographed over silica gel (elution with 25% EtOAc/hexanes) to give the product as a colorless oil (849 mg, 89%). R$_f$ 0.13 (25% EtOAc/hexanes). Electrospray Mass Spectrum (50/50 acetonitrile/water) m/z 567 (M+Na).

(g) (S)-2-tert-Butoxycarbonylamino-3-(4-ethoxycarbonylmethoxy-3-ethoxycarbonylmethyl-phenyl)-propionic acid To a solution of (S)-2-tert-butoxycarbonylamino-3-(4-ethoxycarbonylmethoxy-3-ethoxycarbonylmethyl-phenyl)-propionic acid benzyl ester (796 mg, 1.46 mmol) in MeOH (8 mL) was added 10% Pd/C (4 mg). The heterogeneous mixture was degassed under reduced pressure and allowed to stir at rt for 18 h under H$_2$. The catalyst was removed by filtration and the filtrate evaporated to dryness to give the product as a colorless foam (515 mg, 78%) Electrospray Mass Spectrum (50/50 acetonitrile/water) m/z 476 (M+Na).

(h) {4-[(S)-2-tert-Butoxycarbonylamino-2-(3-carbamoyl-2-cyclohexylmethoxy-6,7,8,9-tetrahydro-5H-benzocyclohepten-(S)-5-ylcarbamoyl)-ethyl]-2-ethoxycarbonylmethyl-phenoxy}-acetic acid ethyl ester (S)-2-tert-Butoxycarbonylamino-3-(4-ethoxycarbonylmethoxy-3-ethoxycarbonylmethyl-phenyl)-propionic acid (65 mg, 0.16 mmol) was coupled to (S)-9-amino-3-cyclohexylmethoxy-6,7,8,9-tetrahydro-5H-benzocycloheptene-2-carboxylic acid amide as described for Example X (h). The product was obtained as a colorless solid (92 mg, 78%). R$_f$ 0.27 (75% EtOAc/hexane). Electrospray Mass Spectrum (50/50 acetonitrile/water) m/z 774 (M+Na)

(i) {4-[(S)-2-Acetylamino-2-(3-carbamoyl-2-cyclohexylmethoxy-6,7,8,9-tetrahydro-5H-benzocyclohepten-(S)-5-ylcarbamoyl)-ethyl]-2-carboxymethyl-phenoxy}-acetic acid To a cooled (0° C.) solution of {4-[(S)-2-tert-Butoxycarbonylamino-2-(3-carbamoyl-2-cyclohexylmethoxy-6,7,8,9-tetrahydro-5H-benzocyclohepten-(S)-5-ylcarbamoyl)-ethyl]-2-ethoxycarbonylmethyl-phenoxy}-acetic acid ethyl ester (92 mg, 0.12 mmol) in DCM (0.5 mL) was added TFA (0.5 mL). After 10 min, the reaction was allowed to warm to rt and after 1 h, the reaction was evaporated to dryness. The crude material was dissolved in DCM (0.5 mL) and DMA (0.5 mL) and 4-methylmorpholine (16 μL, 0.17 mmol) and acetic anhydride (25 μL, 0.23 mmol) were added. The reaction was allowed to stir at rt for 18 h. The reaction was diluted with 0.5N HCl and extracted twice with EtOAc. The combined extracts were washed with brine, dried over Na$_2$SO$_4$ and concentrated to a colorless oil. The residue was dissolved in MeOH (0.7 mL) and DMF (0.7 mL) and cooled (0° C.). To this solution was added lithium hydroxide monohydrate (31 mg, 0.74 mmol) in H$_2$O (0.6 mL). After 0.5 h, the reaction was allowed to warm to rt and after 1.5 h, the reaction was neutralized by careful addition of 6 N HCl. Purification by RP-HPLC gave the product as a colorless solid after lyophilization (23 mg, 30%). Electrospray Mass Spectrum (50/50 acetonitrile/water) m/z 638 (M+H)

Example 23

({4-[(S)-2-Acetylamino-2-(3-carbamoyl-2-cyclohexylmethoxy-6,7,8,9-tetrahydro-5H-benzocyclohepten-(S)-5-ylcarbamoyl)-ethyl]-phenyl}-hydroxyacetyl-amino)-acetic acid

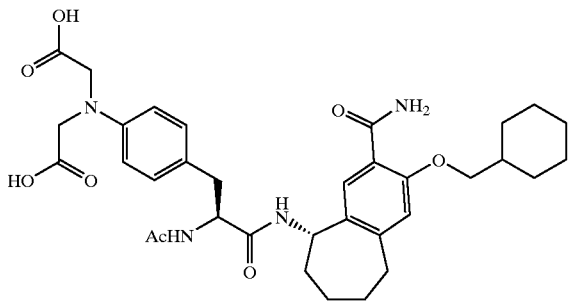

(a) {4-[(S)-2-tert-butoxycarbonylamino-2-(3-carbamoyl-2-cyclohexylmethoxy-6,7,8,9-tetrahydro-5H-benzocyclohepten-(S)-5-ylcarbamoyl)-ethyl]-phenyl}-carbamic acid benzyl ester 3-(4-Benzyloxycarbonylamino-phenyl)-(S)-2-tert-butoxycarbonylamino-propionic acid (417 mg, 0.16 mmol) was coupled to (S)-9-amino-3-cyclohexylmethoxy-6,7,8,9-tetrahydro-5H-benzocycloheptene-2-carboxylic acid amide as described for Example X (h). The product was obtained as a colorless solid (231 mg, 65%). R$_f$ 0.28 (5% MeOH/CHCl$_3$). Electrospray Mass Spectrum (50/50 acetonitrile/water) m/z 713 (M+H).

(b) ({4-[(S)-2-Amino-2-(3-carbamoyl-2-cyclohexylmethoxy-6,7,8,9-tetrahydro-5H-benzocyclohepten-(S)-5-ylcarbamoyl)-ethyl]-phenyl}-ethoxyacetyl-amino)-acetic acid ethyl ester To a solution of {4-[(S)-2-tert-butoxycarbonylamino-2-(3-carbamoyl-2-cyclohexylmethoxy-6,7,8,9-tetrahydro-5H-benzocyclohepten-(S)-5-ylcarbamoyl)-ethyl]-phenyl}-carbamic acid benzyl ester (231 mg, 0.324 mmol) in MeOH (5 mL) was added 10% Pd/C (10 mg). The heterogeneous mixture was degassed under reduced pressure and allowed to stir at rt for 46 h under H$_2$. The catalyst was removed by filtration and the filtrate evaporated to dryness. The residue was dissolved in MeCN (5 mL) and cesium carbonate (264 mg, 0.810 mmol) and ethylbromoacetate (0.36 mL, 3.25 mmol) were added. The reaction was warmed (90° C.) and allowed to stir for 40 h. A second portion of ethylbromoacetate (0.18 mL was added and the reaction allowed to stir at 90° C. for 18 h. The reaction was concentrated, diluted with H₂O and extracted twice with EtOAc. The combined organic extracts were washed with brine, dried over Na₂SO₄ and concentrated. The residue was chromatographed over silica gel (elution with a stepwise gradient 2–4% MeOH/CHCl₃) to give the product as a colorless solid (132 mg, 63%). R$_f$ 0.18 (5% MeOH/CHCl₃). Electrospray Mass Spectrum (50/50 acetonitrile/water) m/z 651 (M+H).

(c) ({4-[(S)-2-Acetylamino-2-(3-carbamoyl-2-cyclohexylmethoxy-6,7,8,9-tetrahydro-5H-benzocyclohepten-(S)-5-ylcarbamoyl)-ethyl]-phenyl}-ethoxyacetyl-amino)-acetic acid ethyl ester To a solution of ({4-[(S)-2-amino-2-(3-carbamoyl-2-cyclohexylmethoxy-6,7,8,9-tetrahydro-5H-benzocyclohepten-(S)-5-ylcarbamoyl)-ethyl]-phenyl}-ethoxyacetyl-amino)-acetic acid ethyl ester (132 mg, 0.203 mmol) in DCM (1.5 mL) was added 4-methylmorpholine (27 μL, 0.24 mmol) and acetic anhydride (0.23 μL, 0.24 mmol). Allowed to stir at rt for 18 h. The reaction was diluted with 0.5 N HCl and extracted twice with EtOAc. The combined extracts were washed with brine, dried over Na₂SO₄ and concentrated. The residue was chromatographed over silica gel (elution with a stepwise gradient 1–3% MeOH/CHCl₃) to give the product as a colorless solid (95 mg, 68%). R$_f$ 0.41 (5% MeOH/CHCl₃). Electrospray Mass Spectrum (50/50 acetonitrile/water) m/z 693 (M+H).

(d) ({4-[(S)-2-Acetylamino-2-(3-carbamoyl-2-cyclohexylmethoxy-6,7,8,9-tetrahydro-5H-benzocyclohepten-(S)-5-ylcarbamoyl)-ethyl]-phenyl}-hydroxyacetyl-amino)-acetic acid To a solution of ({4-[(S)-2-acetylamino-2-(3-carbamoyl-2-cyclohexylmethoxy-6,7,8,9-tetrahydro-5H-benzocyclohepten-(S)-5-ylcarbamoyl)-ethyl]-phenyl}-ethoxyacetyl-amino)-acetic acid ethyl ester (80 mg, 0.12 mmol) in MeOH (1 mL) was added lithium hydroxide monohydrate (15 mg, 0.36 mmol) in H₂O (1 mL). After 3 h, the reaction was diluted with MeOH (4 mL) and DMF (1 mL) and purified by RP-HPLC (MeCN/H₂O) to give the product as a colorless solid after lyophilization (25 mg, 34%). Electrospray Mass Spectrum (50/50 acetonitrile/water) m/z 635 (M–H).

What is claimed is:

1. A compound of the formula:

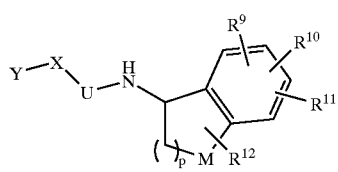

I wherein

Y is

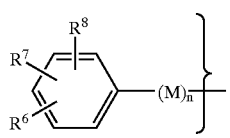

(a)

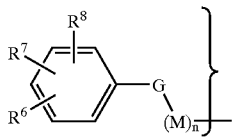

(b)

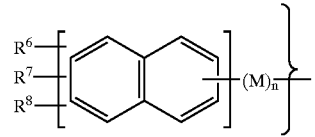

(c)

each occurrence of G is —O—, —S— or —NR—;

R⁶ comprises —APO₃RR, —OPO₃RR, —ASO₃R, —OSO₃R, —ACO₂R, —A-tetrazole, —A—N—(PO₃RR)(PO₃RR), —ASO₂NRR, —ACOCF₃, —(C=O)J, —C(R)(J)(K) or —C(Z)(J)(K);

where each occurrence of A is independently a covalent bond, —G—M— or —(M)$_m$—;

each occurrence of M is an independently selected, substituted or unsubstituted, methylene moiety, and any M-M moiety may be electronically saturated or unsaturated;

each n is independently 0, 1, 2, 3, 4 or 5;

each m is independently 0, 1 or 2;

J and K are independently —APO₃RR, —OPO₃RR, —ASO₃R, —OSO₃R, —ACO₂R, —A-tetrazole, —ASO₂NRR, —(M)$_n$—NRR or —(M)$_n$—OR;

Z is a halogen;

R⁷ and R⁸ are independently R, —CN, —NO₂, Z, J, —A(M)$_n$aliphatic, —G(M)$_n$aliphatic, —(M)$_n$COCF₃, —(M)$_n$OH, —(M)$_n$COOR, —A—(M)$_n$NRR, —G(M)$_q$NRR, —(M)$_n$CHO, —A(M)$_n$N(R)(CO)R, —A(M)$_n$N(R)(CO)GR, —G(M)$_q$N(R)(CO)R, —G(M)$_q$N(R)(CO)GR, —A—(M)$_n$—CO—NRR, or —G(M)$_n$—CO—NRR, where the aliphatic groups may be substituted or unsubstituted; or R⁷ is a covalent bond to an R⁴ substituent of X to form an aliphatic, aryl or heterocyclic ring of 4 to 8 atoms;

each occurrence of R (unnumbered) represents hydrogen or an aliphatic, heteroaliphatic, aryl, heteroaryl, (aryl) aliphatic-, or (heteroaryl)aliphatic- moiety, each of which (other than hydrogen) may be substituted or unsubstituted;

q is an integer from 1 to 8;

X is: —CR³R⁴)$_m$— or —NR⁴—;

R³ is hydrogen, R(CO)NR—, RRN(CO)NR—, RSO₂NR—, RCSNR—, RRNCSNR—, RRNSO₂NR—, ROCONR—, RRN—, or

; and, and,

R⁴ is hydrogen, aliphatic, cycloaliphatic-(M)$_n$—, aryl-(M)$_n$—, heterocyclic-(M)$_n$—, R—SO₂M$_n$—, (RO—CO)(M)$_n$— or (RRN—CO)(M)$_n$—, where the aliphatic, cycloaliphatic, aryl or heterocyclic moiety is substituted or unsubstituted;

p is 1, 2, 3 or 4;

$R^9$, $R^{10}$, $R^{11}$ and $R^{12}$ are independently —$(M)_n Z$, —$(M)_n R$, —$(M)_n GR$, —$(M)_n WR$, —$(M)_n WGR$, or —$(M)_n W$—$COR$, or $R^9$ and $R^{10}$ are covalently linked together to form an aliphatic, hetercyclic or aryl fused ring; and, U and W are independently —CO—, —CS—, —M—, —SO—, or —$SO_2$—;

or a pharmaceutically acceptable derivative thereof.

2. A compound of claim 1 of the formula:

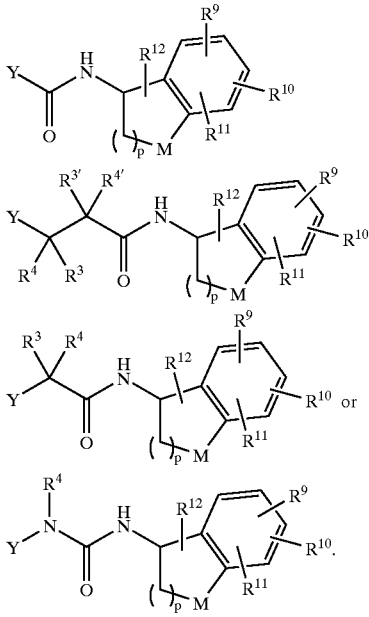

3. A compound of claim 1 wherein each n is independently 0, 1 or 2.

4. A compound of claim 1 wherein X is —$CH(NH_2)$—.

5. A compound of claim 1 of the formula

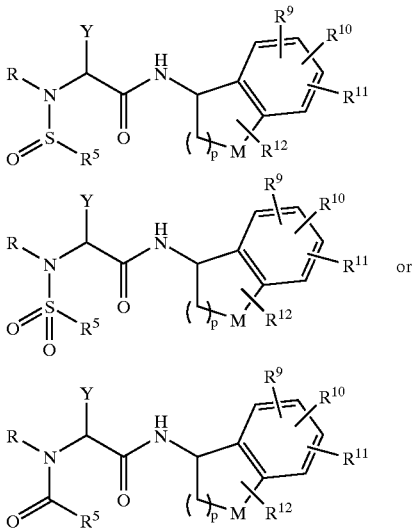

where $R^5$ comprises a substituted or unsubstituted lower aliphatic or alkoxyl or is a substituted or unsubstituted —$(M)_n$-aryl or —$(M)_n$-heterocyclic group.

6. A compound of claim 5 wherein $R^5$ comprises —$(M)_n CH_3$, —$(M)_n$aryl, —$(M)_n$heterocyclic, —$(M)_n CN$, —$(M)_n COOR$, —O—$(M)_n CH_3$, —$O(M)_n$aryl, —$O(M)_n$heterocyclic, —$O(M)_n CN$, or —$O(M)_n COOR$, where n is 0, 1, 2, 3, 4, or 5.

7. A compound of claim 5 wherein $R^5$ is a substituted or unsubstituted methyl, ethyl, i-propyl, n-propyl, n-butyl, isobutyl, t-butyl, cyclobutyl, n-amyl, sec-amyl, isoamyl, cyclopentyl, n-hexyl, sec-hexyl, isohexyl, cyclohexyl or benzyl.

8. A compound of claim 5 wherein $R^5$ comprises —$(CH_2)_n CH_3$, —$(CH_2)(CH_2)_n$aryl, —$(CH_2)(CH_2)_n$heterocyclic, —$(CH_2)(CH_2)_n CN$, —$(CH_2)(CH_2)_n COOR$, —$O(CH_2)_n CH_3$, —$O(CH_2)(CH_2)_n$aryl, —$O(CH_2)(CH_2)_n$heterocyclic, —$O(CH_2)(CH_2)_n CN$, or —$O(CH_2)(CH_2)_n COOR$, where n is 0, 1, 2, 3, 4, or 5.

9. A compound of claim 8 wherein $R^5$ comprises —$CH_2 CN$, —$CH_2$phenyl, —$CH_2$aryl, —$CH_2$heterocyclic, —$CH_2 COOR$, —$(CH_2)_2 COOR$, —$(CH_2)_3 COOR$, —$(CH_2)_4 COOR$, where R is H, lower alkyl or benzyl.

10. A compound of claim 1 of the formula

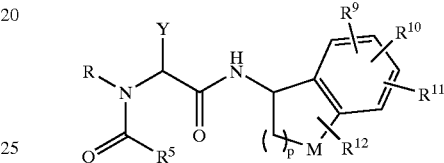

wherein $R^5$ comprises —O—$(M)_n CH_3$, —$O(M)_n$aryl, —$O(M)_n$heterocyclic, —$O(M)_n CN$, or —$O(M)_n COOR$, where n is 0, 1, 2, 3,4, or 5.

11. A compound of claim 10 wherein $R^5$ comprises —$O(CH_2)_n CH_3$, —$O(CH_2)(CH_2)_n$aryl, —$O(CH_2)(CH_2)_n$heterocyclic, —$O(CH_2)(CH_2)_n CN$, or —$O(CH_2)(CH_2)_n COOR$, where n is 0, 1, 2, 3, 4, or 5.

12. A compound of claim 10 wherein $R^5$ comprises —O-(substituted or unsubstituted lower alkyl or benzyl).

13. A compound of claim 1 of the formula

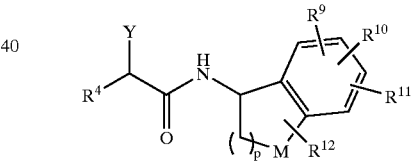

where $R^4$ is hydrogen, substituted or unsubstituted aliphatic (which may be branched, unbranched or cyclic), substituted or unsubstituted aryl-$(M)_n$—, substituted or unsubstituted heterocyclic-$(M)_n$—, or $(CO_2 R)(M)_n$—.

14. A compound of claim 13 wherein $R^4$ is —$(M)_n (CO)OR$, —$(M)_n SO_2 R$, —$(M)_n (CO)NRR$, or —$(M)_n$(tetrazole).

15. A compound of claim 14 wherein $R^4$ is —$CH_2 COOR$, —$CH_2 SO_2 R$, —$CH_2 (CO)NRR$, or -tetrazole.

16. A compound of claim 14 wherein each R is independently H, lower alkyl or benzyl.

17. A compound of claim 1 of the formula

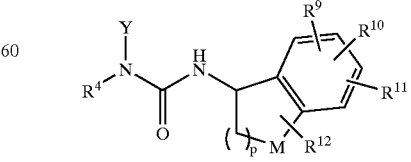

where $R^4$ is hydrogen, substituted or unsubstituted aliphatic (which may be branched, unbranched or cyclic), substituted or unsubstituted aryl-(M)$_n$—, substituted or unsubstituted heterocyclic-(M)$_n$—, or (CO$_2$R)(M)$_n$—.

18. A compound of claim 17 wherein R$^4$ is hydrogen.

19. A compound of claim 1 of the formula

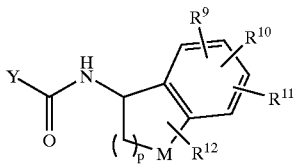

20. A compound of any claims 5–12 wherein each R is H.

21. A compound of any claims 1–19 wherein M is —CH$_2$—.

22. A compound of any claims 1–19 wherein Y comprises

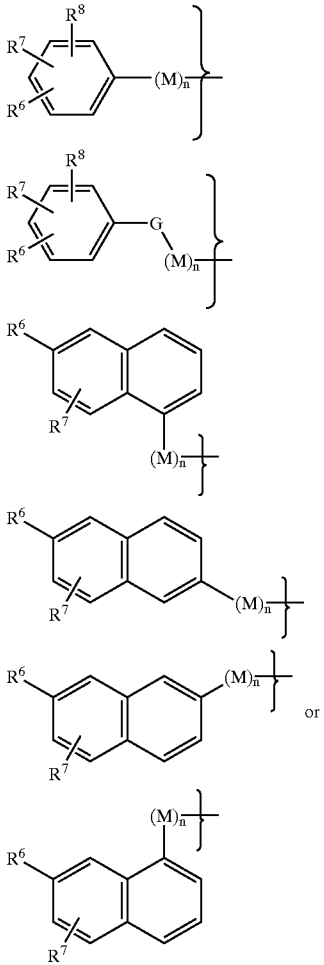

23. A compound of claim 22 wherein
R$^6$ comprises —OR, —APO$_3$RR, —OPO$_3$RR, —ASO$_3$R, —OSO$_3$R, —ACO$_2$R, —A-tetrazole, —ASO$_2$NRR, —ACOCF$_3$, —C(R)(J)(K) or —C(Z)(J)(K); and
R$^7$ and R$^8$ are independently H, —CN, —NO$_2$, halogen, J, —A—(M)$_n$aliphatic, —G—(M)$_n$aliphatic, —(M)$_n$COCF$_3$, —(M)$_n$OH, —(M)$_n$COOR, —A—(M)$_n$NRR, —G—(M)$_q$NRR, —(M)$_n$CHO, —A—(M)$_n$N(R)(CO)R, —G—(M)$_q$N(R)(CO)R, —A—(M)$_n$—CO—NRR, or —G—(M)$_n$—CO—NRR, where the aliphatic groups may be substituted or unsubstituted; or R$^7$ is a covalent bond to an R$^4$ substituent of X to form a ring of 4 to 8 atoms.

24. A compound of claim 22 wherein
R$^6$ comprises —OR, —APO$_3$RR, —OPO$_3$RR, —ACO$_2$R, —ACOCF$_3$ or —C(R)(J)(K);
A comprises —CH$_2$—, —OCH$_2$—, —CF$_2$—, —CHF—, —CHOH— or a covalent bond;
each R H, or substituted or unsubstituted lower alkyl or substituted or unsubstituted benzyl; and,
R$^7$ and R$^8$ are independently H, J, —A—(M) substituted or unsubstituted aliphatic, —G—(M) substituted or unsubstituted aliphatic, —(M)$_n$COCF$_3$, —(M)$_n$OH, —(M)$_n$COOR, —A—(M)$_n$NRR, —(M)$_n$CHO, —A—(M)$_n$N(R)(CO)R or —A—(M)$_n$—CO—NRR.

25. A compound of claim 22 wherein R$^6$ comprises —OH, —PO$_3$RR, —OPO$_3$RR, —CH$_2$PO$_3$RR, —CF$_2$PO$_3$RR, —OCH$_2$CO$_2$R, —NHCH$_2$CO$_2$R, —CH$_2$CO$_2$R, —CF$_2$CO$_2$R, —CH$_2$SO$_3$R, —CF$_2$SO$_3$R, —CH$_2$COCF$_3$, —CF$_2$COCF$_3$, —CH(PO$_3$RR)$_2$, —CH(OH)(PO$_3$RR), —CH(NH$_2$)(PO$_3$RR), —CH(CO$_2$R)$_2$, —CF(CO$_2$R)$_2$, —CH(PO$_3$RR)(CO$_2$R"), —CH(PO$_3$RR)(SO$_3$R"), —CH(PO$_3$RR)(SO$_2$NH$_2$), —CH(SO$_2$NH$_2$)$_2$, or —CH(SO$_3$RR)$_2$.

26. A compound of claim 25 in which one or more R group in the —PO$_3$RR, —OPO$_3$RR, —CH$_2$PO$_3$RR, —CF$_2$PO$_3$RR, —OCH$_2$CO$_2$R, —NHCH$_2$CO$_2$R, —CH$_2$CO$_2$R, —CF$_2$CO$_2$R, —CH$_2$SO$_3$R, —CH$_2$COCF$_3$, —CF$_2$COCF$_3$, —CH(PO$_3$RR)$_2$, —CH(OH)(PO$_3$RR), —CH(NH$_2$)(PO$_3$RR), —CH(CO$_2$R)$_2$, —CF(CO$_2$R)$_2$, —CH(PO$_3$RR)(CO$_2$R), —CH(PO$_3$RR)(SO$_3$R), —CH(PO$_3$RR)(SO$_2$NH$_2$), —CH(SO$_2$NH$_2$)$_2$, or —CH(SO$_3$RR)$_2$ moiety is H.

27. A compound of claim 25 in which one or more R in the —PO$_3$RR, —OPO$_3$RR, —CH$_2$PO$_3$RR, —CF$_2$PO$_3$RR, —OCH$_2$CO$_2$R, —NHCH$_2$CO$_2$R, —CH$_2$CO$_2$R, —CF$_2$CO$_2$R, —CH$_2$SO$_3$R, —CF$_2$SO$_3$R, —CH$_2$COCF$_3$, —CF$_2$COCF$_3$, —CH(PO$_3$RR)$_2$, —CH(OH)(PO$_3$RR), —CH(NH$_2$)(PO$_3$RR), —CH(CO$_2$R)$_2$, —CH(PO$_3$RR)(CO$_2$R), —CH(PO$_3$RR)(SO$_3$R), —CH(PO$_3$RR)(SO$_2$NH$_2$), —CH(SO$_2$NH$_2$)$_2$, or —CH(SO$_2$RR)$_2$ moiety is —(M)$_m$CH$_2$Z, —(M)$_m$CHZ$_2$, —(M)$_m$CZ$_3$, —R$^{15}$, —M—O—CO—R$^{15}$ or —M—O—CO—OR$^5$, where Z is halogen and R$^{15}$ is substituted or unsubstituted lower aliphatic, aryl or heterocyclic.

28. A compound of claim 27 in which R$^{15}$ is methyl, ethyl, n-propyl, i-propyl, n-butyl, isobutyl, t-butyl, n-amyl, sec-amyl, benzyl or substituted benzyl.

29. A compound of claim 25 wherein R$^7$ and R$^8$ are H.

30. A compound of claim 25 wherein R$^7$ is J, —A—(M)$_n$(substituted o aliphatic, aryl or heterocyclic), —G—(M)$_n$(substituted or unsubstituted aliphatic, aryl or heterocyclic), —(M)$_n$COCF$_3$, —(M)$_n$OH, —(M)$_n$COOR, —A—(M)$_n$NRR, —(M)$_n$CHO, —A—(M)$_n$N(R)(CO)R, —A—(M)$_n$—NRR or —A—(M)$_n$—CO—NRR; and R$^8$ is H.

31. A compound of claim 25 wherein R$^7$ is lower alkyl, lower alkenyl, —OH, —NH$_2$, —NO$_2$, —CN, —NHR, —NHCOR, —CHO, —CH$_2$CHO, —PO$_3$RR, —OPO$_3$RR, —CH$_2$PO$_3$RR, —CF$_2$PO$_3$RR, —OCH$_2$CO$_2$R, —NHCH$_2$CO$_2$R, —CH$_2$CO$_2$R, —CF$_2$CO$_2$R, —SO$_3$R, —CH$_2$SO$_3$R, —CF$_2$SO$_3$R, —COCF$_3$, —COCH$_2$F, —COCF$_2$H, —CF$_2$COCF$_3$ or —SO$_2$NH$_2$.

32. A compound of claim 31 in which at least one R group in —PO$_3$RR, —OPO$_3$RR, —CH$_2$PO$_3$RR, —CF$_2$PO$_3$RR, —OCH$_2$CO$_2$R, —NHCH$_2$CO$_2$R, —CH$_2$CO$_2$R, —CF$_2$CO$_2$R, —SO$_3$R, —CH$_2$SO$_3$R, or —CF$_2$SO$_3$R is H.

33. A compound of claim 31 in which at least one R group in —PO$_3$RR, —OPO$_3$RR, —CH$_2$PO$_3$RR, —CF$_2$PO$_3$RR, —OCH$_2$CO$_2$R, —NHCH$_2$CO$_2$R, —CH$_2$CO$_2$R, —CF$_2$CO$_2$R, —SO$_3$R, —CH$_2$SO$_3$R, or —CF$_2$SO$_3$R is —(M)$_m$—CH$_2$Z, —(M)$_m$—CHZ$_2$, —(M)$_m$—CZ$_3$, —R$^{15}$, —M—O—CO—R$^{15}$ or —M—O—CO—OR$^{15}$, where Z is halogen and R$^{15}$ is substituted or unsubstituted lower aliphatic, aryl or heterocyclic.

34. A compound of claim 33 in which R$^{15}$ is methyl, ethyl, n-propyl, i-propyl, n-butyl, isobutyl, t-butyl, n-amyl, sec-amyl, benzyl or substituted benzyl.

35. A compound of claim 29 wherein R$^6$ comprises —APO$_3$RR or —OPO$_3$RR and R$^7$ is —A—(M)$_n$-aliphatic or —G—(M)$_n$-aliphatic, where the aliphatic moiety is substituted or unsubstituted.

36. A compound of claim 35 wherein R$^6$ comprises —OPO$_3$H$_2$.

37. A compound of claim 22 wherein R$^6$ and R$^7$ are independently selected from J and K.

38. A compound of claim 22 wherein R$^6$ is —C(R)(J)(K).

39. A compound of claim 38 wherein R is H.

40. A compound of claim 38 wherein J is —PO$_3$RR.

41. A compound of claim 40 in which one or both R groups is H.

42. A compound of claim 40 in which one or both R groups is R$^{15}$, —(M)$_m$—CH$_2$Z, —(M)$_m$—CHZ$_2$, —(M)$_m$—CZ$_3$, —M—O—CO—R$^{15}$ or —M—O—CO—OR$^{15}$, where Z is halogen and R$^{15}$ is substituted or unsubstituted lower aliphatic, aryl or heterocyclic.

43. A compound of claim 42 in which R$^{15}$ is methyl, ethyl, n-propyl, i-propyl, n-butyl, isobutyl, t-butyl, n-amyl, sec-amyl, benzyl or substituted benzyl.

44. A compound of claim wherein each of R$^9$, R$^{10}$, R$^{11}$ and R$^{12}$ is independently —(M)$_n$Z, —(M)$_n$R, —G(M)$_n$R, —(M)$_n$WR or —(M)$_n$W—GR.

45. A compound of claim 44 wherein one or more of the R groups contain at least one substituent selected from halo, hydroxy, or a substituted or unsubstituted aliphatic, amino, amido or sulfonamido moiety.

46. A compound of claim 44 wherein one or more of R$^9$, R$^{10}$, R$^{11}$, and R$^{12}$ is a substituted aliphatic moiety containing at least one substituent selected from substituted or unsubstituted cycloaliphatic, substituted or unsubstituted aryl, substituted or unsubstituted heteroaryl, —CO$_2$R, —CO—NRR, and —OR.

47. A compound of claim 44, wherein one or more of R$^9$, R$^{10}$, R$^{11}$, and R$^{12}$ comprises —(M)$_n$(cycloaliphatic), —(M)$_n$(substituted or unsubstituted aryl), —(M)$_n$(substituted or unsubstituted heteroaryl), —(M)$_n$CHO, —(M)$_n$CONH$_2$, —(M)$_n$CSNH$_2$, —(M)$_n$SONH$_2$, —(M)$_n$SO$_2$NRR, —(M)$_n$OR, —(M)$_n$(lower aliphatic), —(M)$_n$—C(OR)RR, or —(M)$_n$—C=CRR.

48. A compound of claim 44, wherein one or more of R$^9$, R$^{10}$, R$^{11}$, and R$^{12}$ comprises —G(M)$_n$(aliphatic), —G(M)$_n$(cycloaliphatic), —G(M)$_n$(substituted or unsubstituted aryl), —G(M)$_n$(substituted or unsubstituted heteroaryl), —G(M)$_n$CHO, —G(M)$_n$CONH$_2$, —G(M)$_n$CSNH$_2$, —G(M)$_n$SONH$_2$, —G(M)$_n$SO$_2$NRR, —G(M)$_n$OR, —G(M)$_n$(lower aliphatic), —G(M)$_n$—C(OR)RR, or —G(M)$_n$—C=CRR.

49. A compound of claim 48 wherein —G(M)$_n$ comprises —OCH$_2$—, —SCH$_2$— or —NRCH$_2$—.

50. A compound of claim 44, wherein one or more of R$^9$, R$^{10}$, R$^{11}$, and R$^{12}$ comprises methyl, —(CH$_2$)$_q$R$^{13}$ where q is 1–7 and R$^{13}$ comprises methyl; i-propyl; i-butyl; t-butyl; cycloaliphatic; phenyl; substituted phenyl; naphthyl; substituted naphthyl; a 5, 6 or 7-membered heterocyclic ring or a bicyclic heterocyclic moiety.

51. A compound of claim 44, wherein one or more of R$^9$, R$^{10}$, R$^{11}$, and R$^{12}$ comprises —(M)$_n$W—NH—R and one or more of R$^9$, R$^{10}$, R$^{11}$, and R$^{12}$ comprises —O(M)$_m$(aliphatic).

52. A compound of claim 44 of the formula:

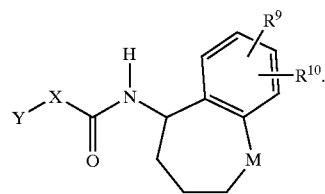

53. A compound of claim 44, wherein one or more of R$^9$, R$^{10}$, R$^{11}$, and R$^{12}$ comprises —(M)$_n$(CO)—NH—R.

54. A compound of claim 44, wherein one or more of R$^9$, R$^{10}$, R$^{11}$, and R$^{12}$ comprises —CONH—R.

55. A compound of claim 44, wherein one or more of R$^9$, R$^{10}$, R$^{11}$, and R$^{12}$ comprises —(CH$_2$)$_m$CONH—R.

56. A compound of claim 1 of the formula:

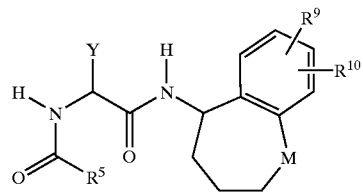

where R$^5$ comprises a substituted or unsubstituted lower aliphatic moiety, and R$^9$ comprises —(M)$_n$W—NH—R and R$^{10}$ comprises —O(M)$_m$(aliphatic).

57. A compound of claim 56, wherein R$^9$ comprises —CONH—R and R$^{10}$ comprises —OM-cycloaliphatic or —OM-branched chain aliphatic.

58. A compound of claim 56, wherein R$^9$ comprises —CH$_2$CONH—R and R$^{10}$ comprises —OM-cycloaliphatic or —OM-branched chain aliphatic.

59. A compound of claim 44, wherein Y comprises:

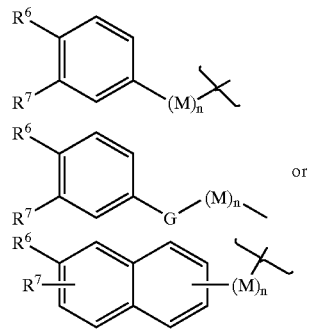

R$^6$ comprises —APO$_3$RR, —ASO$_3$R, —ACO$_2$R, —ASO$_2$NRR, —ACOCF$_3$, or —C(R)(J)(K); and, R$^7$ is H, —CN, —NO$_2$, halogen, J, —A—(M)$_n$substituted or unsubstituted aliphatic, —(M)$_n$COCF$_3$, —(M)$_n$OH, —(M)$_n$COOR, —A—(M)$_n$NRR, —(M)$_n$CHO, —A—(M)$_n$N(R)(CO)R or —A—(M)$_n$—CO—NRR.

60. A compound of claim 59, wherein R$^6$ comprises —OPO(OH)$_2$, —PO(OH)$_2$, —OCH$_2$COOH, —CF$_2$PO(OH)$_2$, or —CH(PO$_3$H$_2$).

61. A compound of claim 44, wherein R$^7$ comprises H.

62. A compound of claim 44, wherein R$^7$ comprises CHO.

63. A compound of claim 44, wherein R$^7$ comprises J.

64. A compound of claim 44, wherein R$^7$ comprises —A—(M)$_n$substituted or unsubstituted aliphatic.

65. A compound of claim 44, wherein R$^6$ comprises —OPO(OH)$_2$ and R$^7$ is H.

66. A compound of claim 64, wherein $(M)_n$ is $(CH_2)_n$.

67. A compound of claim 66, wherein n is 1.

68. A compound of claim 59, wherein one or more (unnumbered) R groups comprise —$(M)_mCH_2Z$, —$(M)_mCHZ_2$, —$(M)_mCZ_3$, —M—O—CO—$R^{15}$ or —M—O—CO—$OR^{15}$, where Z is halogen and $R^{15}$ is a substituted or unsubstituted lower aliphatic, aryl or heterocyclic group.

69. A compound of any of claims 1–19, which binds to a given SH2 domain with a $IC_{50}$ value of less than about 50 μM.

70. A compound of claim 69, which binds to a given SH2 domain with a $IC_{50}$ value of less than about 20 μM.

71. A compound of claim 69 wherein the SH2 domain is from a Src, Fyn, Lck, Yes, Blk, Lyn, Fgr, Hck, Yrk, ZAP-70, Syk, STAT or Abl protein.

72. A composition comprising a compound of any of claims 1–19, or a pharmaceutically acceptable derivative thereof, and a pharmaceutically acceptable excipient.

73. A method for inhibiting SH2-mediated signal transduction in a mammal in need thereof which comprises administering to the mammal a pharmaceutical composition of claim 72.

74. The method of claim 73, wherein the pharmaceutical composition contains a compound which specifically binds to an SH2 domain of Src, ZAP-70, Syk, or STAT 6.

75. The method of claim 73, wherein said SH2-mediated signal transduction is mediated by a PDGF receptor protein, EGF receptor protein, HER2/Neu receptor protein, fibroblast growth factor receptor protein, focal adhesion kinase protein, p130 protein, or p68 protein.

76. The method of claim 73, wherein the mammal has a proliferative disease, restenosis, osteoporosis, inflammation, allergies, or cardiovascular disease.

77. The method of claim 73, wherein the mammal has a cancer.

78. A method of treating a patient who has a proliferative disease, restenosis, osteoporosis, inflammation, allergic reaction, or cardiovascular disease, the method comprising administering to the patient a therapeutically effective amount of a composition of claim 72.

79. A method of treating a patient who has a cancer, the method comprising administering to the patient a therapeutically effective amount of a composition of claim 72.

80. A method for inducing immunosuppression in a patient, the method comprising administering to the patient an amount of a composition of claim 72 sufficient to cause immunosuppression.

81. A compound of the structure:

wherein each of $R^9$ and $R^{10}$ is independently halo, R, —OR, —SR, —NRR, —COR, or —$(M)_nW$—NHR;

each occurrence of M is an independently selected, substituted or unsubstituted, methylene moiety;

each n is independently 0, 1, 2, 3, 4 or 5;

each occurrence of R (unnumbered) represents hydrogen or an aliphatic, heteroaliphatic, aryl, heteroaryl, (aryl)aliphatic-, or (heteroaryl)aliphatic-moiety, each of which (other than hydrogen) may be substituted or unsubstituted; and, W is —CO—, —CS—, —M—, —SO—, or —$SO_2$—.

* * * * *